United States Patent
Parham et al.

(10) Patent No.: US 12,336,428 B2
(45) Date of Patent: Jun. 17, 2025

(54) MATERIALS FOR ELECTRONIC DEVICES

(71) Applicant: Merck Patent GmbH, Darmstadt (DE)

(72) Inventors: Amir Hossain Parham, Darmstadt (DE); Irina Martynova, Griesheim (DE); Anja Jatsch, Darmstadt (DE); Thomas Eberle, Darmstadt (DE); Jonas Valentin Kroeber, Darmstadt (DE); Christof Pflumm, Darmstadt (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 18/513,954

(22) Filed: Nov. 20, 2023

(65) Prior Publication Data

US 2024/0130231 A1 Apr. 18, 2024

Related U.S. Application Data

(63) Continuation of application No. 16/543,685, filed on Aug. 19, 2019, now Pat. No. 11,856,849, which is a continuation of application No. 15/027,381, filed as application No. PCT/EP2014/002496 on Sep. 16, 2014, now Pat. No. 10,529,930.

(30) Foreign Application Priority Data

Oct. 8, 2013 (EP) ..................................... 13004837

(51) Int. Cl.
| | | |
|---|---|---|
| H01L 51/54 | (2006.01) | |
| A61K 41/00 | (2020.01) | |
| A61N 5/06 | (2006.01) | |
| C07D 403/08 | (2006.01) | |
| C07D 403/10 | (2006.01) | |
| C07D 403/14 | (2006.01) | |
| C07D 405/14 | (2006.01) | |
| C07D 409/14 | (2006.01) | |
| C07D 491/048 | (2006.01) | |
| C07D 495/14 | (2006.01) | |
| C07F 5/02 | (2006.01) | |
| C07F 7/08 | (2006.01) | |
| C07F 15/00 | (2006.01) | |
| C09K 11/02 | (2006.01) | |
| H10K 85/60 | (2023.01) | |
| H10K 50/11 | (2023.01) | |
| H10K 85/30 | (2023.01) | |
| H10K 101/00 | (2023.01) | |
| H10K 101/10 | (2023.01) | |

(52) U.S. Cl.
CPC ......... *H10K 85/6572* (2023.02); *A61K 41/00* (2013.01); *A61N 5/0616* (2013.01); *A61N 5/0621* (2013.01); *C07D 403/08* (2013.01); *C07D 403/10* (2013.01); *C07D 403/14* (2013.01); *C07D 405/14* (2013.01); *C07D 409/14* (2013.01); *C07D 491/048* (2013.01); *C07D 495/14* (2013.01); *C07F 5/025* (2013.01); *C07F 7/0814* (2013.01); *C07F 15/0033* (2013.01); *C07F 15/0086* (2013.01); *C09K 11/025* (2013.01); *H10K 85/654* (2023.02); *H10K 85/657* (2023.02); *H10K 85/6574* (2023.02); *H10K 85/6576* (2023.02); *A61N 2005/0653* (2013.01); *H10K 50/11* (2023.02); *H10K 85/342* (2023.02); *H10K 85/631* (2023.02); *H10K 2101/10* (2023.02); *H10K 2101/90* (2023.02); *Y02E 10/549* (2013.01)

(58) Field of Classification Search
None
See application file for complete search history.

(56) References Cited

U.S. PATENT DOCUMENTS

| | | | |
|---|---|---|---|
| 9,677,635 B2 | 6/2017 | Bares et al. | |
| 2011/0306922 A1 | 12/2011 | Khan et al. | |
| 2012/0071668 A1 | 3/2012 | Suzuki et al. | |
| 2012/0085997 A1 | 4/2012 | Sugita et al. | |
| 2012/0223276 A1 | 9/2012 | Parham et al. | |
| 2015/0031787 A1 | 1/2015 | Bares et al. | |
| 2015/0280133 A1 | 10/2015 | Parham et al. | |
| 2016/0164002 A1 | 6/2016 | Parham et al. | |

FOREIGN PATENT DOCUMENTS

| | | |
|---|---|---|
| JP | 2012-232922 A | 11/2012 |
| JP | 2013-510803 A | 3/2013 |
| JP | 2014-103103 A | 6/2014 |
| JP | 2014-116454 A | 6/2014 |
| JP | 2016-530366 A | 9/2016 |
| JP | 2016-534095 A | 11/2016 |
| TW | 201134823 A | 10/2011 |
| WO | 2011/057706 A2 | 5/2011 |
| WO | 2014/067614 A1 | 5/2014 |
| WO | 2015/014434 A1 | 2/2015 |

OTHER PUBLICATIONS

European Office Action dated Jan. 23, 2018 for European Patent Application No. 14 766 666.3.
International Preliminary Report on Patentability received for PCT Patent Application No. PCT/EP2014/002496, mailed on Apr. 21, 2016, 17 pages (10 pages of English Translation and 7 pages of Original Document).
International Search Report and Written Opinion received for PCT Patent Application No. PCT/EP2014/002496, mailed on Dec. 18, 2014, 22 pages (11 pages of English Translation and 11 pages of Original Document).

*Primary Examiner* — Andrew K Bohaty
(74) *Attorney, Agent, or Firm* — Faegre Drinker Biddle & Reath LLP

(57) ABSTRACT

The application relates to compounds having functional substituents in a specific spatial arrangement, to devices comprising same, and to the preparation and use thereof.

22 Claims, No Drawings

MATERIALS FOR ELECTRONIC DEVICES

CROSS-REFERENCE TO RELATED APPLICATIONS

This application is a continuation of U.S. application Ser. No. 16/543,685, filed Aug. 19, 2019, which is a continuation of U.S. Ser. No. 15/027,381, filed Apr. 5, 2016, which is a National stage application (under 35 U.S.C. § 371) of PCT/EP2014/002496, filed Sep. 16, 2014, which claims benefit of European Application No. 13004837.4, filed Oct. 8, 2013, all of which are incorporated herein by reference in their entirety.

The present invention relates to cyclic compounds having a specific arrangement of electron-conducting and hole-conducting groups, to the use thereof in electronic devices, to the preparation thereof, and to electronic devices.

The structure of organic electroluminescent devices (for example OLEDs—organic light-emitting diodes, or OLECs—organic light-emitting electrochemical cells) in which organic semiconductors are employed as functional materials is described, for example, in U.S. Pat. Nos. 4,539,507, 5,151,629, EP 0676461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). For quantum-mechanical reasons, an up to four-fold increase in energy and power efficiency is possible using organometallic compounds as phosphorescence emitters. In general, there is still a need for improvement, in particular with respect to efficiency, operating voltage and lifetime, both in the case of OLEDs which exhibit singlet emission and also in the case of OLEDs which exhibit triplet emission. This applies, in particular, to OLEDs which emit in the relatively short-wave region, i.e. green and in particular blue.

The properties of organic electroluminescent devices are not determined only by the emitters employed. In particular, the other materials used, such as host and matrix materials, hole-blocking materials, electron-transport materials, hole-transport materials and electron- or exciton-blocking materials, are also of particular importance here. Improvements in these materials can result in significant improvements in electroluminescent devices.

In accordance with the prior art, use is made, inter alia, of ketones (for example in accordance with WO 2004/093207 or WO 2010/006680) or phosphine oxides (for example in accordance with WO 2005/003253) as matrix materials for phosphorescent emitters. Further matrix materials in accordance with the prior art are triazines (for example WO 2008/056746, EP 0906947, EP 0908787, EP 0906948).

For fluorescent OLEDs, use is made in accordance with the prior art of, in particular, condensed aromatic compounds, in particular anthracene derivatives, as host materials, in particular for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl)anthracene derivatives for use in OLEDs. Further anthracene derivatives are disclosed in WO 01/076323, WO 01/021729, WO 2004/013073, WO 2004/018588, WO 2003/087023 or WO 2004/018587. Host materials based on aryl-substituted pyrenes and chrysenes are disclosed in WO 2004/016575. Host materials based on benzanthracene derivatives are disclosed in WO 2008/145239. For high-quality applications, it is desirable to have improved host materials available.

The prior art discloses the use of compounds containing one or more carbazole groups in electronic devices, for example in WO 2005/039246, US 2005/0069729, JP 2004/288381, EP 1205527 or WO 2008/086851.

The prior art furthermore discloses the use of compounds containing one or more indenocarbazole groups in electronic devices, for example in WO 2010/136109 and WO 2011/000455.

The prior art furthermore discloses the use of compounds containing one or more electron-deficient heteroaromatic six-membered rings in electronic devices, for example in WO 2010/015306, WO 2007/063754 and WO 2008/056746.

WO 2009/069442 discloses tricyclic compounds, such as carbazole, dibenzofuran or dibenzothiophene, which are highly substituted by electron-deficient heteroaromatic groups (for example pyridine, pyrimidine or triazine). The tricyclic compounds are not substituted by hole-conducting groups, i.e. electron-rich groups.

JP 2009-21336 discloses substituted carbazoles as matrix materials, where the carbazoles are substituted by an electron-conducting group and by a hole-conducting group. However, the compounds have no face-to-face substitution.

WO 2011/057706 discloses substituted carbazoles as matrix materials, where the carbazoles are substituted by an electron-conducting group and by a hole-conducting group. However, most of the carbazoles disclosed have no face-to-face substitution. In the case of the face-to-face arrangements occasionally disclosed, however, the hole- or electron-conducting group is bonded directly to the tricyclic compound.

However, there is still a need for improvement on use of these materials as in the case of other materials, in particular with respect to the efficiency and the lifetime of the device.

The object of the present invention is therefore the provision of compounds which are suitable for use in a fluorescent or phosphorescent OLED, for example as host material and/or matrix material or as hole-transport/electron-blocking material or exciton-blocking material or as electron-transport or hole-blocking material, and which result in good device properties when used in an OLED, and the provision of the corresponding electronic device.

Surprisingly, it has been found that certain compounds described in greater detail below achieve these objects and result in good properties of the organic electroluminescent device, in particular with respect to the lifetime, the efficiency and the operating voltage. The present invention therefore relates to electronic devices, in particular organic electroluminescent devices, which comprise compounds of this type, and to the corresponding preferred compounds. The surprising effects are achieved by a specific arrangement ("face-to-face" arrangement of groups) of electron-conducting and hole-conducting groups in compounds of the formulae shown below. Without being tied to a theory, the rapid charge transport could be due to the relatively well-defined (highly ordered) parallel alignment of the molecules (face-to-face arrangement), in which a certain close-range ordering of the molecules is present. Due to the small separations of the groups from one another, intermolecular interactions, such as, for example, direct n-n interaction, could also be the cause of the rapid charge transfer.

The compounds according to the invention also have a high glass transition temperature ($T_g$), which is advantageous with respect to the processing of the compounds in the production of electronic devices. The high glass-transition temperature of the compounds also allows the use of the compounds in thin amorphous organic layers.

Furthermore, the compounds according to the invention allow stabilisation of the charge carriers in the excited state and have a sufficiently high triplet energy, which represents an important prerequisite for phosphorescent devices. Furthermore, the compounds according to the invention exhibit improved performance data in OLEDs compared with the compounds from the prior art.

The present invention therefore relates to compounds of the general formula (1)

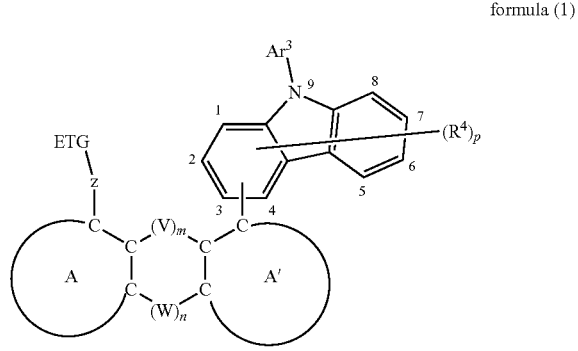

formula (1)

where the following applies to the symbols and indices used:

A and A' are, identically or differently from one another, an aromatic or heteroaromatic ring having 5 or 6 ring atoms, which may be substituted by one or more radicals $R^1$, which may be independent of one another;

ETG is an organic electron-transporting group (ETG) from the group of electron-deficient heteroaromatic groups, where the ETG preferably a heteroaryl group having 5 to 60 aromatic ring atoms, where nitrogen atoms represent very preferred heteroatoms and very particularly preferred ETGs are selected from the group triazines, pyrimidines, pyrazines, pyrazoles, pyridazines, quinoles, isoquinolines, thiazoles, benzothiazoles, oxazoles, benzoxazoles, imidazoles, benzimidazoles and pyridines and where the group ETG may be substituted by one or more radicals $R^1$, which are independent of one another, Z is a single bond or a divalent group; if Z is a single bond, the group ETG is then bonded directly to the carbon atom of ring A;

V is a single bond, C=O, $C(R^1)_2$, $NAr^3$, O, S, $Si(R^1)_2$, $BR^1$, $PR^1$, $P(=O)R^1$, SO or $SO_2$, where, in the case of a single bond, the carbon atoms of rings A and A' are connected directly to one another by a single bond, where a single bond, $C(R^1)_2$, $NAr^3$, O and S are preferred, where a single bond, $C(R^1)_2$, O and S are very preferred, where O and S are very particularly preferred, where O is especially preferred;

W is a single bond, C=O, $C(R^1)_2$, $NR^1$, O, S, $Si(R^1)_2$, $BR^1$, $PR^1$, $P(=O)R^1$, SO or $SO_2$, where, in the case of a single bond, the carbon atoms of rings A and A' are connected directly to one another by a single bond, where a single bond, $C(R^1)_2$, $NR^1$, O and S are preferred, where a single bond, $C(R^1)_2$, O and S are very preferred, where O and S are very particularly preferred, where O is especially preferred;

where it is furthermore preferred for V to be a single bond if W is not a single bond or for W to be a single bond if V is not a single bond;

where it is furthermore very preferred for V to be a single bond if W is equal to O or S or for W to be a single bond if V is equal to O or S;

where it is furthermore very particularly preferred for V to be a single bond if W is equal to O or for W to be a single bond if V is equal to O;

m is either 0 or 1;
n is either 0 or 1,
where m=n;

$Ar^3$ is an aromatic or heteroaromatic ring or ring system having 5 to 30 ring atoms, where the ring or the may in each case be substituted by one or more radicals $R^2$, which may be substituted by one or more radicals $R^3$, where two or more radicals $R^2$ may form a ring closure with one another;

$R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups or a crosslinkable group Q; two or more adjacent radicals $R^1$ here may form a mono- or polycyclic, aliphatic or aromatic ring system with one another, where it is preferred for two or more adjacent radicals $R^1$ not to form a mono- or polycyclic, aliphatic or aromatic or heteroaromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which may be substituted by one or more radicals $R^3$, or a diarylamino group, diheteroarylamino group or arylheteroarylamino group having 10 to 40 aromatic ring atoms, which may be substituted by one or more radicals $R^3$, or a combination of two or more of these groups; two or more adjacent radicals $R^2$ here may form a mono- or polycyclic, aliphatic or aromatic or heteroaromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents $R^3$ here may also form a mono- or polycyclic, aliphatic or aromatic or heteroaromatic ring system with one another;

p is an integer from 1 to 7, preferably from 1 to 4, very preferably from 1 to 3, particularly preferably 1 or 2, very particularly preferably precisely 2 and especially preferably precisely 1;

$R^4$ is, identically or differently on each occurrence, $N(R^2)_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, C=C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more adjacent radicals $R^4$ here may form a mono- or polycyclic, aliphatic or aromatic ring system with one another.

If two or more adjacent radicals do not form a mono- or polycyclic, aliphatic or aromatic or heteroaromatic ring system with one another, these radicals cannot become part of a ring or ring system. If, for example, the radical $R^1$ is defined so that two or more adjacent radicals $R^1$ do not form a mono- or polycyclic, aliphatic or aromatic or heteroaromatic ring system with one another, but the radicals $R^1$ may themselves again be substituted by radicals $R^2$, where two or more adjacent radicals $R^2$ may form a mono- or polycyclic, aliphatic or aromatic or heteroaromatic ring system with one another, then the ring closure of the radicals $R^2$ cannot take place in such a way that the radicals $R^1$ become part of a ring or ring system.

It is preferred for the ETG, which may be substituted by one or more radicals $R^1$, to contain no electron-rich aromatic or heteroaromatic rings or ring systems.

The compound of the general formula (1) therefore always contains at least one substituent $R^4$ which is other than hydrogen.

The bonding of the radicals $R^4$ can take place at all as yet unsubstituted positions 1 to 8 of the carbazole, where it is preferred for the radicals $R^4$ to be bonded at positions 5, 6, 7 and 8 of the carbazole.

The bonding of the carbazole ring in the compound of the formula (1) to the carbon atom of ring A' can take place via positions 1, 2, 3 and 4.

In a preferred embodiment, the bonding of the carbazole to ring A' takes place via position 1.

In another preferred embodiment, the bonding of the carbazole to ring A' takes place via position 2.

In another preferred embodiment, the bonding of the carbazole to ring A' takes place via position 3.

In still another preferred embodiment, the bonding of the carbazole to ring A' takes place via position 4.

Accordingly, for example, for the compounds of the general formula (1), in the case where m=n=1 and V=W=single bond, the general formula is as follows, where the following formula also represents a very particularly preferred embodiment of the present invention.

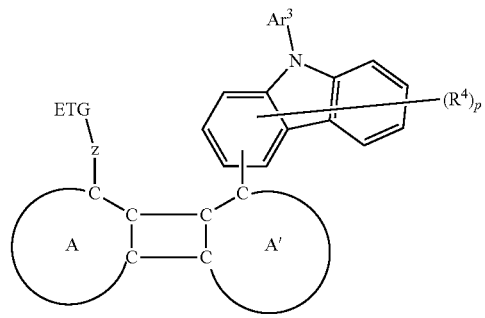

Furthermore, for example, for the compounds of the general formula (1), in the case where m=n=1 and V=O and W=single bond, the general formula is as follows, where the following formula also represents a very particularly preferred embodiment of the present invention.

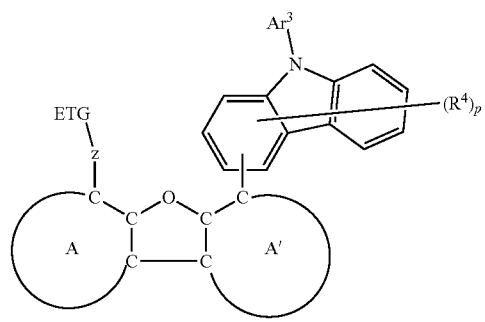

Furthermore, for example, for the compounds of the general formula (1), in the case where m=n=0, the general formula is as follows, where the following formula also represents a very particularly preferred embodiment of the present invention.

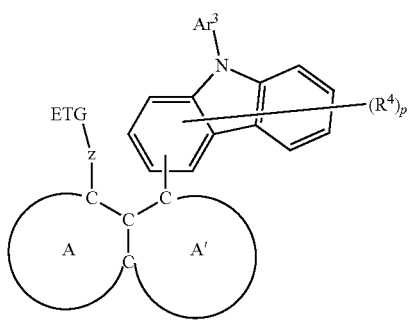

In a preferred embodiment, the compound is selected from the general formula (2)

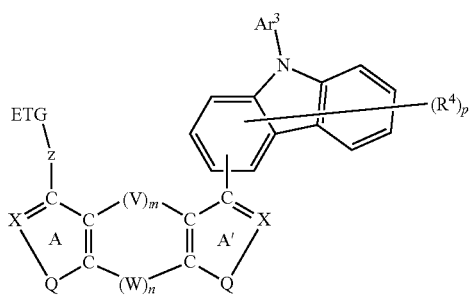

formula (2)

where the following applies to the symbols additionally used:

X is, identically or differently on each occurrence, N or $CR^1$;

Q is, identically or differently on each occurrence, X=X, S, O or $NR^1$, preferably X=X, S or O, very preferably X=X or S and very particularly preferably X=X.

Accordingly, great preference is given to a compound of the general formulae (3) to (11)

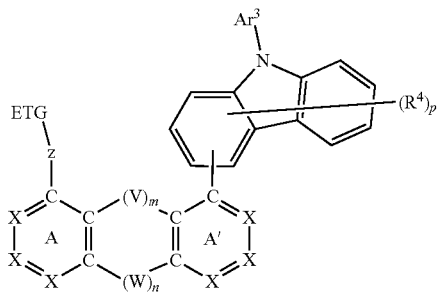

formula (3)

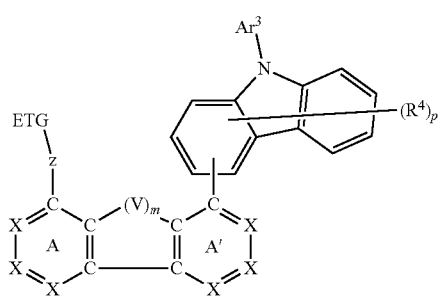

formula (4)

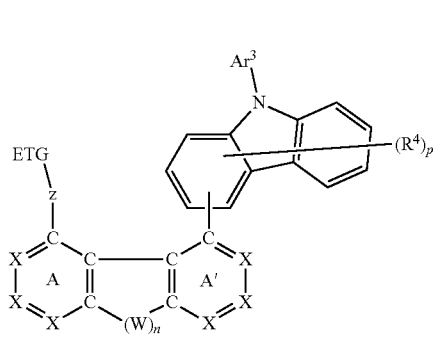

formula (5)

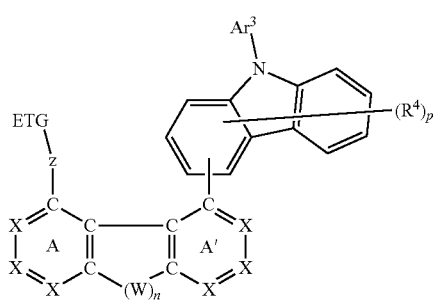

formula (6)

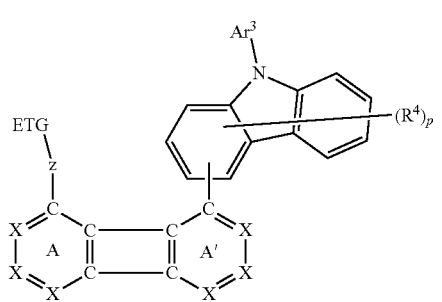

formula (7)

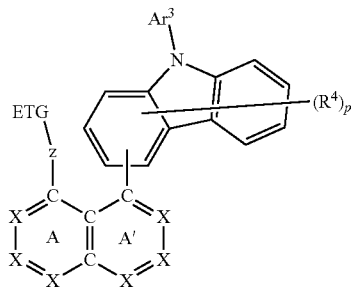

formula (8)

-continued formula (9)

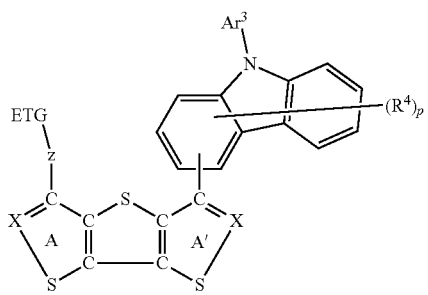

formula (10)

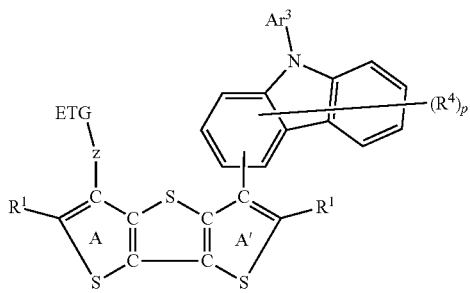

formula (11)

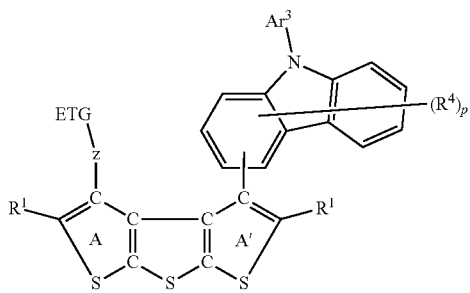

where a compound of the general formulae (3) to (8) is very particularly preferred and a compound of the general formula (4) is especially preferred.

It is furthermore very particularly preferred for X in the formulae (1) to (9) to be equal to $CR^1$.

In a preferred embodiment, the present invention relates to a compound of the formula (4), preferably a compound of the formula (4) where X is equal to $CR^1$ and m=1, very preferably a compound of the formula (4) where X is equal to $CR^1$, m=1 and V is equal to 0, where the above definitions and preferred embodiments apply to the other symbols and indices.

In a further preferred embodiment, the present invention relates to a compound of the formula (4) where X is equal to $CR^1$, m=1 and V is equal to N—$Ar^3$, where the above definitions and preferred embodiments apply to the other symbols and indices.

A further preferred compound in the sense of the present invention is one of the following formula (3a)

formula (3a)

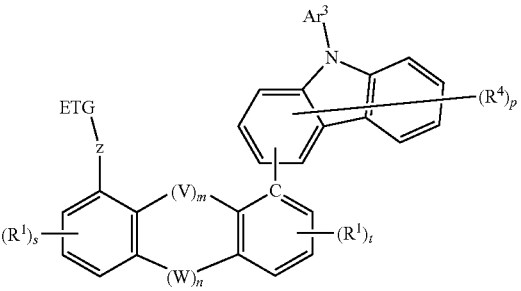

where s and t can be integers from 0 to 3 and where s+t is equal to an integer from 0 to 6, s+t is preferably equal to 4, s+t is very preferably equal to 2, s+t is very particularly preferably equal to 1 and s+t is especially preferably equal to 0.

A further preferred compound in the sense of the present invention is one of the following formula (3b)

formula (3b)

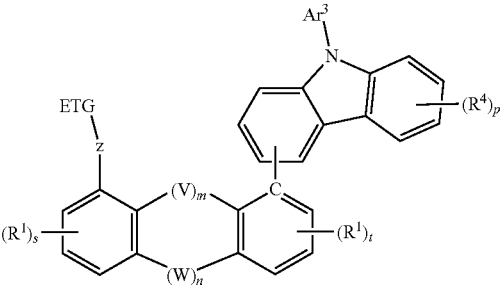

where p is an integer from 1 to 4, preferably precisely 2 and very preferably precisely 1.

A further preferred compound in the sense of the present invention is one of the following formula (3c)

formula (3c)

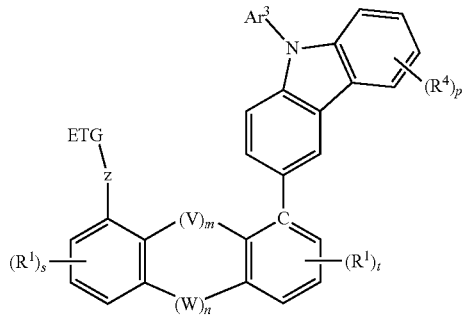

In a further preferred embodiment, the present invention relates to a compound of the general formula (12)

formula (12)

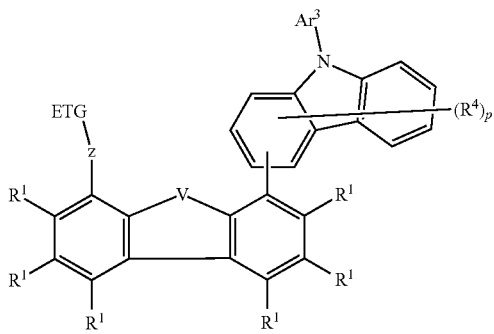

where V is equal to O or S and where the definitions and preferred embodiments given herein apply to the indices and symbols used. It is very preferred for V in the compound of the formula (12) to be equal to O.

In a further preferred embodiment, the present invention relates to a compound of the general formula (13)

formula (13)

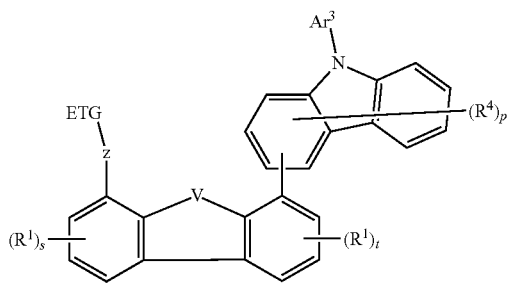

where V is equal to O or S and where the definitions and preferred embodiments given herein apply to the indices and symbols used and where the aromatic rings A and A' each have a maximum of one substituent $R^1$, i.e. s is equal to 0 or 1 and t is equal to 0 or 1, where s+t can be equal to 0, 1 or 2. It is very preferred for V in the compound of the formula (13) to be equal to O.

In a very preferred embodiment, the present invention relates to a compound of the general formula (14)

formula (14)

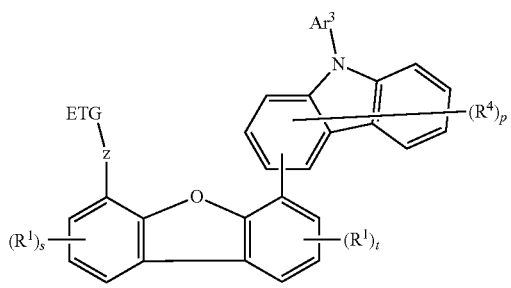

where the definitions and preferred embodiments given herein apply to the indices and symbols used and where the aromatic rings A and A' each have a maximum of one substituent $R^1$.

In a very particularly preferred embodiment, the present invention relates to a compound of the general formula (15)

formula (15)

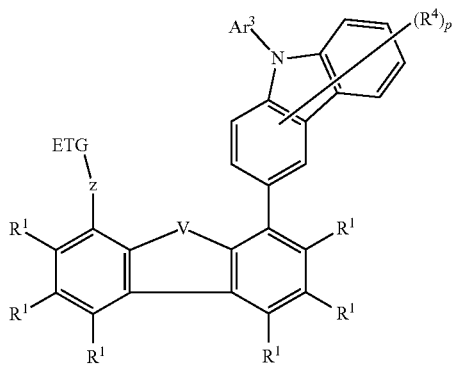

where the definitions and preferred embodiments given herein apply to the symbols used and where the two aromatic rings substituted by $R^1$ each have a maximum of one substituent $R^1$, where it is very preferred for $R^1$ on the two rings A and A' substituted by $R^1$ to be equal to H.

In a very particularly preferred embodiment, the present invention relates to a compound of the general formula (16)

formula (16)

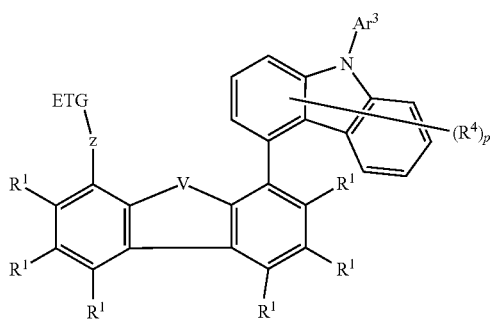

where the definitions and preferred embodiments given herein apply to the symbols used and where the two aromatic rings substituted by $R^1$ each have a maximum of one substituent $R^1$, where it is very preferred for $R^1$ on the two rings A and A' substituted by $R^1$ to be equal to H.

In a very particularly preferred embodiment, the present invention relates to a compound of the general formula (17)

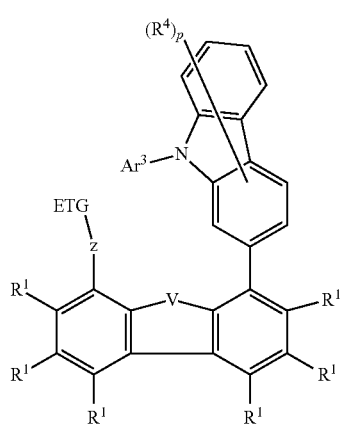

formula (17)

where the definitions and preferred embodiments given herein apply to the symbols used and where the two aromatic rings substituted by $R^1$ each have a maximum of one substituent $R^1$, where it is very preferred for $R^1$ on the two rings A and A' substituted by $R^1$ to be equal to H.

In a very particularly preferred embodiment, the present invention relates to a compound of the general formula (18)

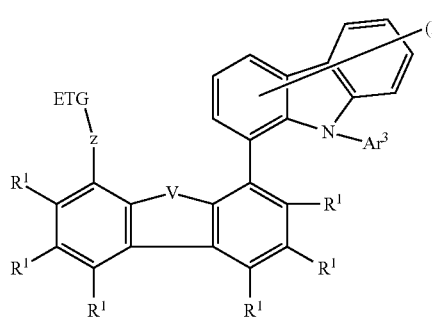

formula (18)

where the definitions and preferred embodiments given herein apply to the symbols used and where the two aromatic rings substituted by $R^1$ each have a maximum of one substituent $R^1$, where it is very preferred for $R^1$ on the two rings A and A' substituted by $R^1$ to be equal to H.

In a further very particularly preferred embodiment, the present invention relates to a compound of the general formula (19)

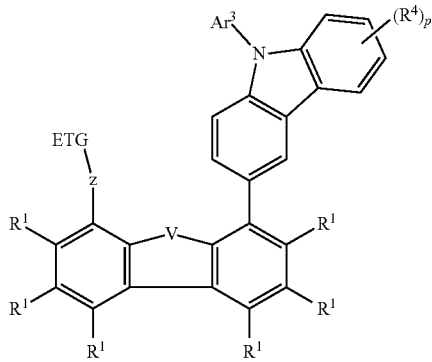

formula (19)

where the definitions and preferred embodiments given herein apply to the symbols used and where the two aromatic rings substituted by $R^1$ each have a maximum of one substituent $R^1$, where it is very preferred for $R^1$ on the two rings A and A' substituted by $R^1$ to be equal to H and where p is an integer from 1 to 4, preferably 1 or 2, very preferably precisely 2 and especially preferably precisely 1.

In a further very particularly preferred embodiment, the present invention relates to a compound of the general formula (20)

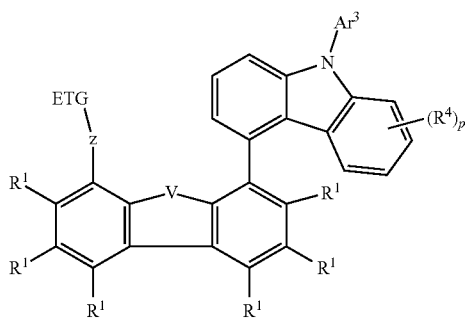

formula (20)

where the definitions and preferred embodiments given herein apply to the symbols used and where the two aromatic rings substituted by $R^1$ each have a maximum of one substituent $R^1$, where it is very preferred for $R^1$ on the two rings A and A substituted by $R^1$ to be equal to H and where p is an integer from 1 to 4, preferably 1 or 2, very preferably precisely 2 and especially preferably precisely 1.

In a further very particularly preferred embodiment, the present invention relates to a compound of the general formula (21)

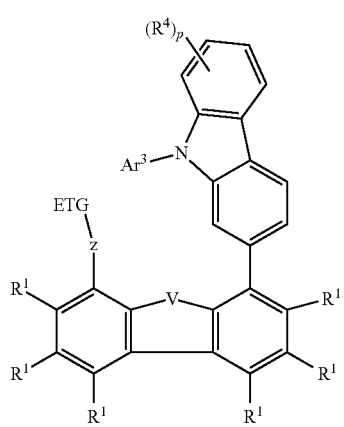

formula (21)

where the definitions and preferred embodiments given herein apply to the symbols used and where the two aromatic rings substituted by $R^1$ each have a maximum of one substituent $R^1$, where it is very preferred for $R^1$ on the two rings A and A' substituted by $R^1$ to be equal to H and where p is an integer from 1 to 4, preferably 1 or 2, very preferably precisely 2 and especially preferably precisely 1.

In a further very particularly preferred embodiment, the present invention relates to a compound of the general formula (22)

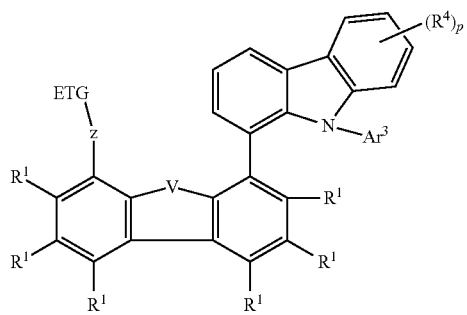

formula (22)

where the definitions and preferred embodiments given herein apply to the symbols used and where the two aromatic rings substituted by $R^1$ each have a maximum of one substituent $R^1$, where it is very preferred for $R^1$ on the two rings A and A' substituted by $R^1$ to be equal to H and where p is an integer from 1 to 4, preferably 1 or 2, very preferably precisely 2 and especially preferably precisely 1.

Z is preferably a single bond or a divalent aromatic or heteroaromatic ring or ring system having 5 to 60 ring atoms, preferably an aromatic ring or ring system having 5 to 60 ring atoms, where it is preferred for the ring or ring system to be bridged neither with the ring system containing the rings A and A' nor with the ETG, where Z is preferably a pyridylene, pyrimidyl-ene, phenylene, biphenylene or fluorene, spiro, terphenylene, thiophene, furan, dibenzofuran or dibenzothiophene group, where a phenylene, biphenylene or terphenylene group is particularly preferred and a phenylene group is very particularly preferred.

The formulation that two or more radicals may form a ring with one another is, for the purposes of the present application, intended to be taken to mean, inter alia, that the two radicals are linked to one another by a chemical bond. This is illustrated by the following scheme:

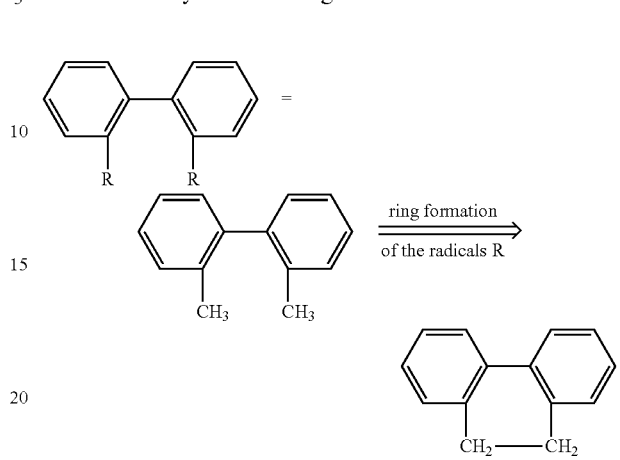

Furthermore, however, the above-mentioned formulation is also intended to be taken to mean that, in the case where one of the two radicals represents hydrogen, the second radical is bonded at the position to which the hydrogen atom was bonded, with formation of a ring. This is intended to be illustrated by the following scheme:

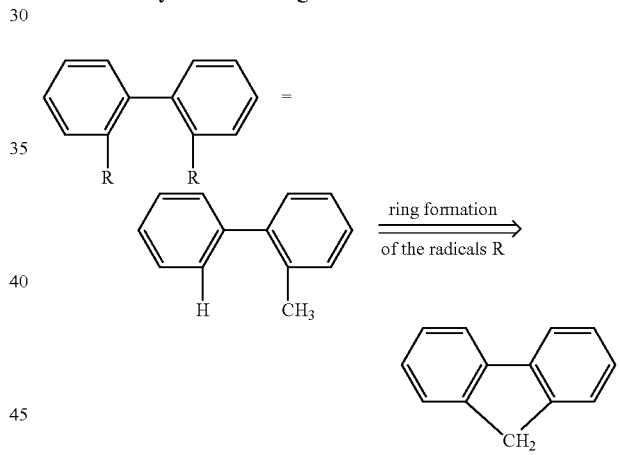

A condensed aryl group here is taken to mean an aryl group which contains two or more aromatic rings which are condensed with one another, i.e. share one or more aromatic bonds with one another. A corresponding definition applies to heteroaryl groups. Examples of condensed aryl groups, irrespective of the number of their ring atoms, are naphthyl, anthracenyl, pyrenyl, phenanthrenyl and perylenyl. Examples of condensed heteroaryl groups are quinolinyl, indolyl, carbazolyl and acridinyl.

The following are general definitions of chemical groups in the sense of the present application:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An electron-deficient heteroaryl group in the sense of the present invention is defined as a 5-membered heteroaryl ring group having at least two heteroatoms, for example imidazole, oxazole, oxadiazole, etc., or as a 6-membered heteroaryl ring group having at least one heteroatom, for example pyridine, pyrimidine, pyrazine, triazine, etc. Further 6-membered aryl or 6-membered heteroaryl ring groups may also be condensed onto these groups, as is the case, for example, in benzimidazole, quinoline or phenanthroline.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-trazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S.

An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyl-triazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-tri-fluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoro-ethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentyn-ylthio, hexynylthio, heptynylthio or octynylthio.

The group ETG is preferably an electron-deficient heteroaromatic group, which may be substituted by one or more radicals $R^1$. Even more preference is given to heteroaromatic groups having 6 aromatic ring atoms, at least one of which, preferably two of which and very preferably at least three of which is (are) an N atom, or heteroaromatic groups having 5 aromatic ring atoms, at least two of which are heteroatoms, preferably at least one of which is an N atom, which may be substituted by $R^1$, where further aryl or heteroaryl groups may in each case also be condensed onto these groups.

Preferred electron-deficient heteroaromatic groups here are selected from the following groups.

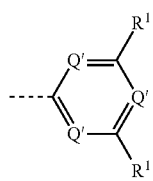

formula (E-1)

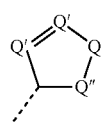

formula (E-2)

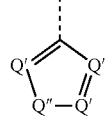

formula (E-3)

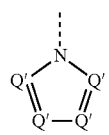

formula (E-4)

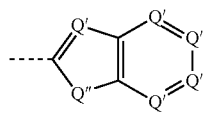

formula (E-5)

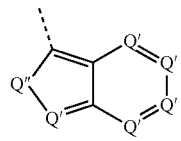

formula (E-6)

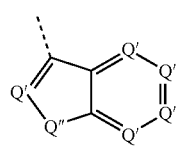

formula (E-7)

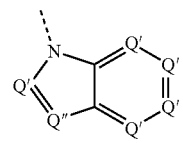

formula (E-8)

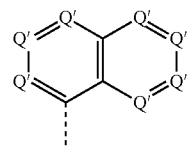

formula (E-9)

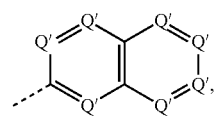

formula (E-10)

where the dashed bond marks the bonding position, $R^1$ is as defined above, and Q' represents on each occurrence, identically or differently, $CR^1$ or N, and Q" is $NR^1$, O or S;

where at least one Q' is equal to N and/or at least one Q" is equal to $NR^1$.

Preferred examples of electron-deficient heteroaromatic groups are: pyridines, pyrazines, pyrimidines, pyridazines, 1,2,4-triazines, 1,3,5-triazines, quinolines, isoquinolines, quinoxalines, pyrazoles, imidazoles, benzimidazoles, thiazoles, benzothiazoles, oxazoles or benzoxazoles, each of which may be substituted by $R^1$. The electron-transporting group is even more preferably a pyridine, pyrazine, pyrimidine, pyridazine or 1,3,5-triazine which is substituted by one or more radicals $R^1$.

Very preferred electron-deficient heteroaromatic groups are selected from the following groups:

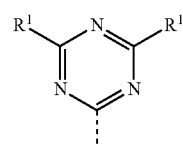

formula (E-11)

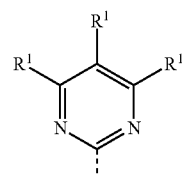

formula (E-12)

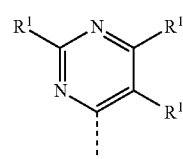

formula (E-13)

formula (E-14)
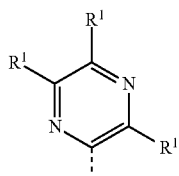

formula (E-15)
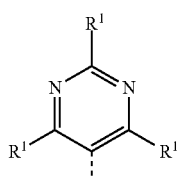

formula (E-16)
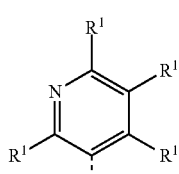

formula (E-17)
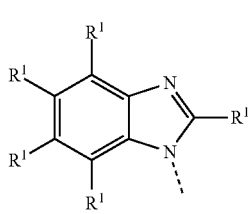

formula (E-18)
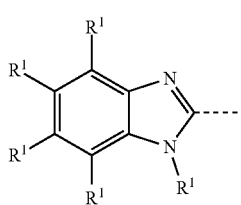

formula (E-19)
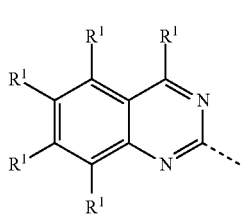

The substituents $R^1$ in the ETG are preferably selected from the group consisting of H or an aromatic or heteroaromatic ring system having 5 to 60 aromatic ring atoms, which may in each case be substituted by one or more radicals $R^2$, where the groups of the formula (E-11), (E-17) and (E-18) are even more preferred and the group of the formula (E-11) is most preferred.

Examples of very particularly preferred ETGs are the following groups, which may be substituted by one or more radicals $R^2$, which are independent of one another, where the dashed bonds denote the bonding positions to the groups $Ar^1$ and $Ar^2$.

formula (E-19)
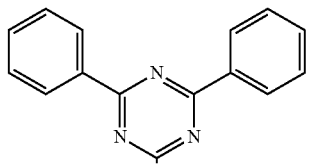

formula (E-20)
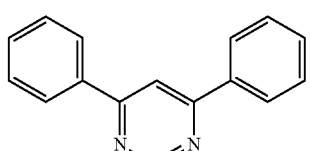

formula (E-21)
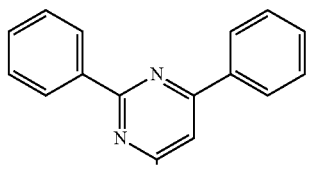

formula (E-22)
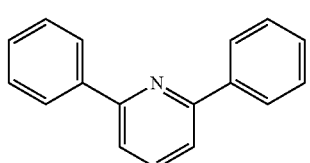

formula (E-23)
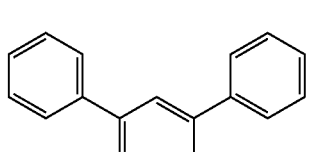

formula (E-24)

formula (E-25)
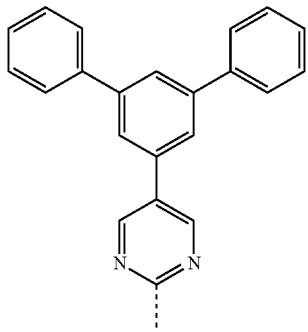

formula (E-26)
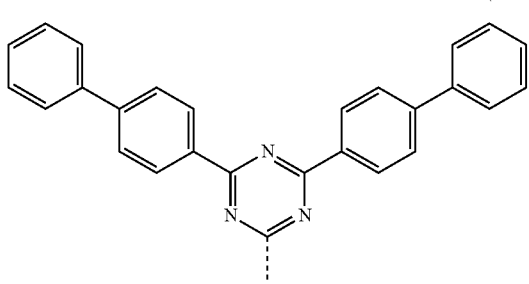

formula (E-27)
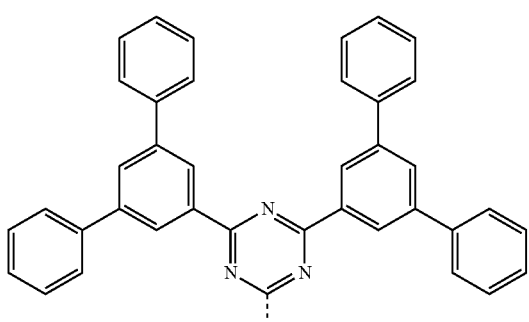

formula (E-28)
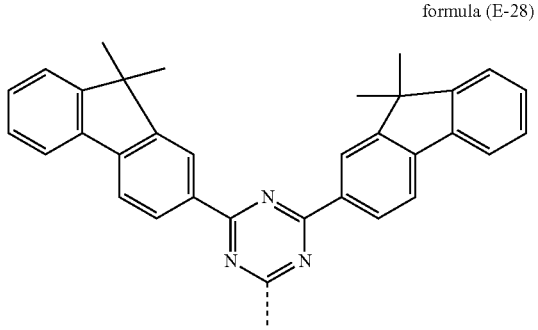

formula (E-29)
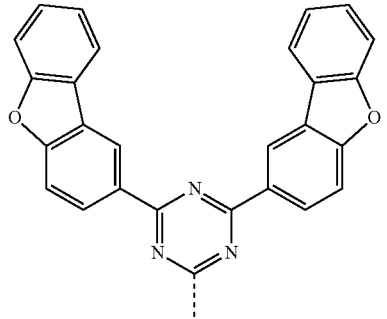

formula (E-30)
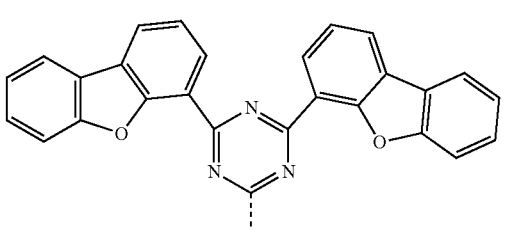

formula (E-31)
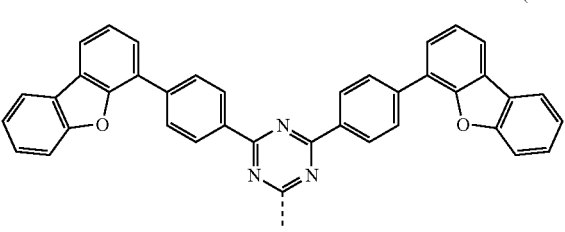

formula (E-32)
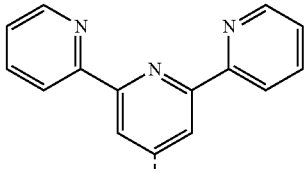

formula (E-33)
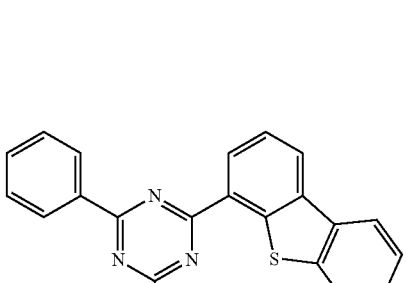

formula (E-34)
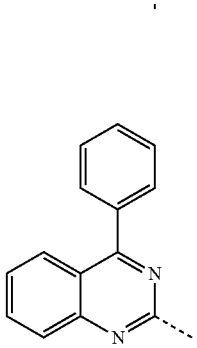

The electron-transport group preferably has an LUMO (lowest unoccupied molecular orbital) energy which is lower than −1.3 eV, very preferably lower than −2.5 eV and very particularly preferably lower than −2.7 eV. The LUMO energy of the electron-transport group determined using the method described below. In the calculations, the electron-tansport group is considered in isolation. In the groups of the formulae (E-1) to (E-34), the dashed bond is replaced by a bond to a phenyl radical. For example, the following compound is used for the calculation of the LUMO energy of the electrontransport group of the formula (E-19):

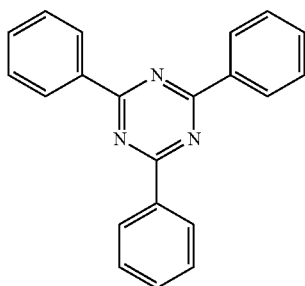 [SMILES: c1ccc(-c2nc(-c3ccccc3)nc(-c3ccccc3)n2)cc1]

Molecular orbitals, in particular also the highest occupied molecular orbital (HOMO) and the lowest unoccupied molecular orbital (LUMO), their energy levels and the energy of the lowest triplet state $T_1$ or the lowest excited singlet state $S_1$ of the materials are determined in the present application via quantum-chemical calculations. In order to calculate organic substances without metals, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SCF/DFT/Default Spin/B3PW91" method with the "6-31G(d)" base set is used here (charge 0, spin singlet). For metal-containing compounds, the geometry is optimised via the "Ground State/Hartree-Fock/Default Spin/LanL2 MB/Charge 0/Spin Singlet" method.

The energy calculation is carried out analogously to the method described above for the organic substances, with the difference that the "LanL2DZ" base set is used for the metal atom and the "6-31G(d)" base set is used for the ligands. The energy calculation gives the HOMO energy level HEh or LUMO energy level LEh in hartree units. The HOMO and LUMO energy levels in electron volts, calibrated with reference to cyclic voltammetry measurements, are determined therefrom as follows:

$$\text{HOMO}(eV)=((HEh*27.212)-0.9899)/1.1206$$

$$\text{LUMO}(eV)=((LEh*27.212)-2.0041)/1.385$$

For the purposes of this application, these values are to be regarded as HOMO and LUMO energy levels respectively of the materials.

The lowest triplet state $T_1$ is defined as the energy of the triplet state having the lowest energy which arises from the quantum-chemical calculation described.

The lowest excited singlet state $S_1$ is defined as the energy of the excited singlet state having the lowest energy which arises from the quantum-chemical calculation described.

The method described herein is independent of the software package used and always gives the same results. Examples of frequently used programs for this purpose are "Gaussian09 W" (Gaussian Inc.) and Q-Chem 4.1 (Q-Chem, Inc.).

Further preferably, the electron-transport group is characterised in that the electron mobility μ is $10^{-6}$ cm$^2$/(Vs) or more, very preferably $10^{-5}$ cm$^2$/(Vs) or more and very particularly preferably 104 cm$^2$/(Vs) or more. Analogously to the determination of the LUMO energies of the ETG, the ETG is for this purpose considered in isolation. Furthermore, the dashed bond in the groups of the formulae (E-1) to (E-34) is replaced by a bond to a phenyl radical.

In the compounds of the formula (1), the LUMO is preferably be localised on the electron-transport group. The LUMO is very preferably localised on the electron-transport group to the extent of more than 80%, and the LUMO is even more preferably not localised at all on the carbazole group. The absolute values of the HOMO and LUMO of the compound according to the invention especially preferably do not overlap at all. The person skilled in the art will have absolutely no difficulties in determining the overlap of the absolute values of the orbitals (overlap integral of the absolute values of the wave functions). To this end, the calculation method indicated herein is used and orbitals having a probability density of 90% are assumed.

$Ar^3$ is preferably an aromatic or heteroaromatic ring or ring system having 5 to 30 ring atoms, where the ring or the may in each case be substituted by one or more radicals $R^2$, which may be substituted by one or more radicals $R^3$.

$Ar^3$ is very preferably an aromatic ring or ring system having 5 to 30 ring atoms, where the ring or the may in each case be substituted by one or more radicals $R^2$, which may be substituted by one or more radicals $R^3$, where it is even more preferred for $Ar^3$ to be unsubstituted.

Very particularly preferred aromatic groups are phenyl, biphenyl, terphenyl and quaterphenyl.

$Ar^3$ is very preferably a heteroaromatic ring or ring system having 5 to 30 ring atoms, where the ring or the may in each case be substituted by one or more radicals $R^2$, which may be substituted by one or more radicals $R^3$, where it is even more preferred for $Ar^3$ to be unsubstituted.

Very particularly preferred heteroaromatic groups are furan, dibenzofuran, thiophene, benzothiophene, dibenzothiophene, carbazole, phenanthridine and quinoxaline.

In a preferred embodiment, the radicals $R^4$ are bridged to one another or the radicals $R^4$ are bridged with the carbazole by O, S, NAr$^3$ or C(R$^2$)$_2$.

In a very preferred embodiment, p=2, and it is very particularly preferred for the two radicals $R^4$ to form a ring closure, so that especially preferably indenocarbazoles or indolocarbazoles form, which may in turn be substituted by one or more radicals $R^2$, which are independent of one another.

In a further preferred embodiment, the radicals $R^4$ are not bridged to one another.

In a further preferred embodiment, the radicals $R^4$ are not bridged with the carbazole.

In a preferred embodiment of the present invention, $R^4$ is, identically or differently on each occurrence, N(R$^2$)$_2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more adjacent radicals $R^4$ here may form a mono- or polycyclic, aliphatic or aromatic ring system with one another.

In a very preferred embodiment of the present invention, $R^4$ is, identically or differently on each occurrence, an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more adjacent radicals $R^4$ here may form a mono- or polycyclic, aliphatic or aromatic ring system with one another.

$R^4$ is particularly preferably, identically or differently on each occurrence, an aromatic or heteroaromatic ring system having 5 to 60 aromatic ring atoms, which may in each case be substituted by one or more radicals $R^2$; two or more adjacent radicals $R^4$ here may form a polycyclic, aromatic ring system with one another.

Very particularly preferred aromatic or heteroaromatic ring systems for $R^4$ are phenyl, biphenyl, terphenyl, quaterphenyl, carbazole, dibenzofuranyl, each of which may be substituted by one or more $R^2$ and are very particularly preferably unsubstituted.

The compounds according to the invention can be prepared in accordance with Schemes 1 and 2.

The corresponding monoboronic acids (a) can be prepared by Suzuki coupling and subsequent siylation (Scheme 1). A further possibility is to prepare the corresponding monoboronic acids starting from the mono-bromides by Buchwald coupling and subsequent siylation (Scheme 2). The reaction of these monoboronic acids with corresponding aryl bromides or aryl chlorides via Suzuki coupling leads to the target compounds.

Scheme 1

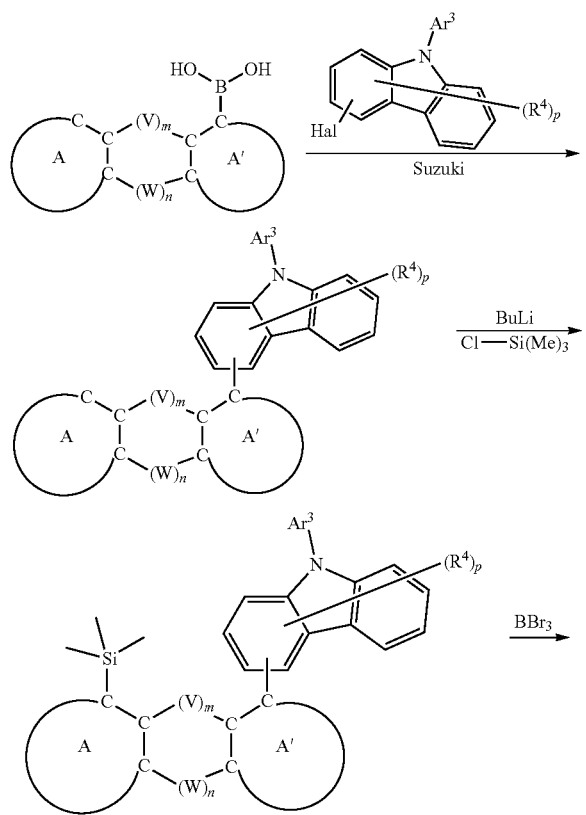

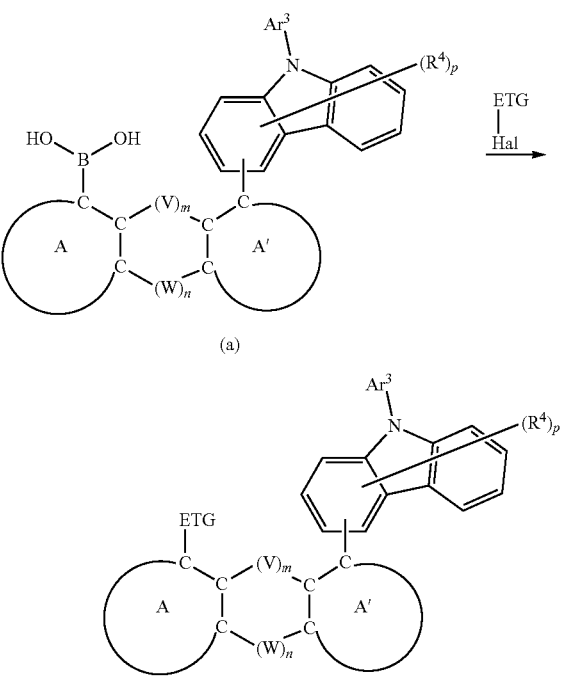

(a)

where the definitions given above and the preferred embodiments thereof apply to the indices and symbols used.

The Suzuki reaction is well known to the person skilled in the art, and he is presented with absolutely no difficulties in applying the reactions and known variations thereof to the compounds according to the invention in order to prepare them in the claimed scope while taking into account general expert knowledge. Furthermore, both in the Suzuki reaction and also in the Buchwald reaction, the chemical functionalities can be exchanged between substituent and the structure containing rings A and A'. This means that it is also possible for the substituent containing ETG or carbazole to contain the boronic acid, whereas the structure containing rings A and A' contains the halide. The following schemes illustrate the application of the said processes by way of example with reference to more specific cases, where the above definitions for the symbols and indices used apply. Hal stands for halides is preferably Br or I.

The present invention therefore also relates to a process for the preparation of the compound according to the invention by means of Suzuki coupling.

Scheme 2

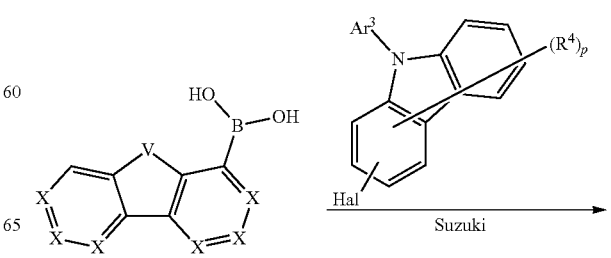

-continued

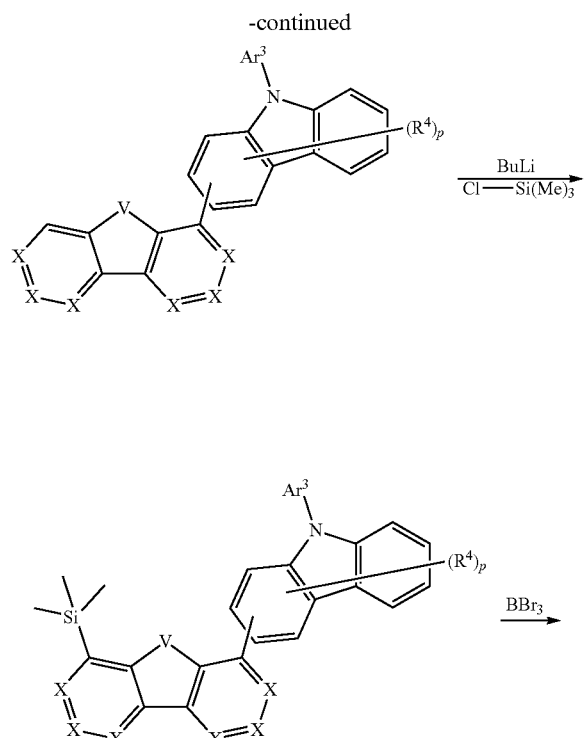

A further possibility for the preparation of the compounds according to the invention consists in reaction of a dihalide (Hal=Br, I) with 1 eq of the corresponding boronic acid and subsequent Szuki coupling to give the desired product, where the synthetic route uses similar steps as shown in Scheme 1.

A further possibility is reaction of the dihalide with 2 eq of the boronic acid of the ETG.

Scheme 3

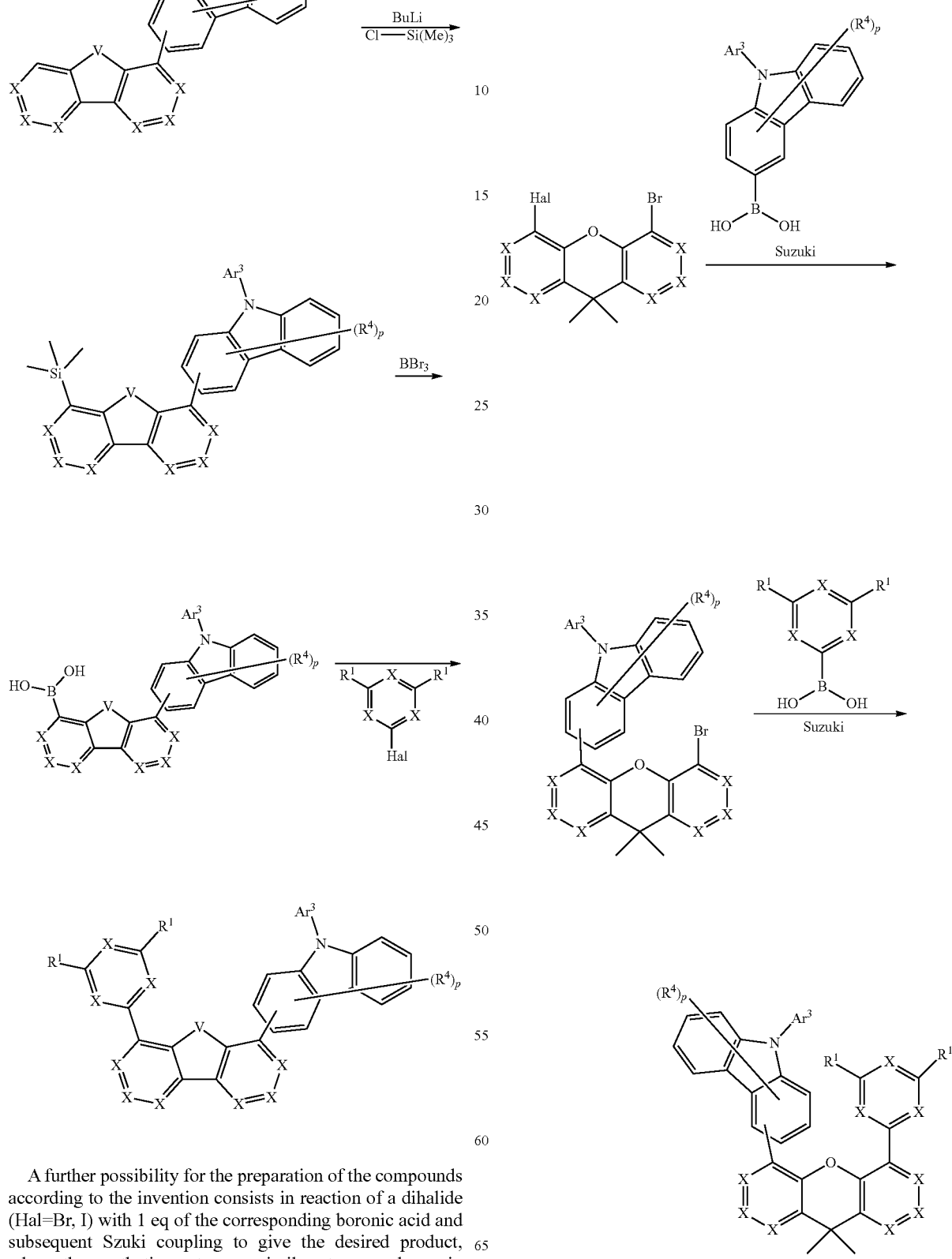

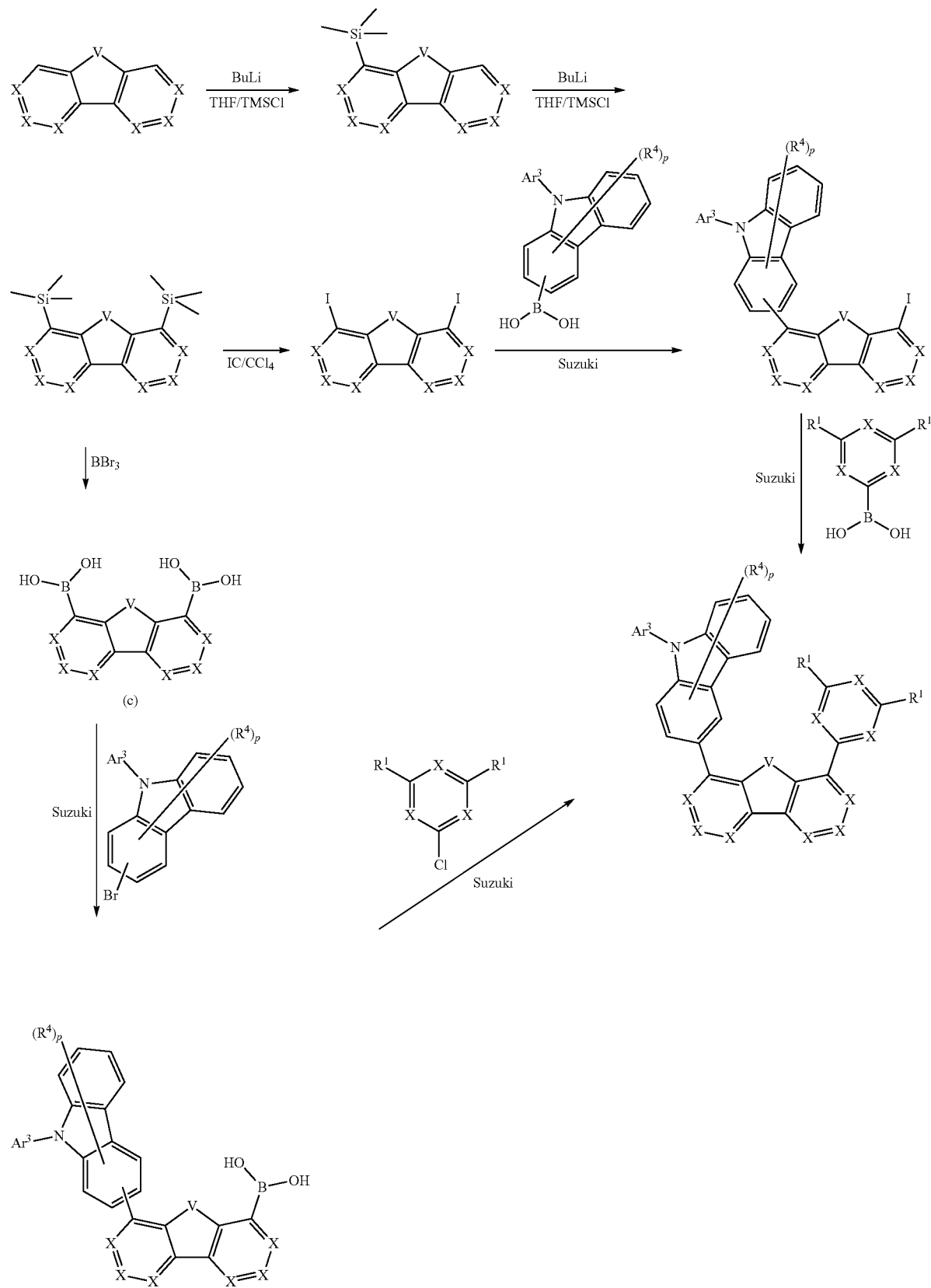

Many of the dihalides (b) or diboronic acids (c) are commercially available or can be synthesised as indicated in Scheme 5. They can subsequently be converted into the desired products via Suzuki couplings.

A further possibility for the preparation of compounds according to the invention is reaction of carbazole derivatives followed by an Ullmann or Buchwald coupling.

Scheme 5

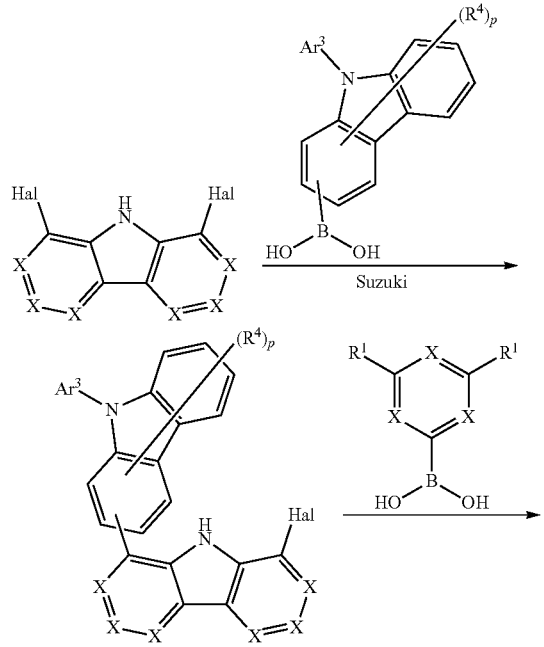

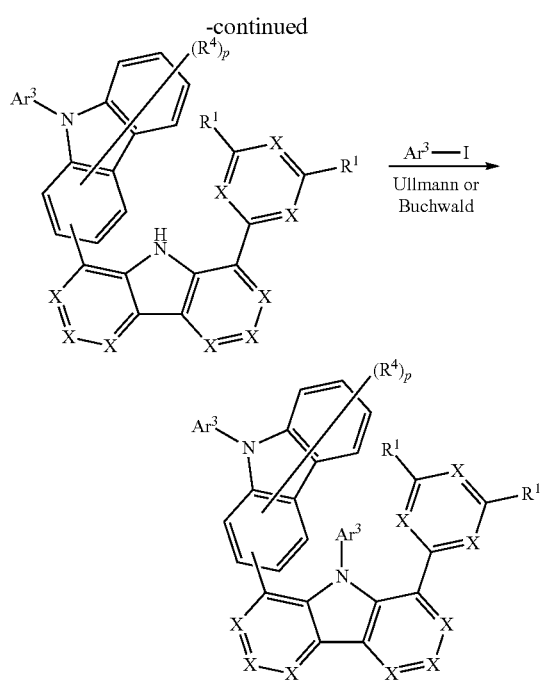

The processes shown for the synthesis of the compounds according to the invention should be regarded as illustrative. The person skilled in the art will be able to develop alternative synthetic routes within the scope of his general expert knowledge.

The following overview contains an illustrative depiction of compounds according to the invention which can be prepared by one of the processes described herein.

formula (A-1)

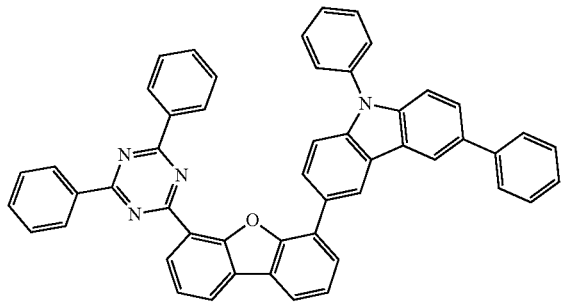

formula (A-2)

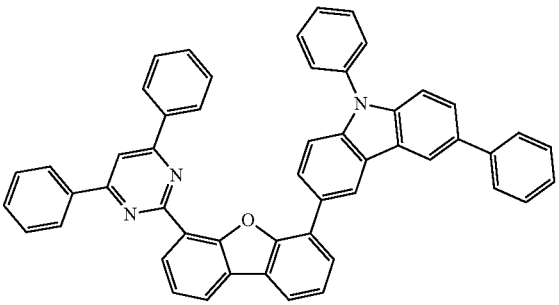

formula (A-3)

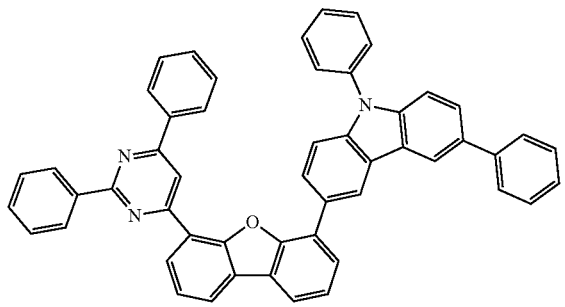

formula (A-4)

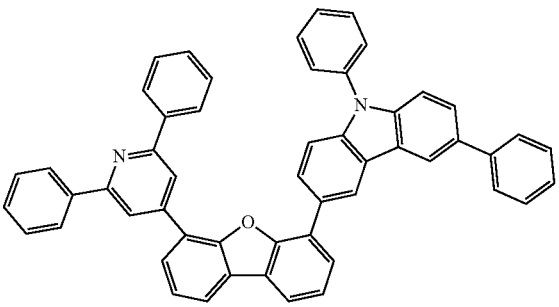

formula (A-5)
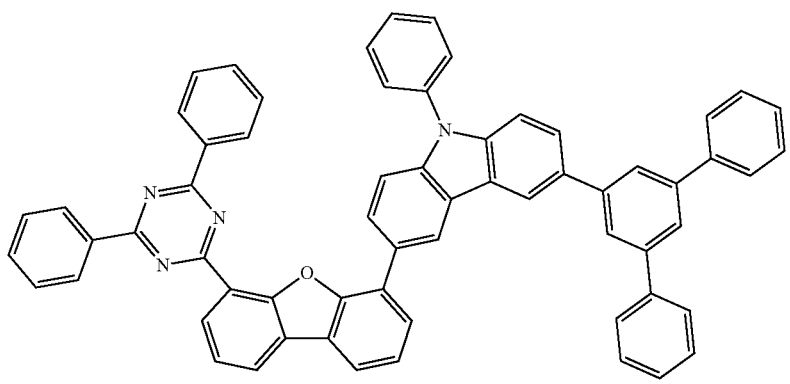
formula (A-6)
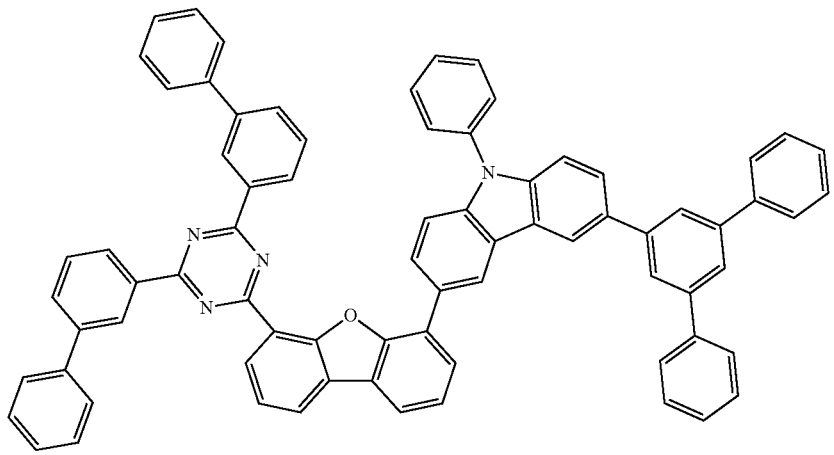
formula (A-7) formula (A-8)
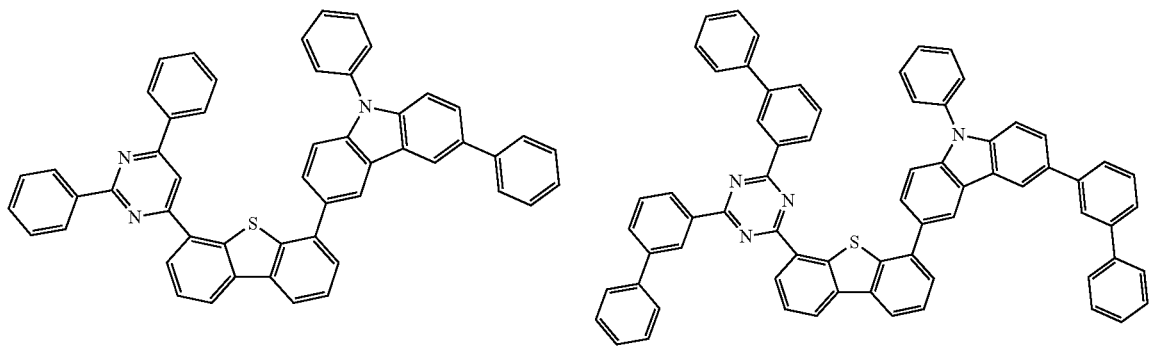
formula (A-8a)
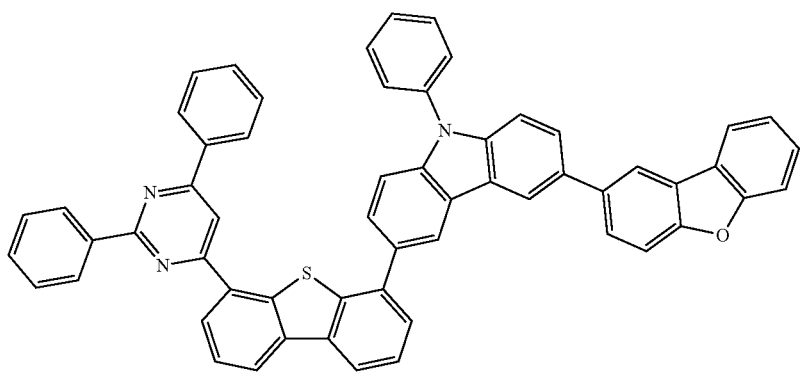

-continued
formula (A-8b)
formula (A-9)
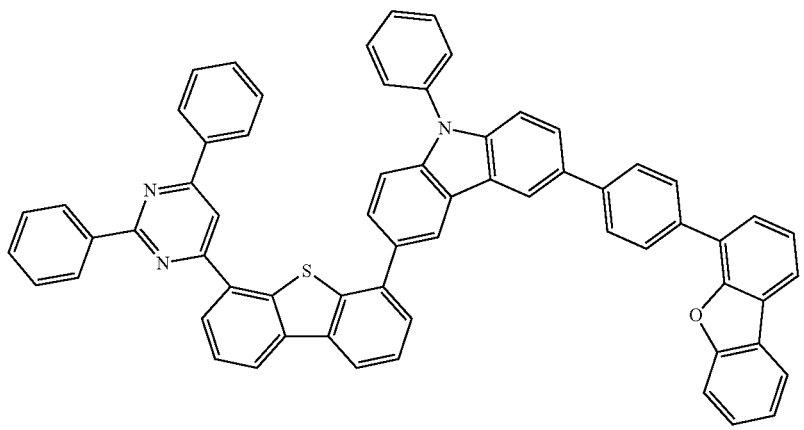
formula (A-10)
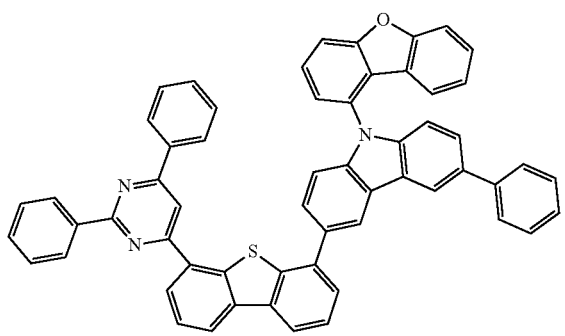
formula (A-11)
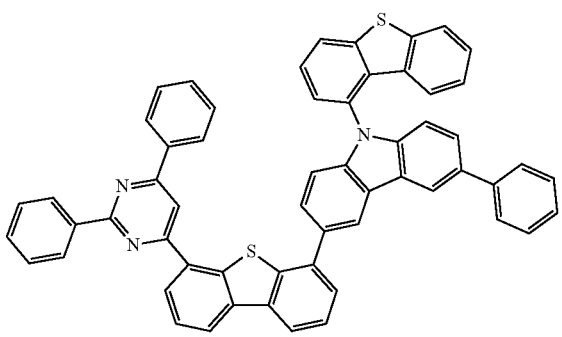
formula (A-12)
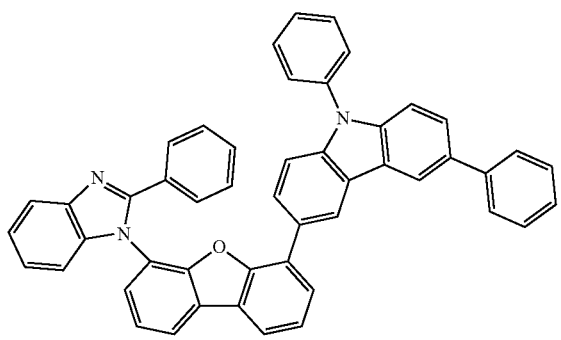
formula (A-13)
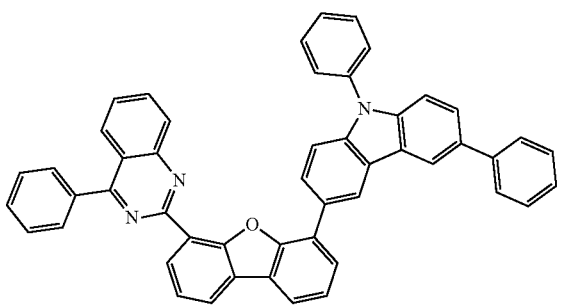
formula (A-14)
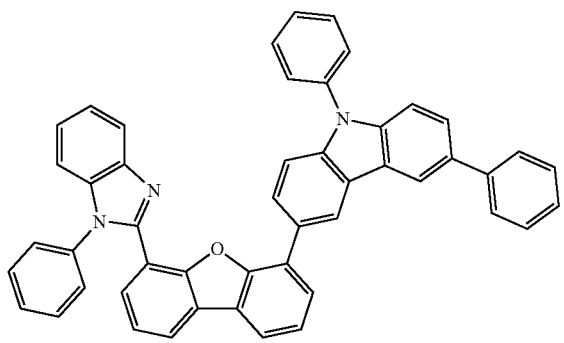
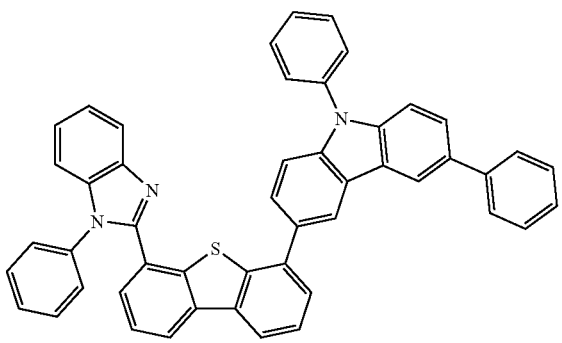

-continued
formula (A-15)
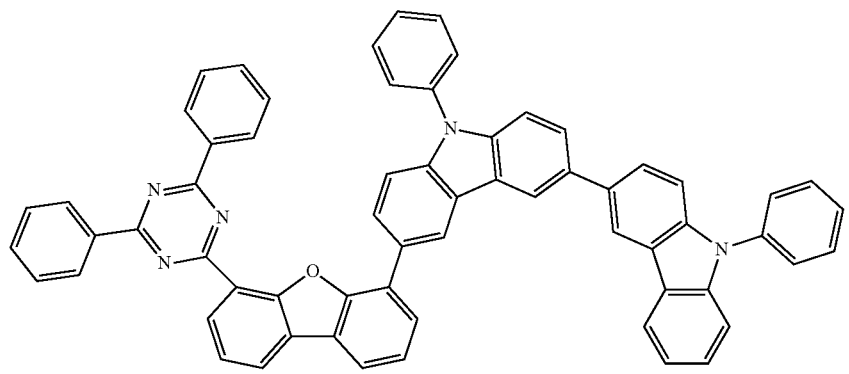
formula (A-16)
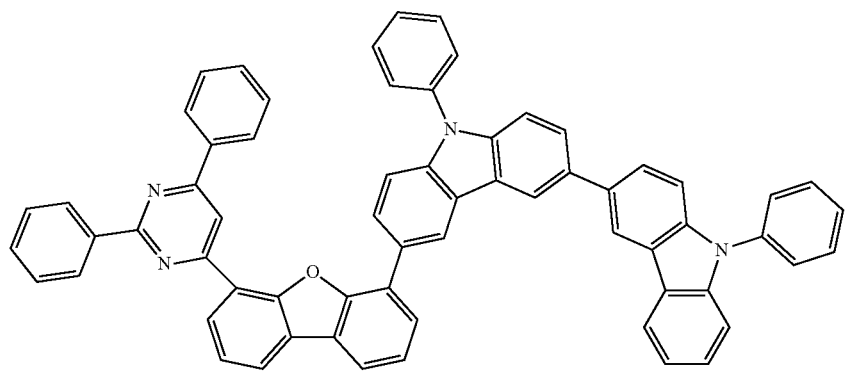
formula (A-17)
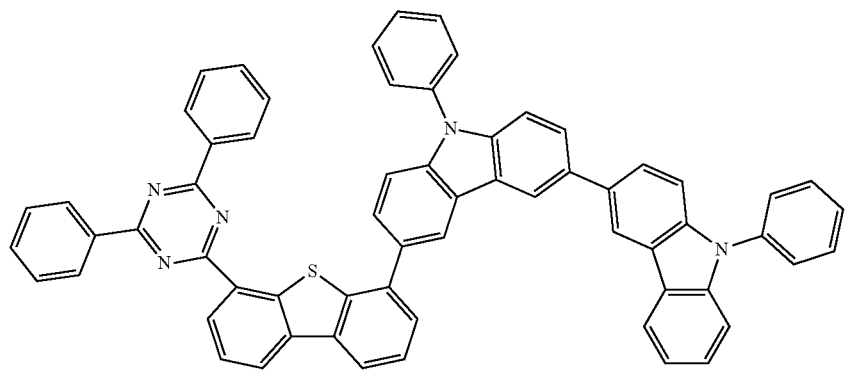
formula (A-18)
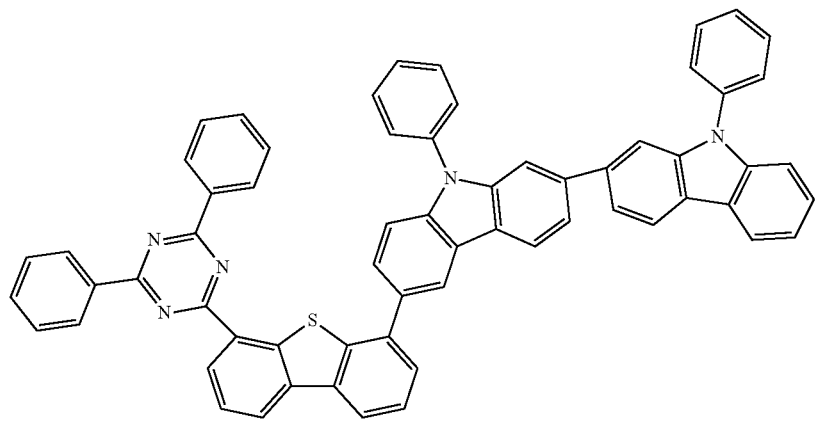

formula (A-19)
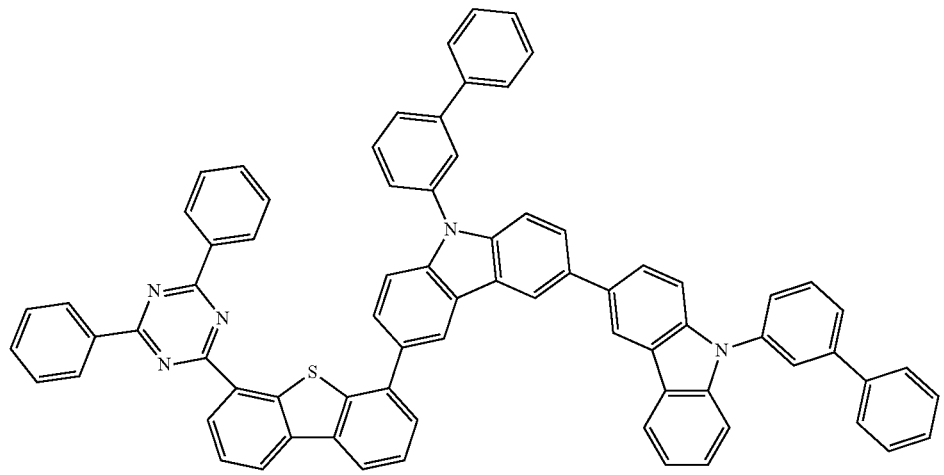
formula (A-20)
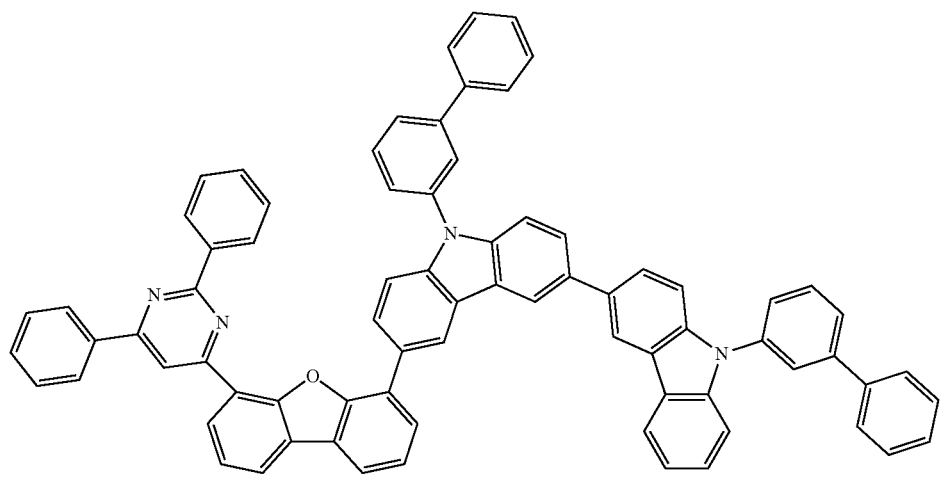
formula (A-21)
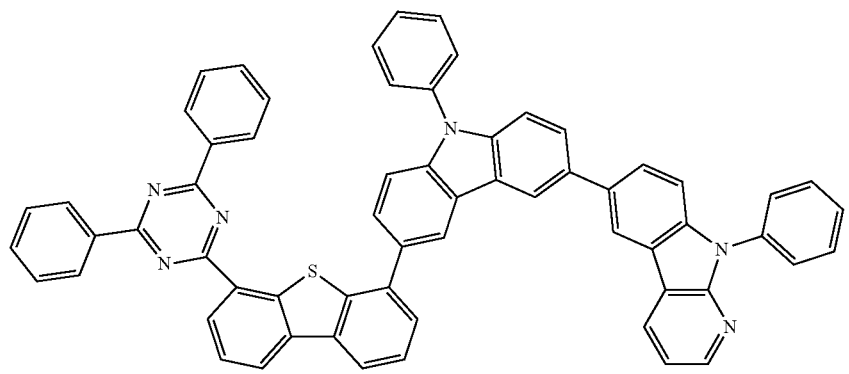

-continued
formula (A-22)
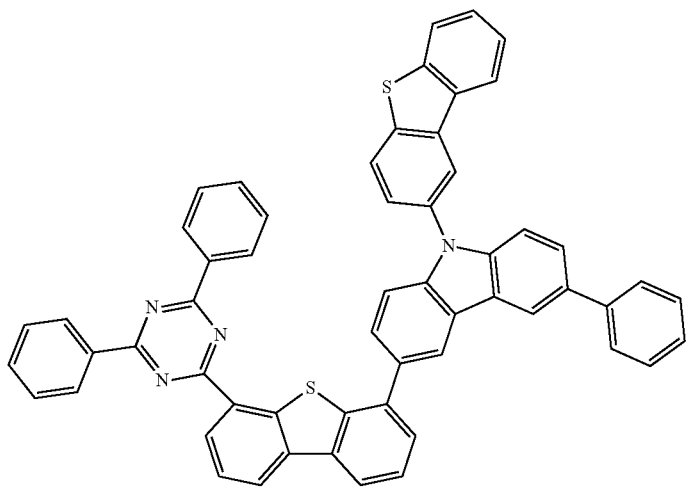
formula (A-23)
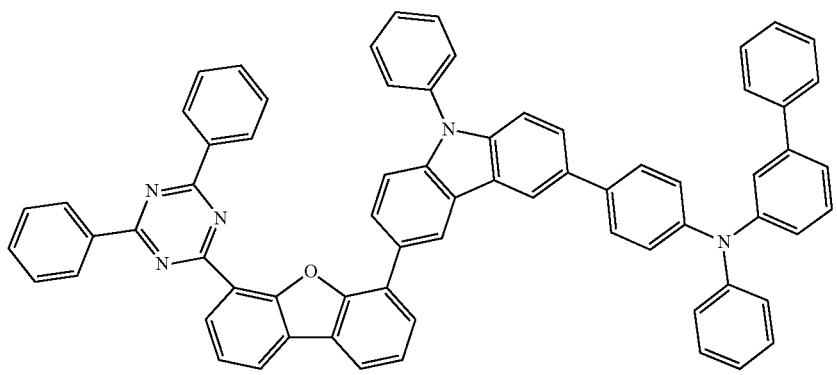
formula (A-24)
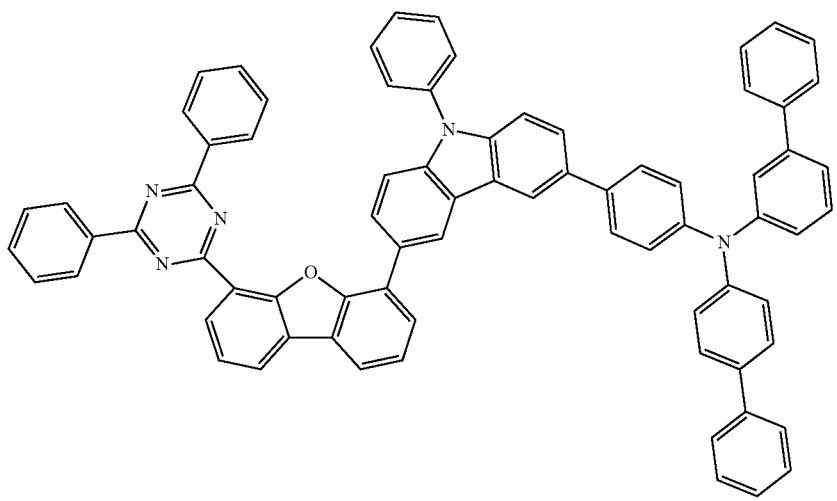

-continued
formula (A-25)
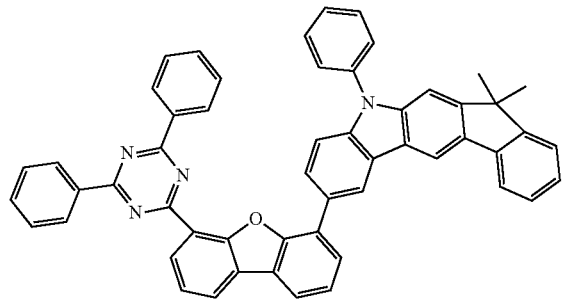
formula (A-26)
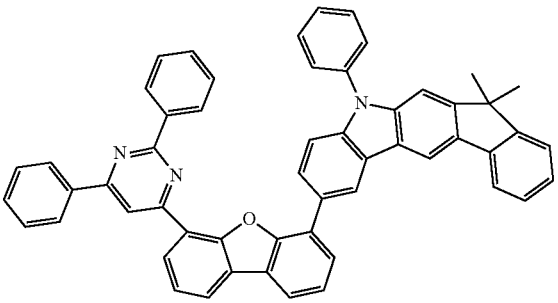
formula (A-27)
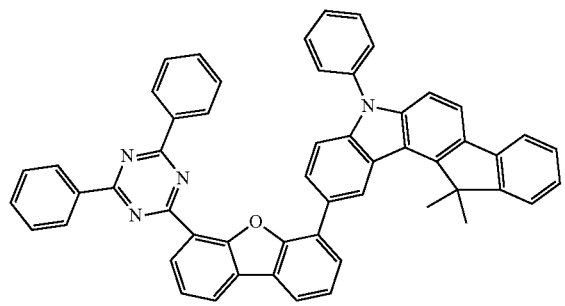
formula (A-28)
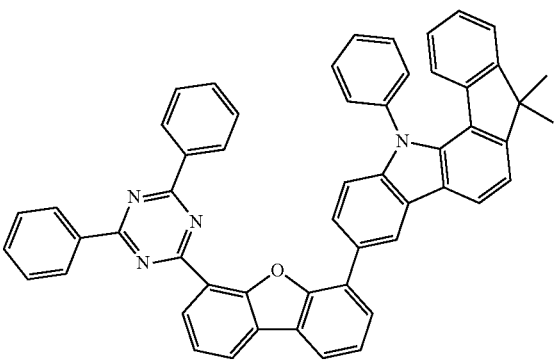
formula (A-29)
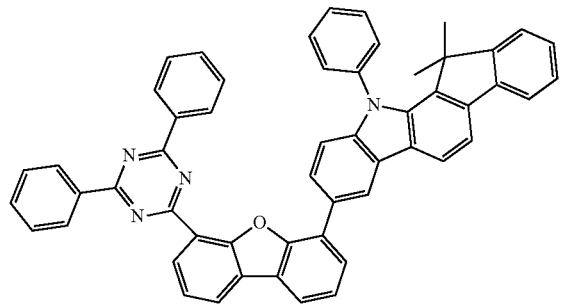
formula (A-30)
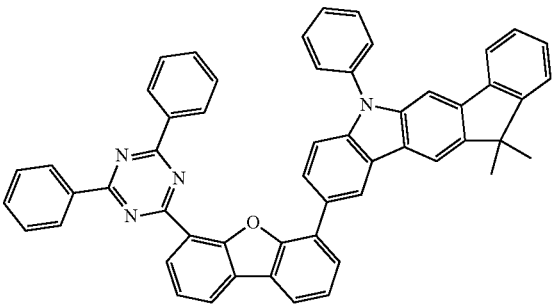
formula (A-31)
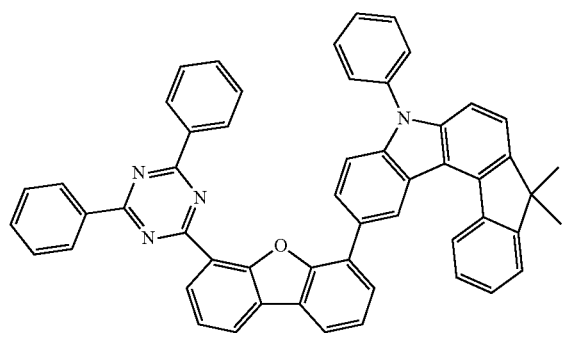
formula (A-32)
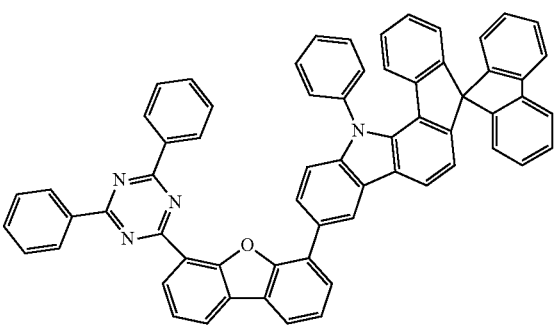

-continued
formula (A-33)
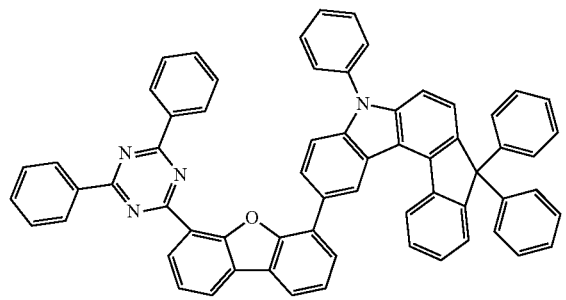
formula (A-34)
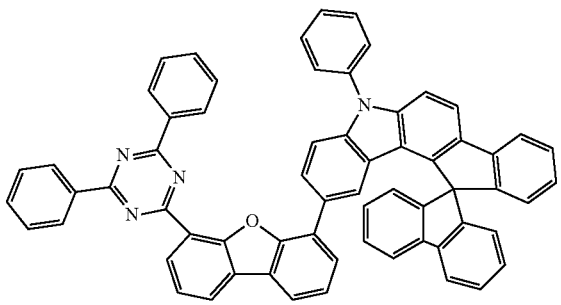
formula (A-35)
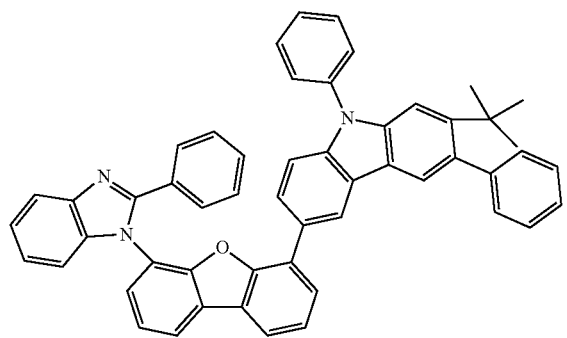
formula (A-36)
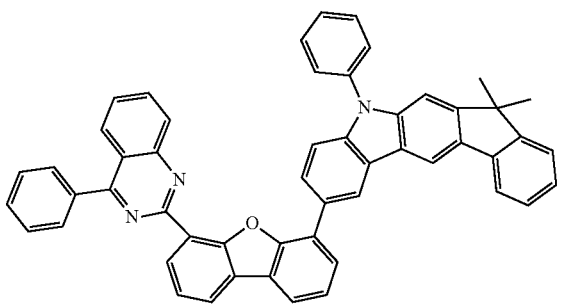
formula (A-37)
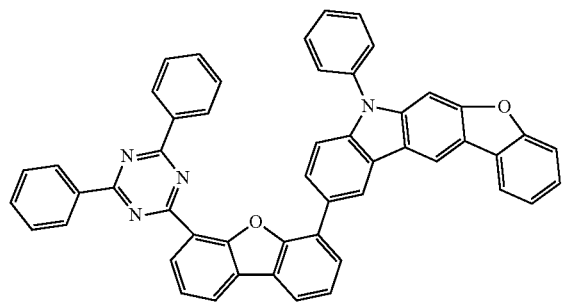
formula (A-38)
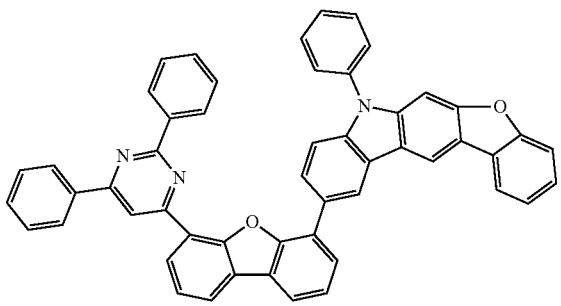
formula (A-39)
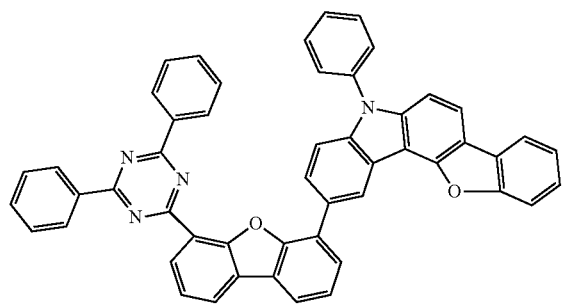
formula (A-40)
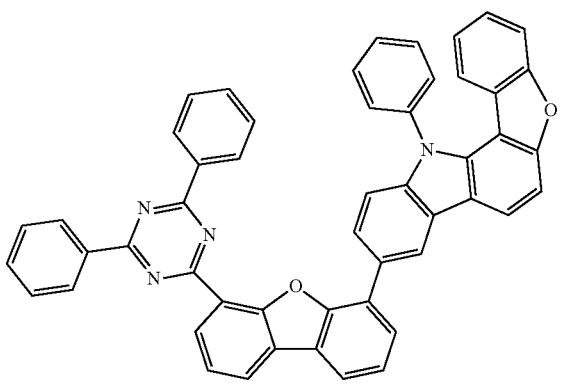

-continued
formula (A-41)
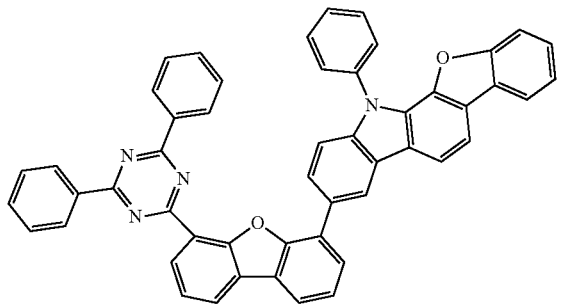
formula (A-42)
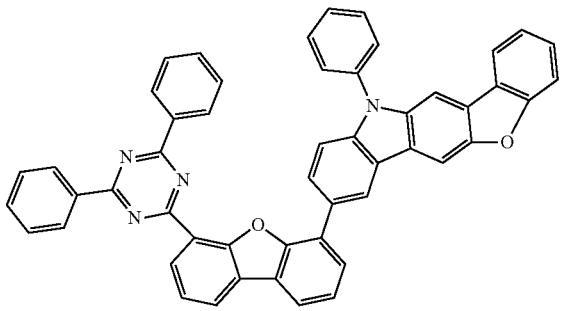
formula (A-43)
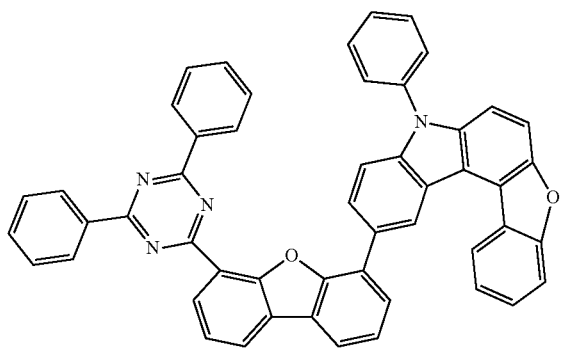
formula (A-44)
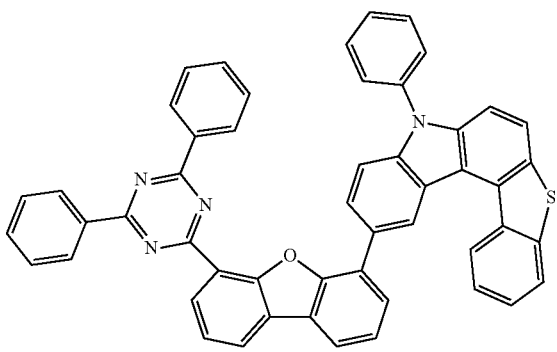
formula (A-45)
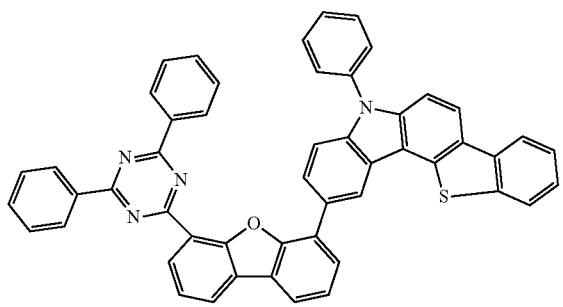
formula (A-46)
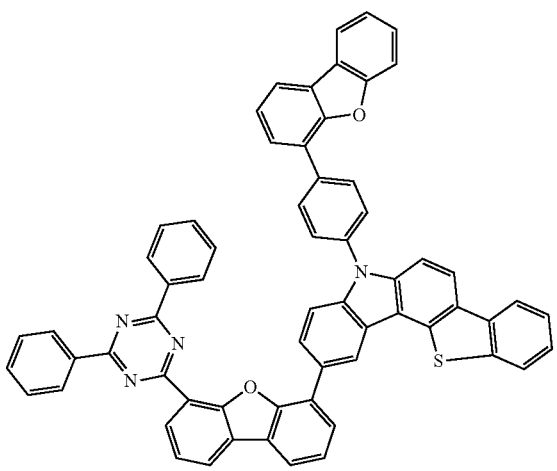
formula (A-47)
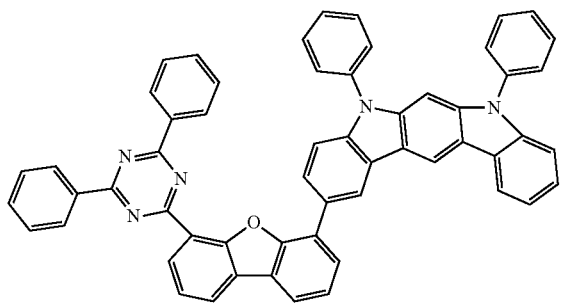
formula (A-48)
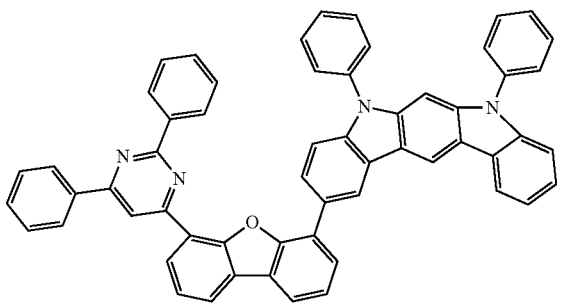

-continued
formula (A-49)
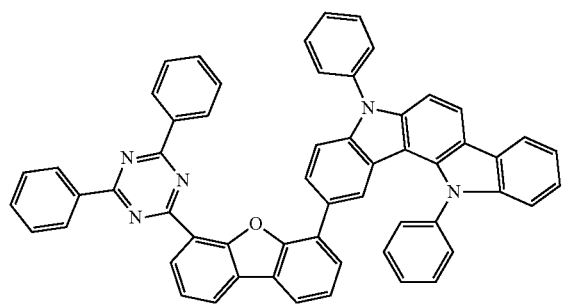
formula (A-50)
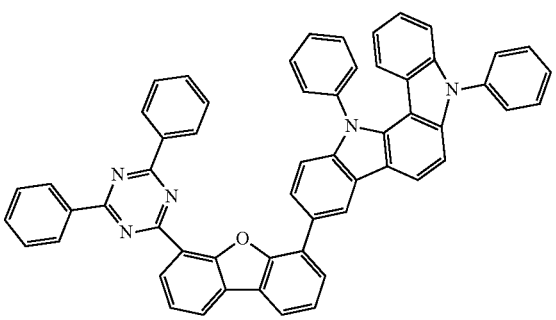
formula (A-51)
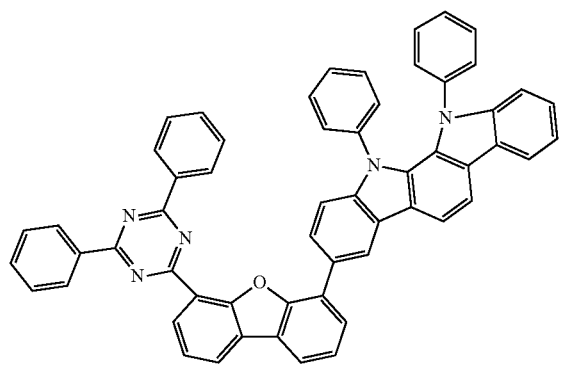
formula (A-52)
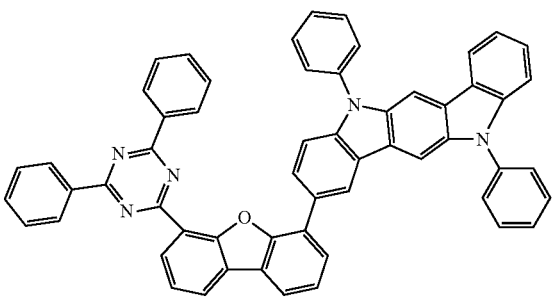
formula (A-53)
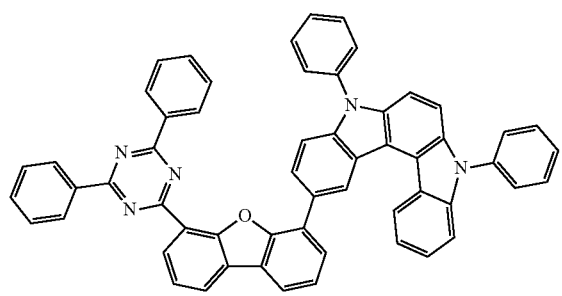
formula (A-54)
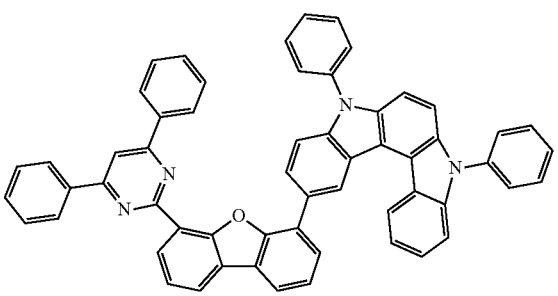
formula (A-55)
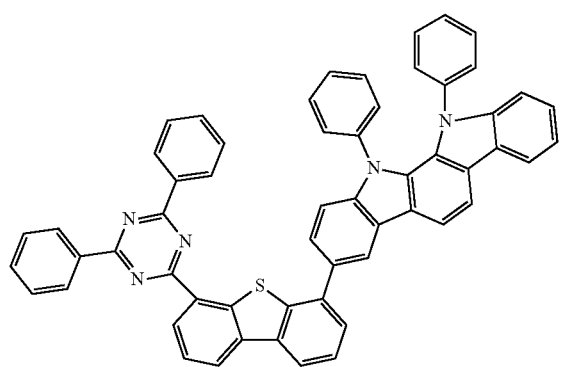
formula (A-56)
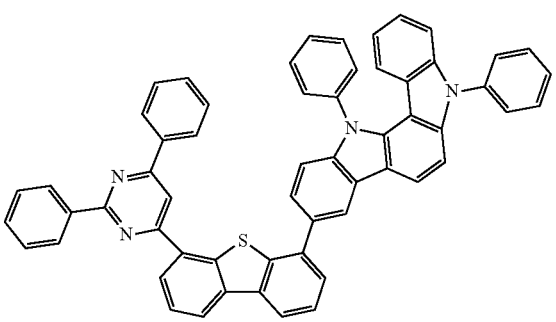

formula (A-57)
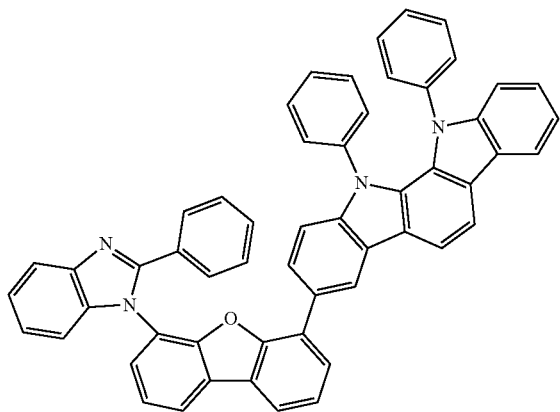
formula (A-58)
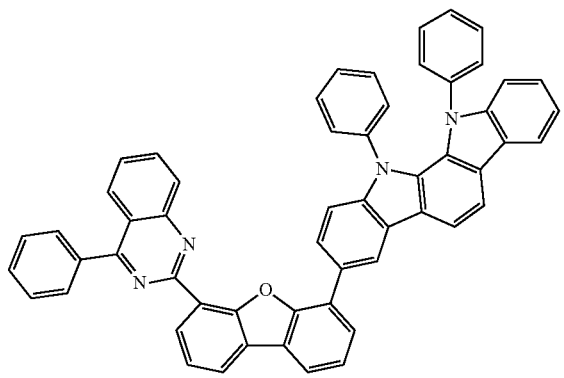
formula (A-59)
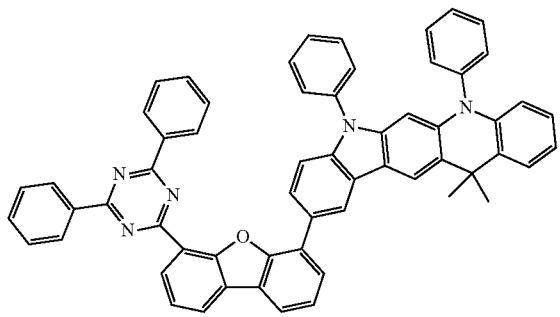
formula (A-60)
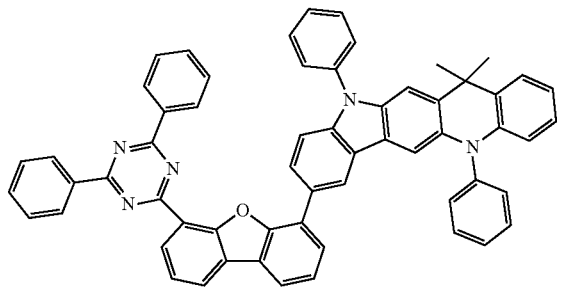
formula (A-61)
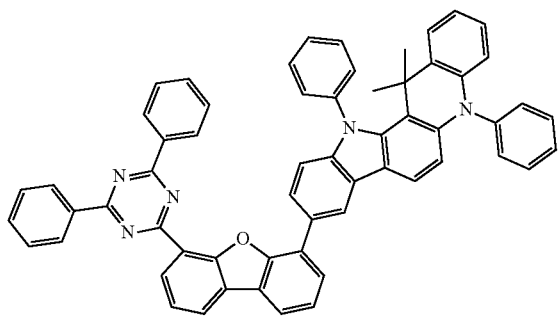
formula (A-62)
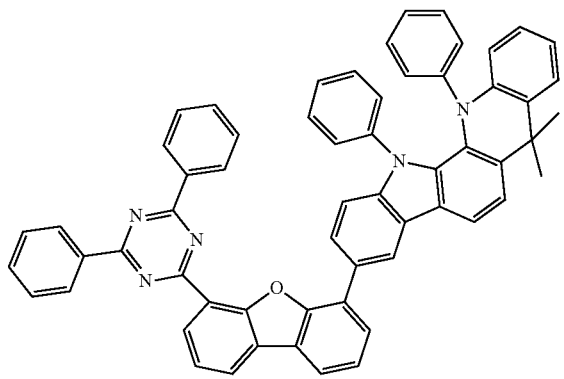
formula (A-63)
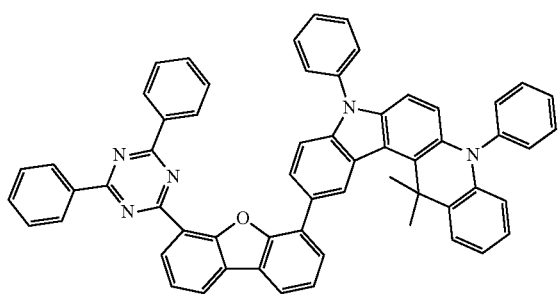
formula (A-64)
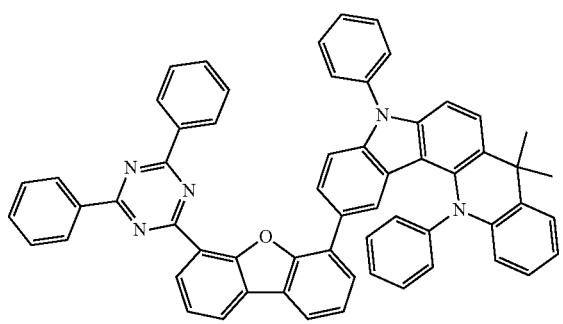

-continued
formula (A-65)
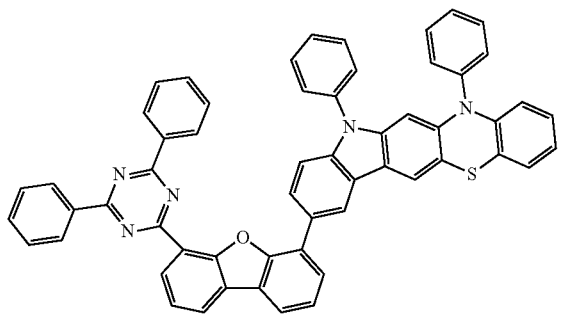
formula (A-66)
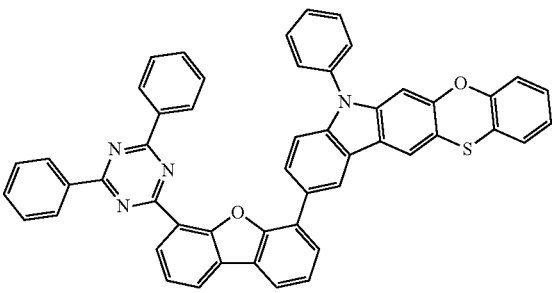
formula (A-67)
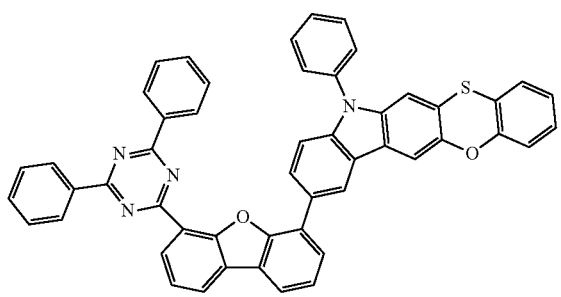
formula (A-68)
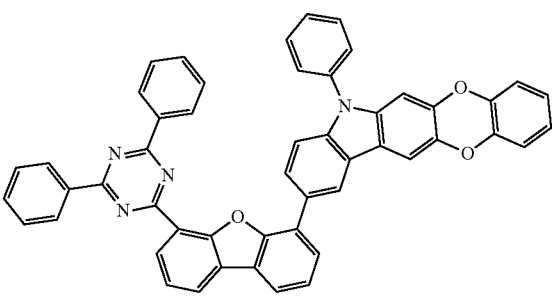
formula (A-69)
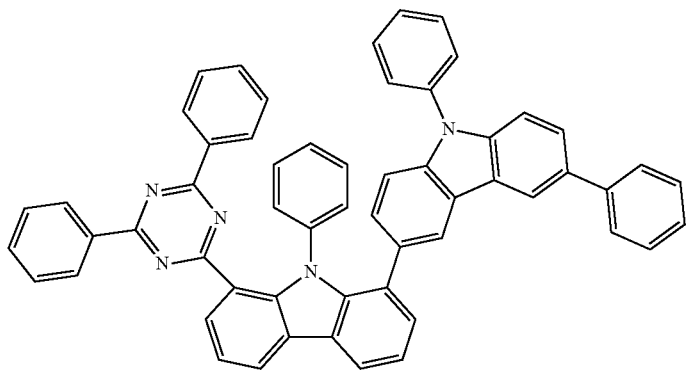
formula (A-70)
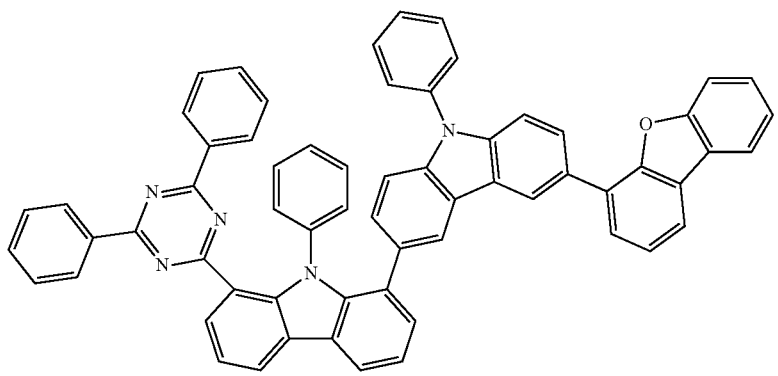

formula (A-71)
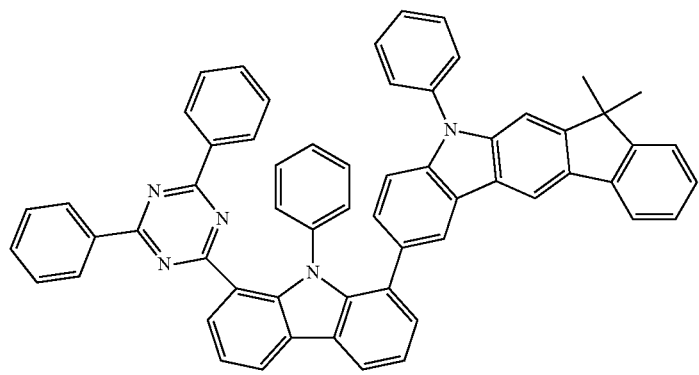
formula (A-72)
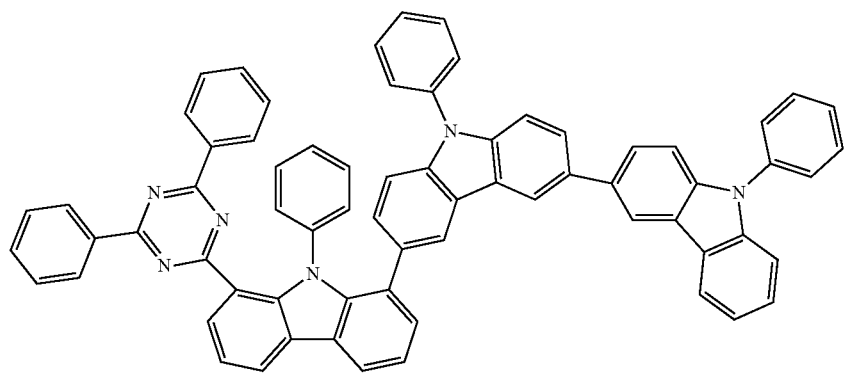
formula (A-73)
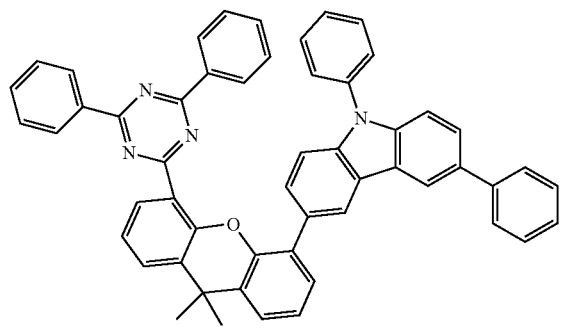
formula (A-74)
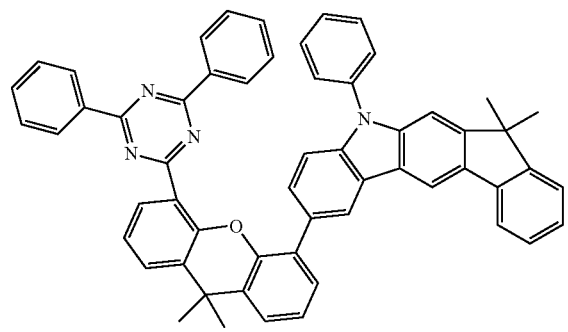
formula (A-75)
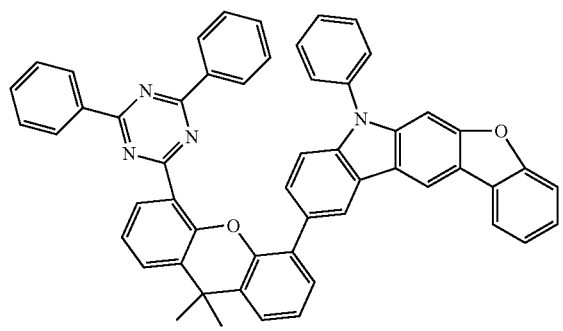
formula (A-76)
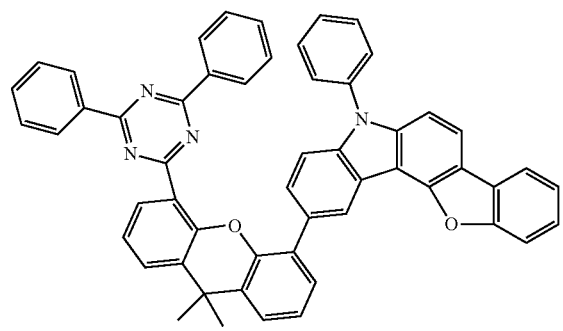

-continued
formula (A-77)
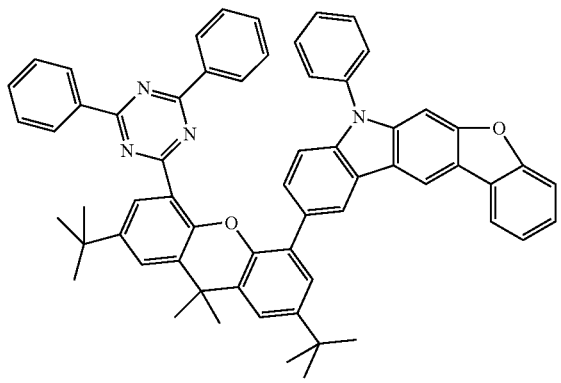
formula (A-78)
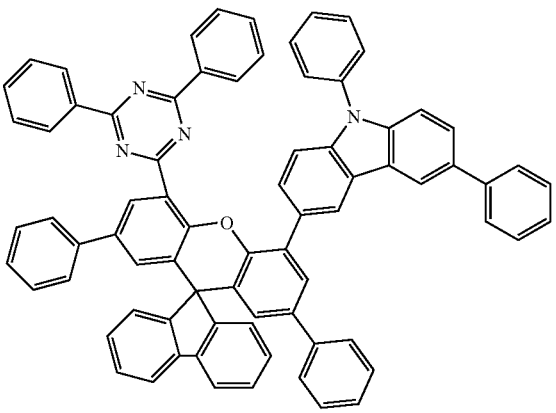
formula (A-79)
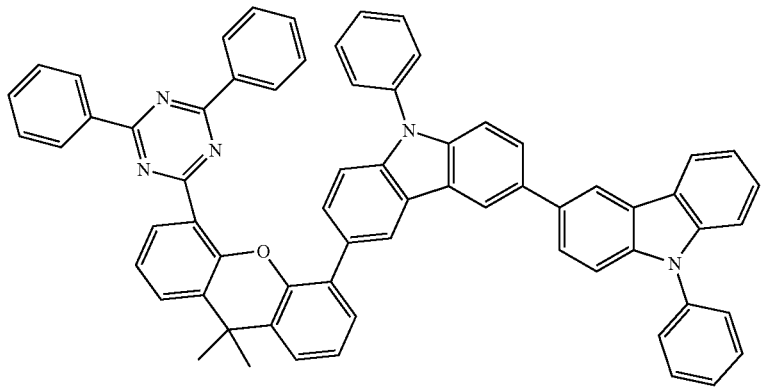
formula (A-80)
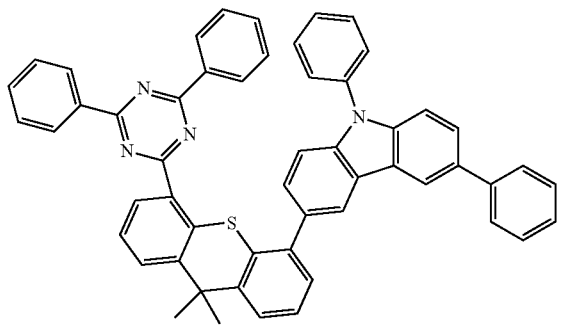
formula (A-81)
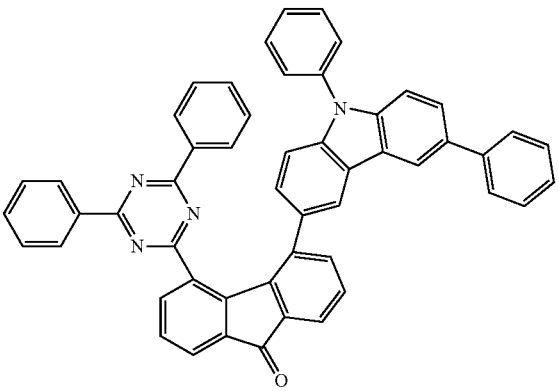
formula (A-82)
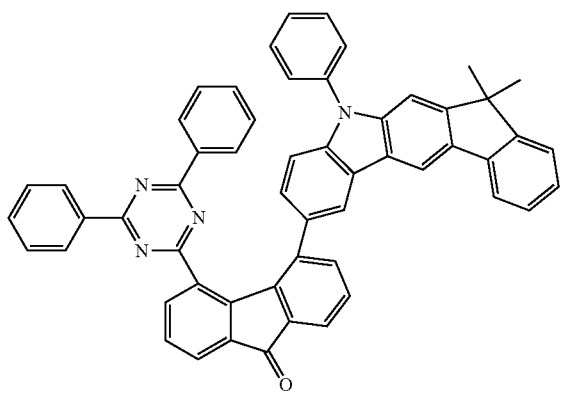
formula (A-83)
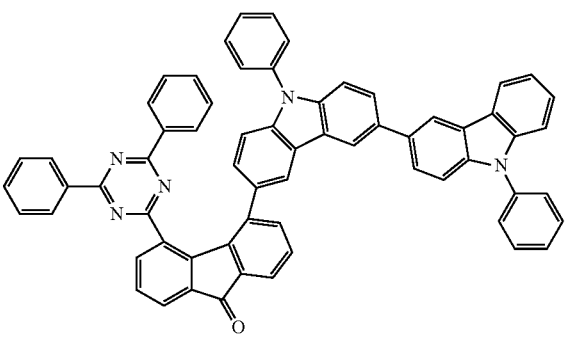

formula (A-84)
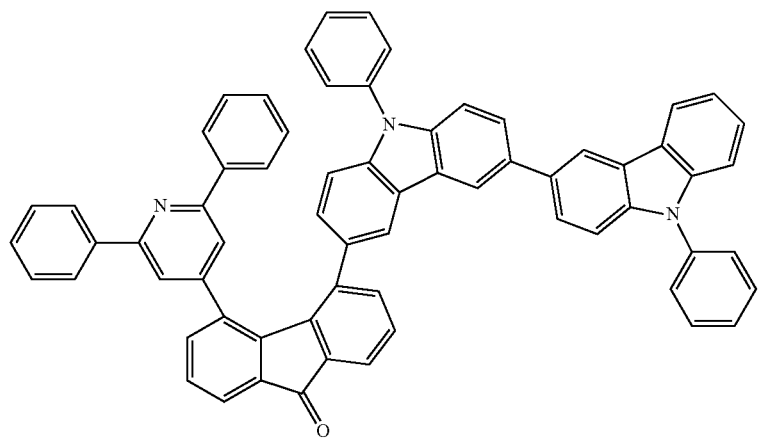
formula (A-85)
formula (A-86)
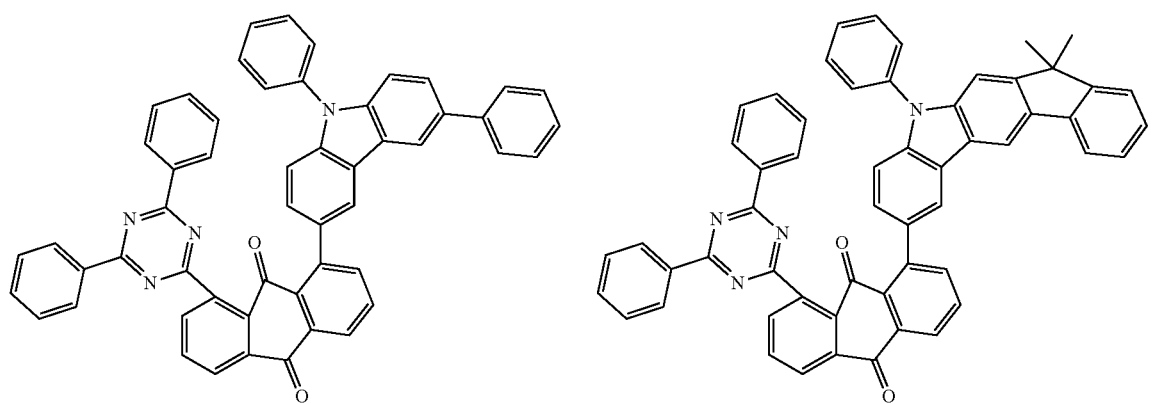
formula (A-87)
formula (A-88)
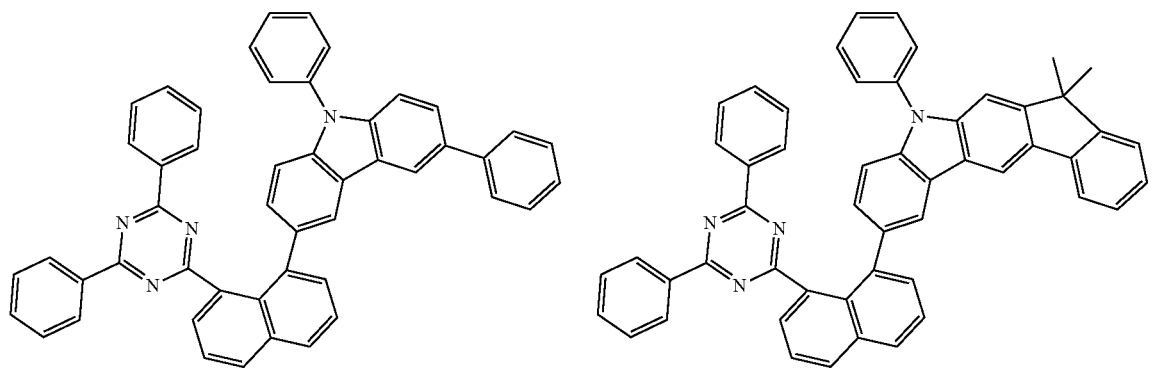

-continued
formula (A-89)
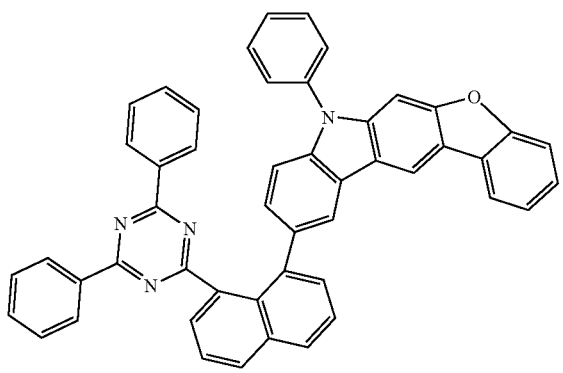
formula (A-90)
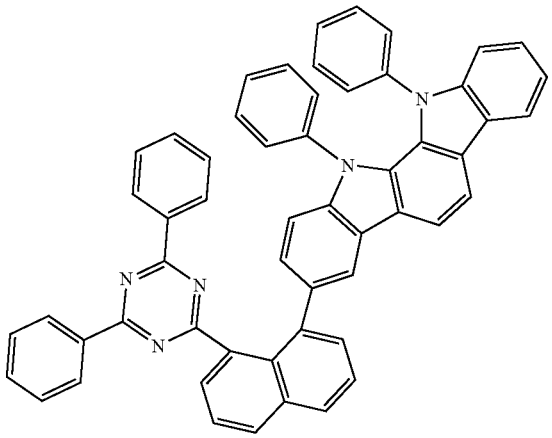
formula (A-91)
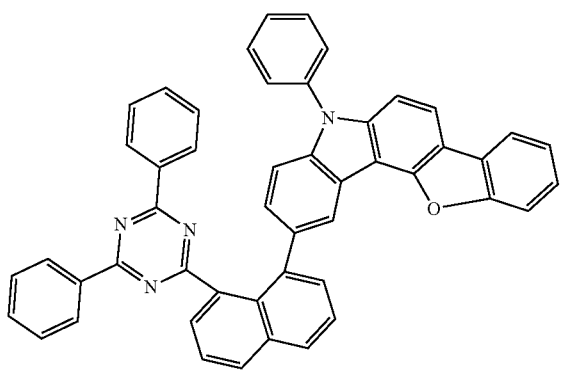
formula (A-92)
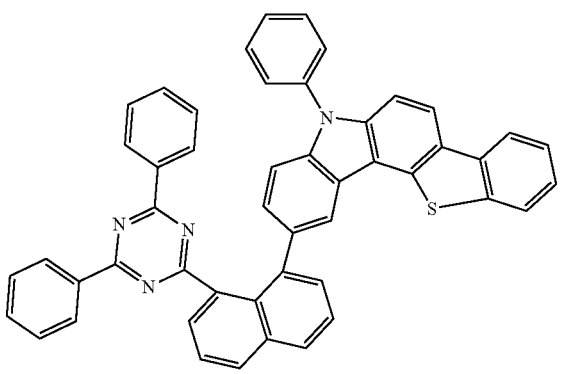
formula (A-93)
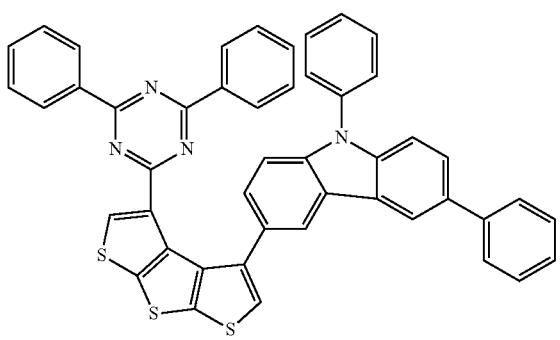
formula (A-94)
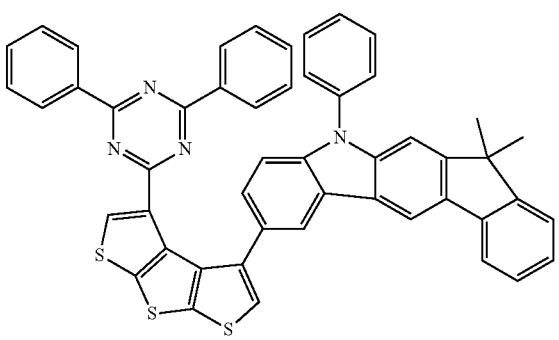
formula (A-95)
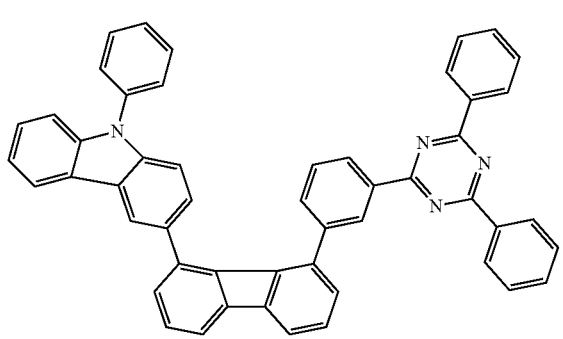

formula (A-96)
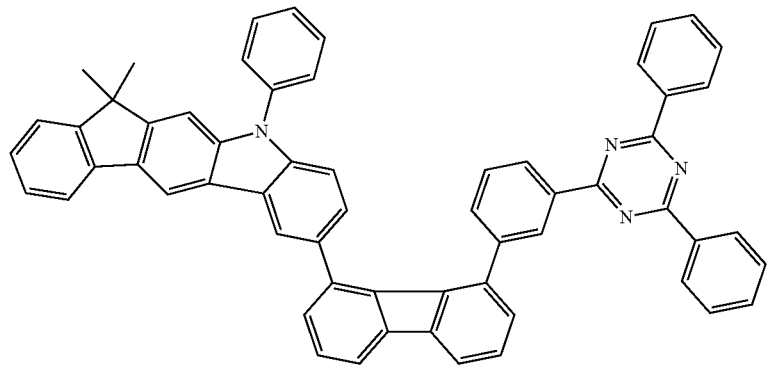
formula (A-97)　　　　　formula (A-98)
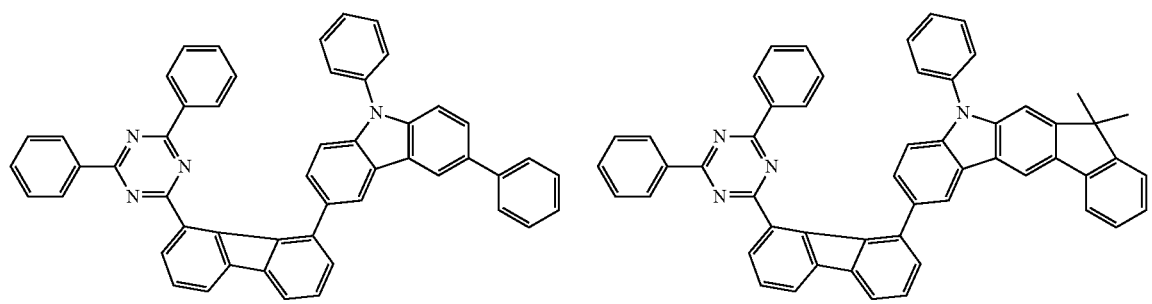
formula (A-99)　　　　　formula (A-100)
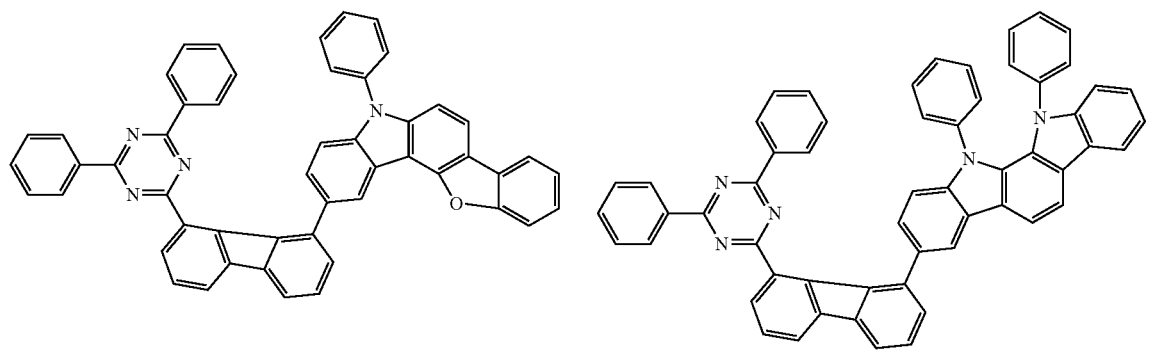
formula (A-101)　　　　　formula (A-102)
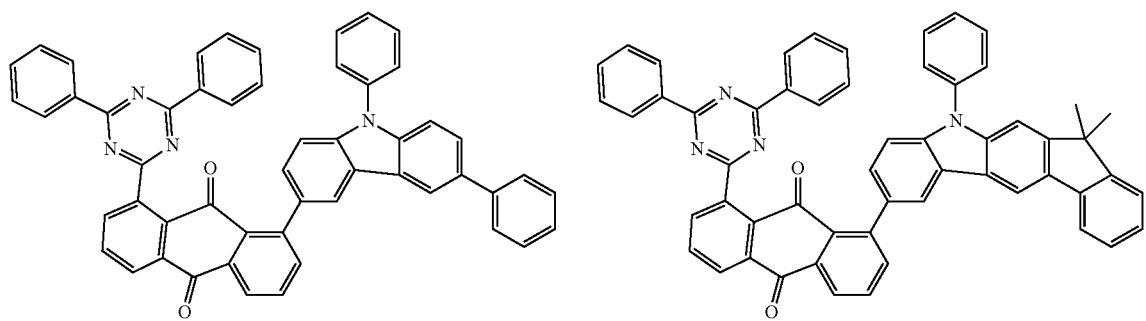

-continued formula (A-103)
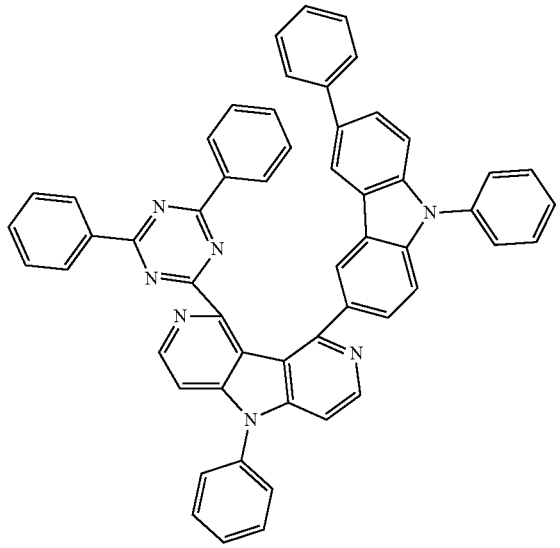

formula (A-104)
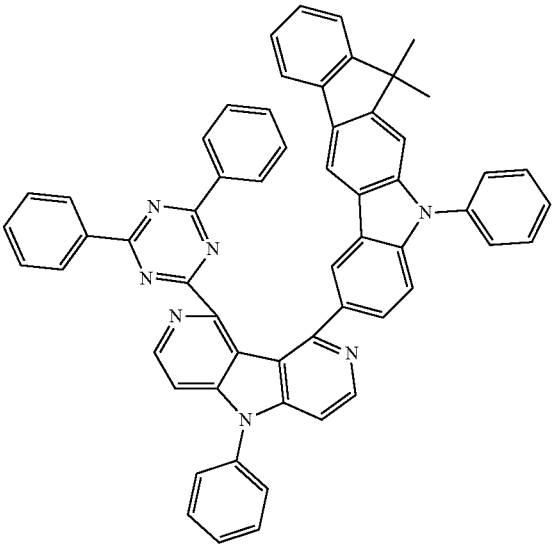

formula (A-105)
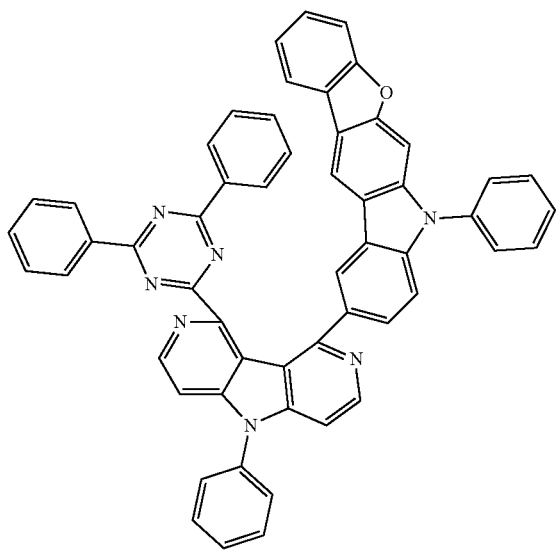

formula (A-106)
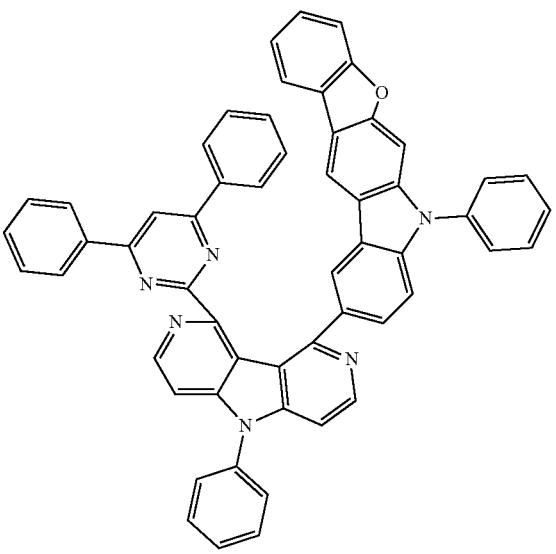

The invention furthermore relates to the use of a compound of the formula (1) in an electronic device, preferably in an electron-transporting layer and/or in an emitting layer.

The electronic device according to the invention is preferably selected from organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs, LECs or LEECs), organic laser diodes (O-lasers) and organic light-emitting diodes (OLEDs). Particular preference is given to organic electroluminescent devices, very particularly preferably OLECs and OLEDs and in especially preferably OLEDs.

The organic layer comprising the compound of the formula (1) is preferably a layer having an electron-transporting function. It is particularly preferably an electron-injection layer, an electron-transport layer, a hole-blocking layer or an emitting layer.

In a further very particularly preferred embodiment, the compound of the general formula (1) is employed in an emitting layer, in particular as matrix material.

A hole-transport layer in accordance with the present application is a layer having a hole-transporting function which is located between the anode and the emitting layer.

An electron-ransport layer in accordance with the present application is a layer having an electron-transporting function which is located between the cathode and the emitting layer.

Hole-injection layers and electron-blocking layers in the sense of the present application are taken to be special embodiments of hole-transport layers. In the case of a plurality of hole-transport layers between anode and emitting layer, a hole-injection layer is a hole-transport layer which is directly adjacent to the anode or is only separated therefrom by a single coating of the anode. In the case of a plurality of hole-transport layers between anode and emitting layer, an electron-blocking layer is the hole-transport layer which is directly adjacent to the emitting layer on the anode side.

As already mentioned above, the compound of the formula (1) is, in a preferred embodiment, employed as matrix material in an emission layer of an organic electronic device, in particular in an organic electroluminescent device, for example in an OLED or OLEC. The matrix material of the formula (1) is present in the electronic device here in combination with one or more dopants, preferably phosphorescent dopants.

The term phosphorescent dopants typically encompasses compounds in which the light emission takes place through a spin-forbidden transition, for example a transition from an excited triplet state or a state having a relatively high spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present application. Examples of phosphorescent dopants are given in a following section.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the larger.

The proportion of the matrix material in the emitting layer in this case is between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the formula (1) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

The present invention furthermore relates to a composition comprising at least one compound of the formula (1) and at least one further organic semiconductor material selected from the group consisting of fluorescent emitters, phosphorescent emitters, host materials, matrix materials, electron-transport materials, electron-injection materials, hole-conductor materials, hole-injection materials, electron-blocking materials, hole-blocking materials, n-dopants and p-dopants.

n-dopants herein are taken to mean reducing agents, i.e. electron donors. Preferred examples of n-dopants are $W(hpp)_4$ and further electron-rich metal complexes in accordance with WO 2005/086251 A2, P=N compounds (for example WO 2012/175535 A1, WO 2012/175219 A1), naphthylenecarbodiimides (for example WO 2012/168358 A1), fluorenes (for example WO 2012/031735 A1), free radicals and diradicals (for example EP 1837926 A1, WO 2007/107306 A1), pyridines (for example EP 2452946 A1, EP 2463927 A1), N-heterocyclic compounds (for example WO 2009/000237 A1) and acridines, as well as phenazines (for example US 2007/145355 A1).

p-Dopants herein are taken to mean oxidants, i.e. electron acceptors. Preferred examples of p-dopants are F4-TCNQ, Fe-TNAP, NDP-2 (Novaled), NDP-9 (Novaled), quinones (for example EP 1538684 A1, WO 2006/081780 A1, WO 2009/003455 A1, WO 2010/097433 A1), radialenes (for example EP 1988587 A1, US 2010/102709 A1, EP 2180029 A1, WO 2011/131185 A1, WO 2011134458 A1, US 2012/223296 A1), S-containing transition-metal complexes (for example WO 2007/134873 A1, WO 2008/061517 A2, WO 2008/061518 A2, DE 102008051737 A1, WO 2009/089821 A1, US 2010/096600 A1), bisimidazoles (for example WO 2008/138580 A1), phthalocyanines (for example WO 2008/058525 A2), boratetraazapentalenes (for example WO 2007/115540 A1) fullerenes (for example DE 102010046040 A1) and main-group halides (for example WO 2008/128519 A2).

The present invention also relates to a composition comprising at least one compound of the formula (1) and at least one further matrix material.

The present invention also relates to a composition comprising at least one compound of the formula (1) and at least one wide band gap material, where a wide band gap material is taken to mean a material in the sense of the disclosure of U.S. Pat. No. 7,294,849. These systems exhibit particularly advantageous performance data in electroluminescent devices.

The present invention also relates to a composition comprising at least one compound of the formula (1) and at least one further matrix material and at least one phosphorescent emitter.

The present invention also relates to a composition comprising at least one compound of the formula (1) and at least one wide band gap material and at least one phosphorescent emitter.

Preferred phosphorescent dopants for use in mixed-matrix systems are the preferred phosphorescent dopants indicated below.

Examples of phosphorescent dopants are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention.

Explicit examples of phosphorescent dopants are shown in the following table

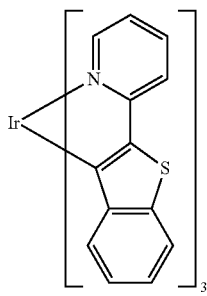

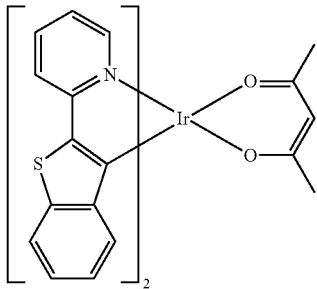

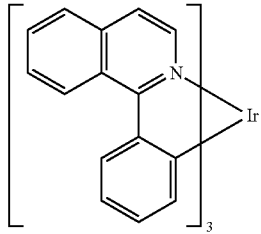

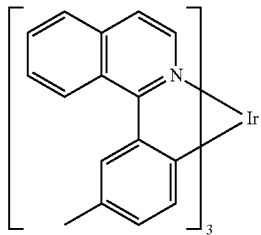

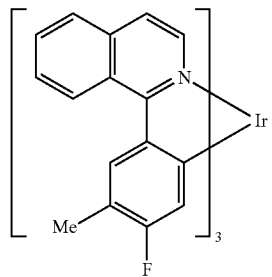

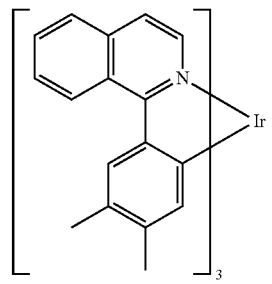

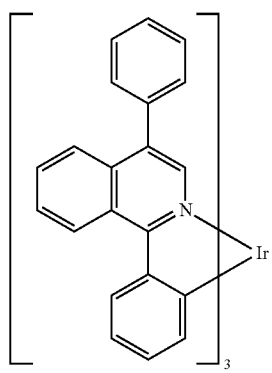

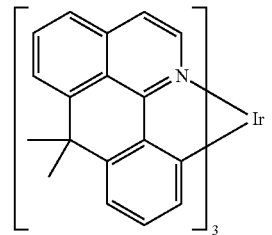

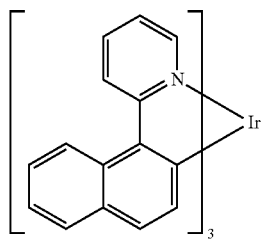
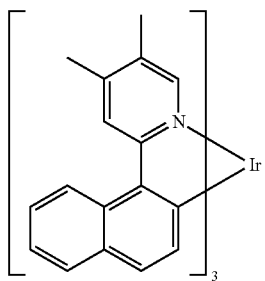
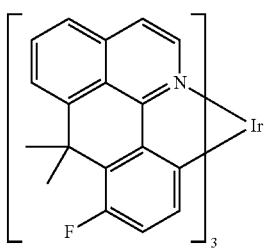
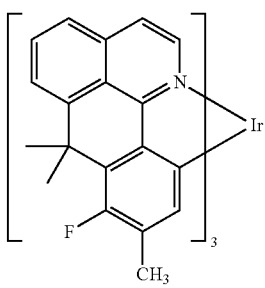
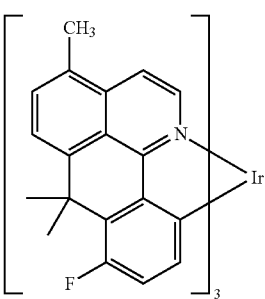
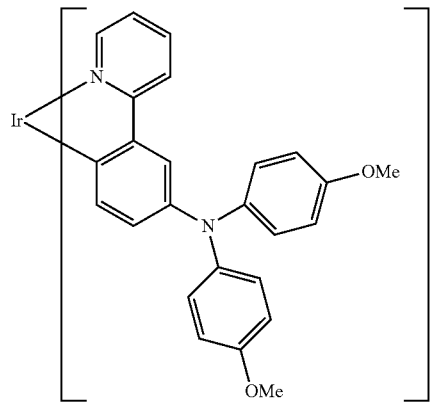
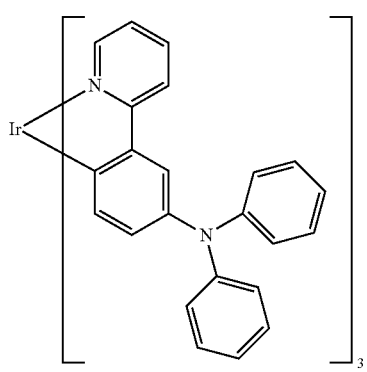
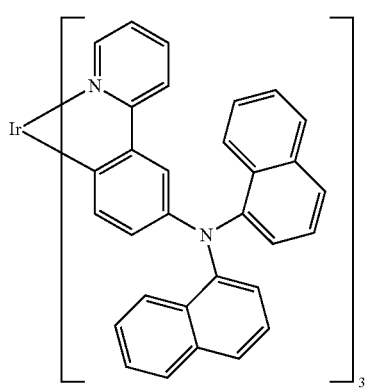
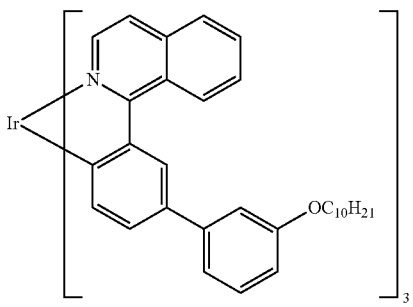

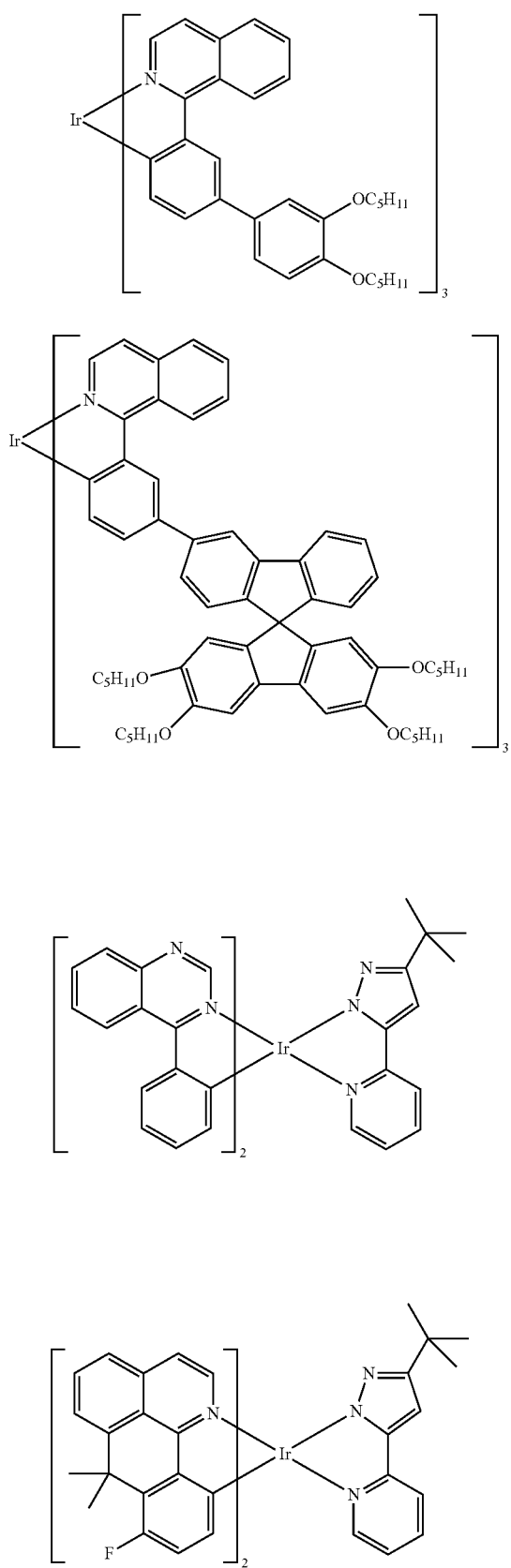
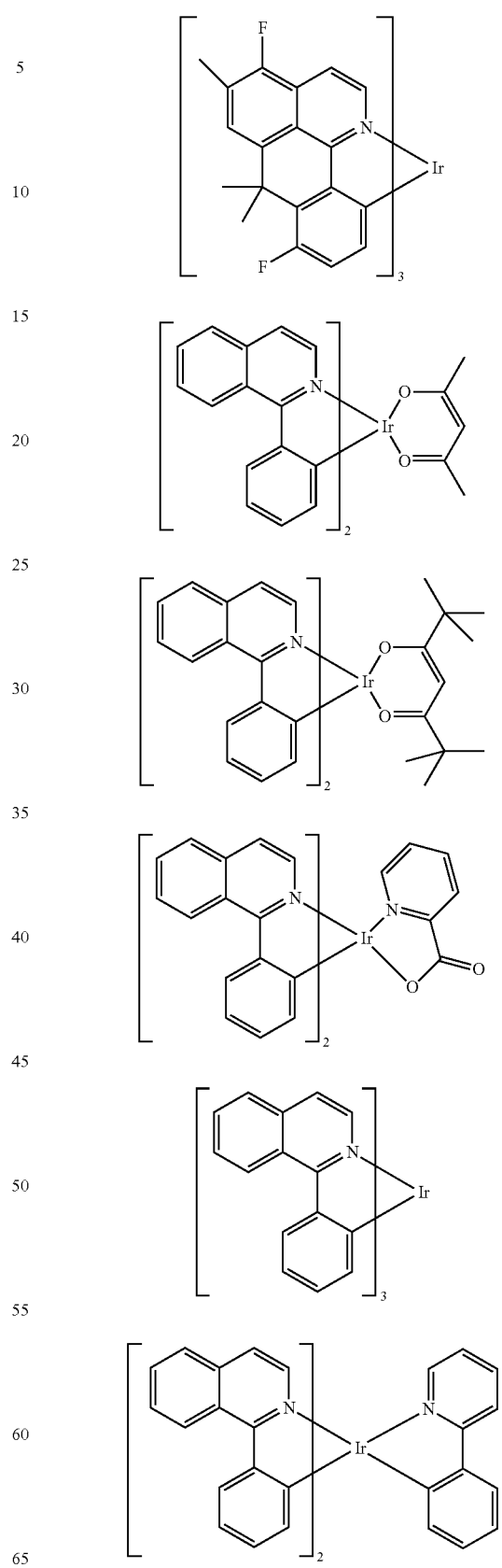

77
-continued
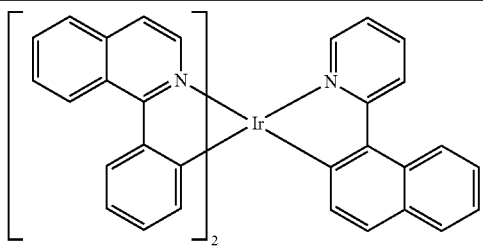
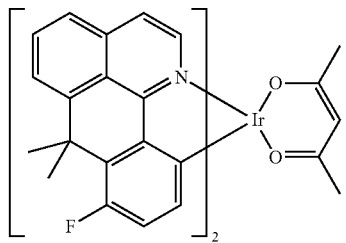
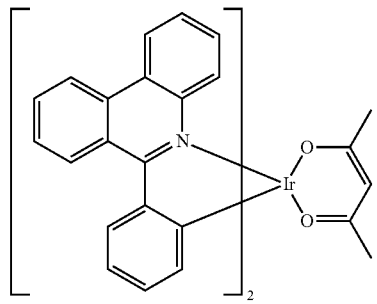
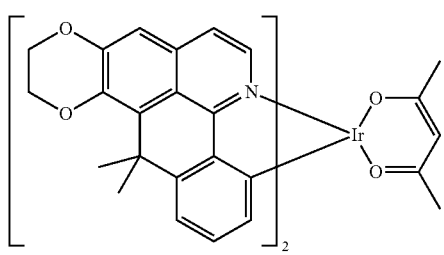
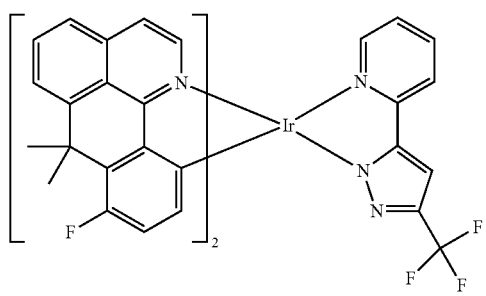
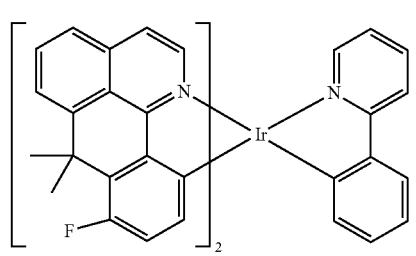
78
-continued
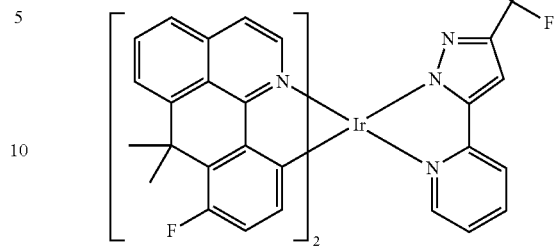
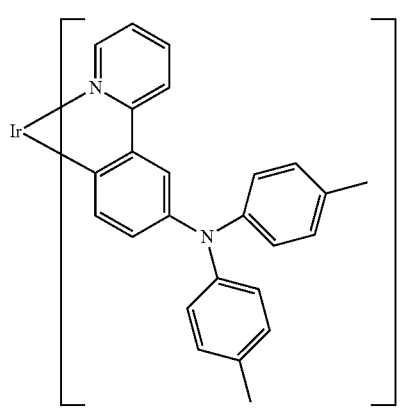
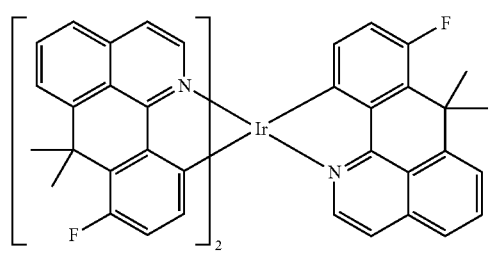
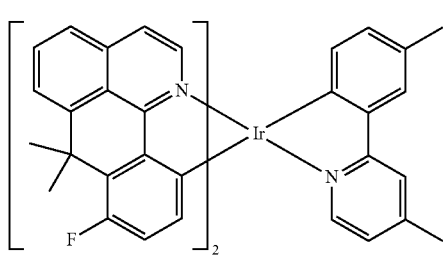
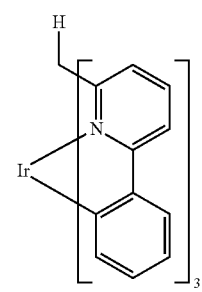

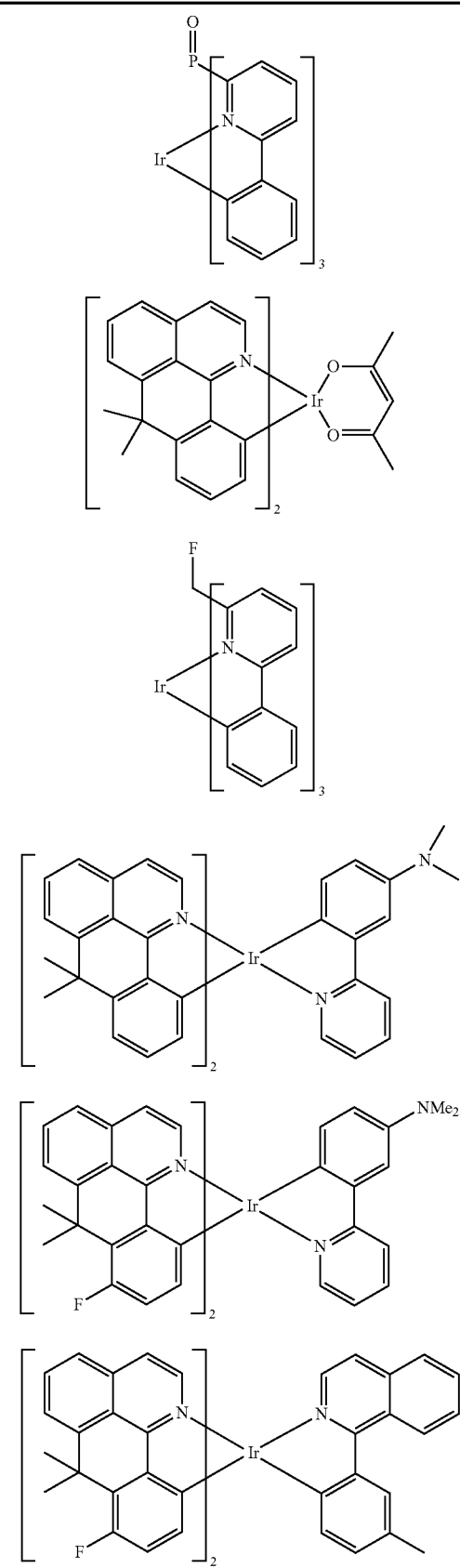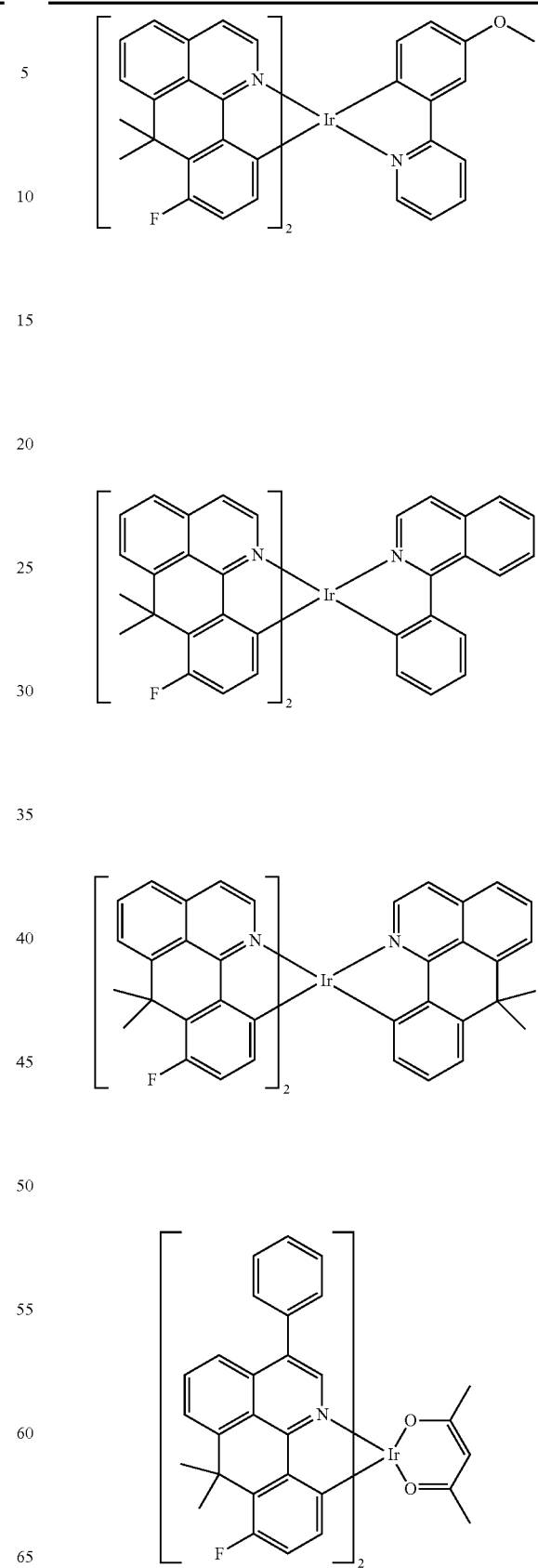

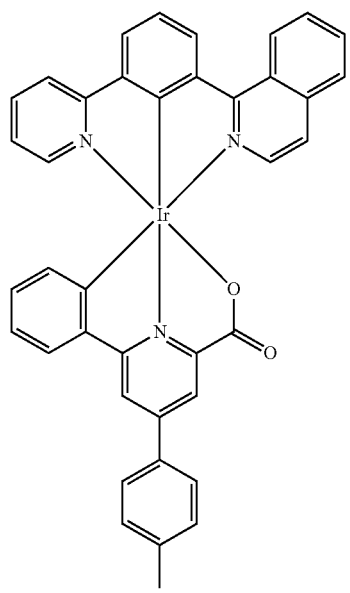
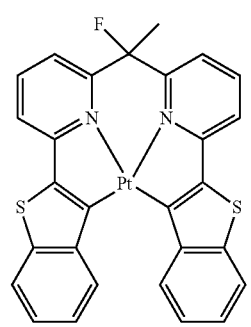
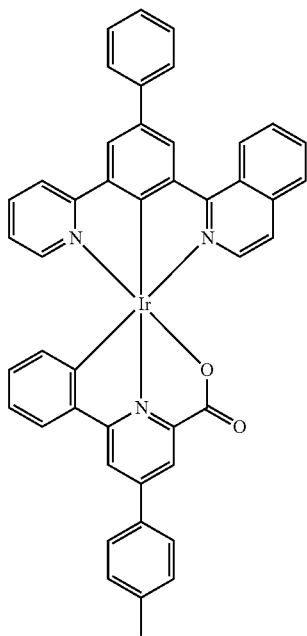
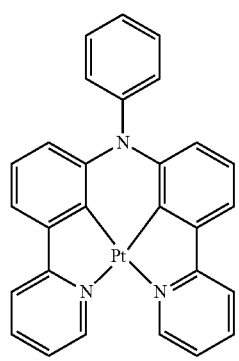
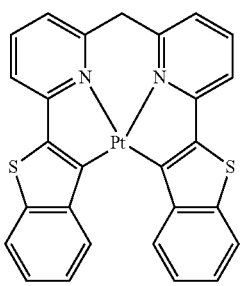
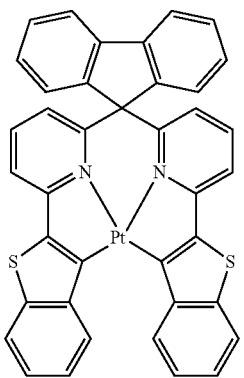
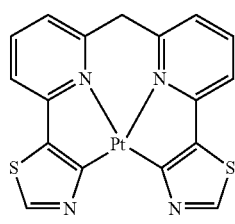

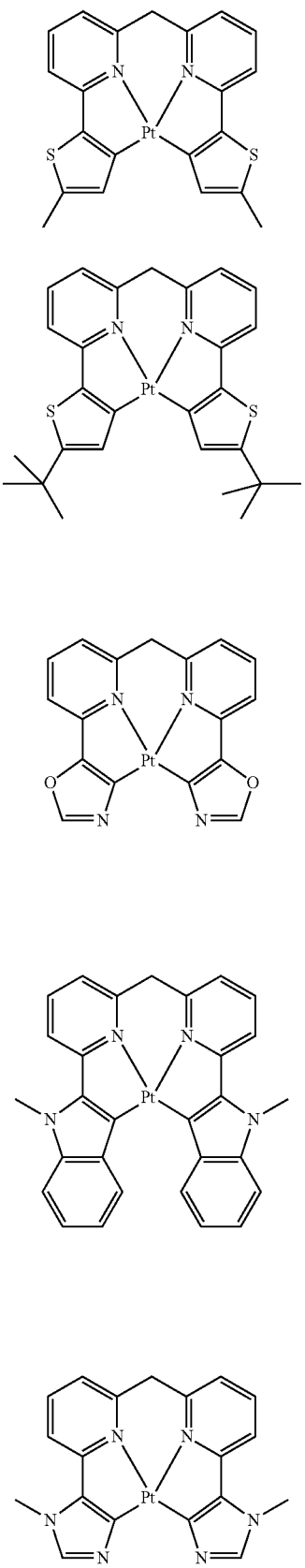
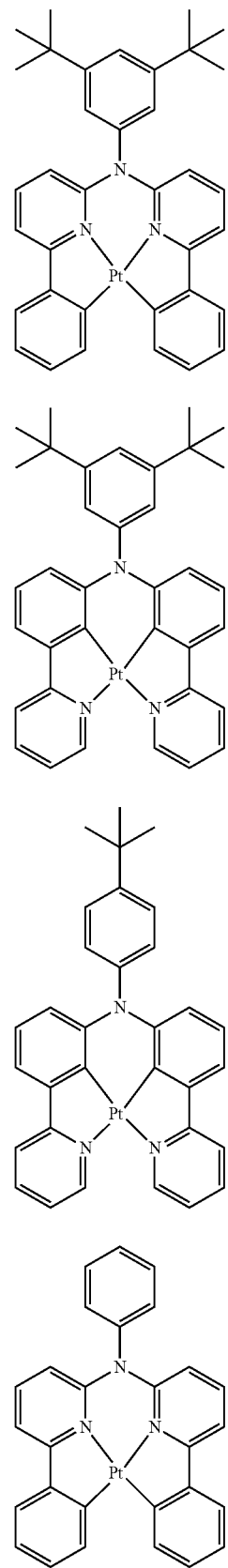

85
-continued
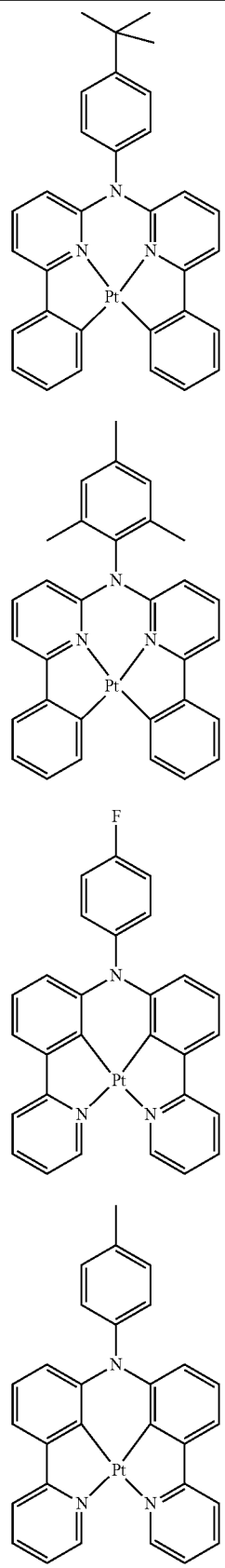
86
-continued
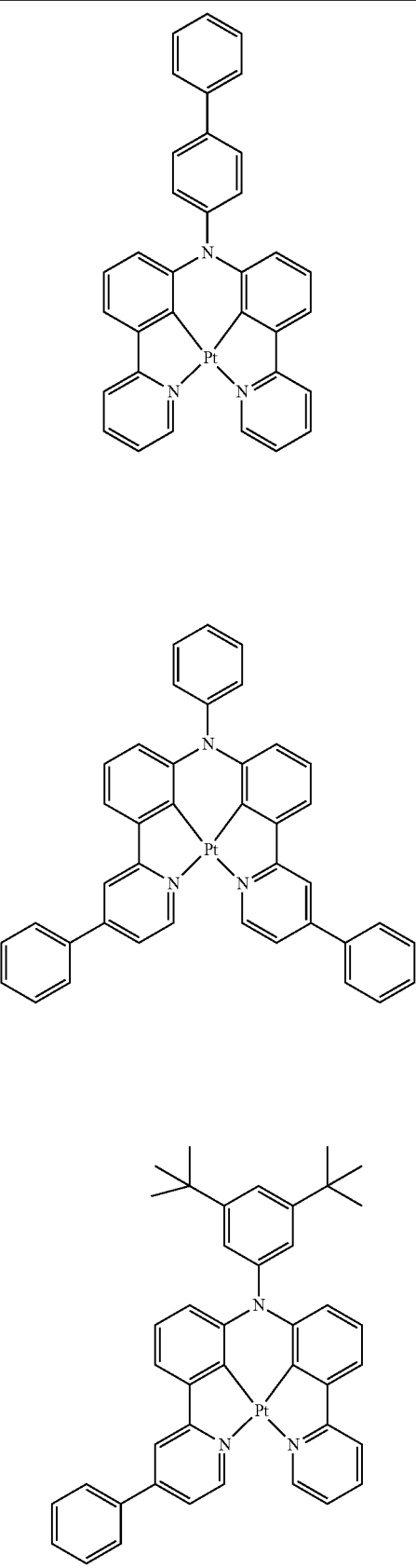

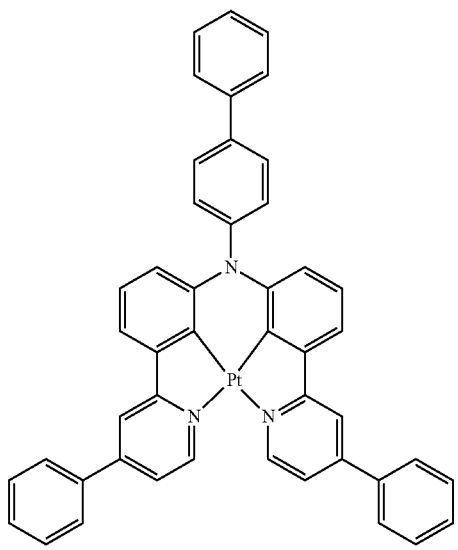
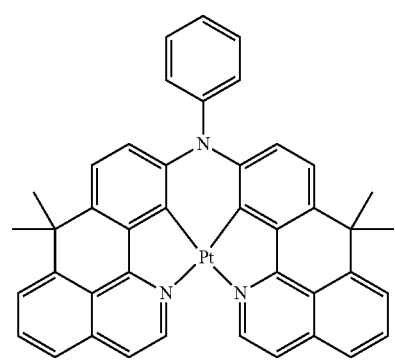
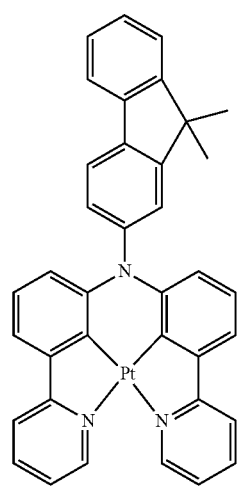
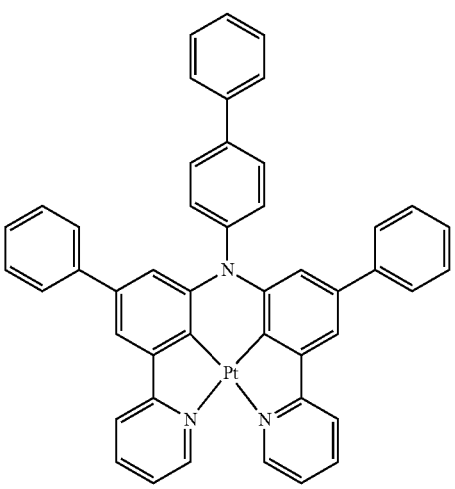
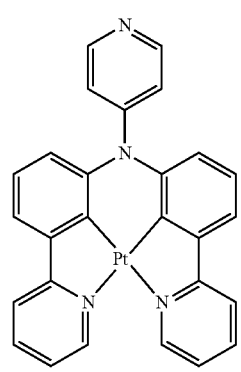
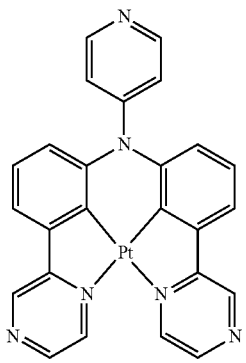
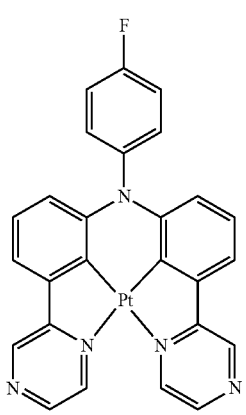

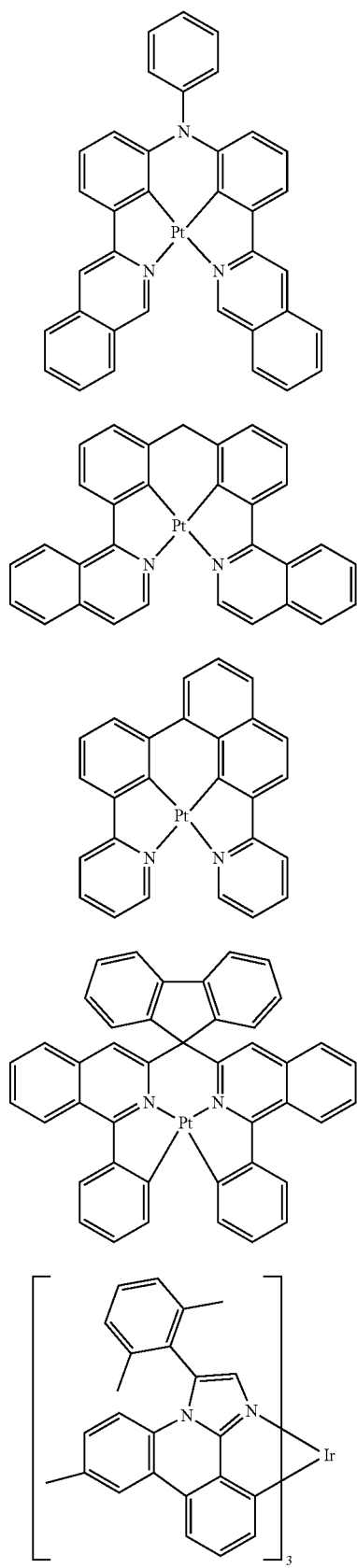

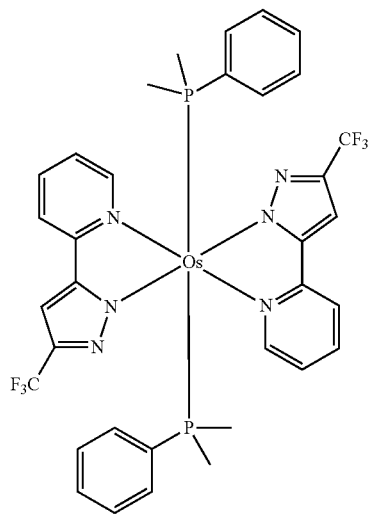
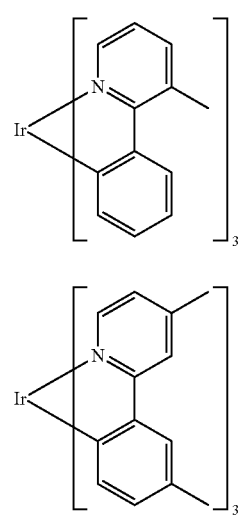
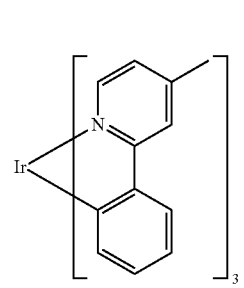
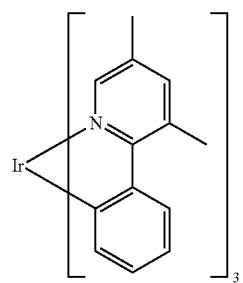
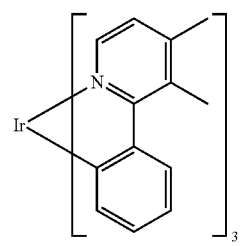
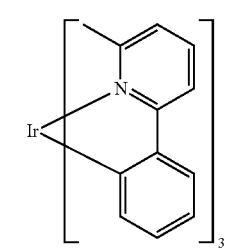
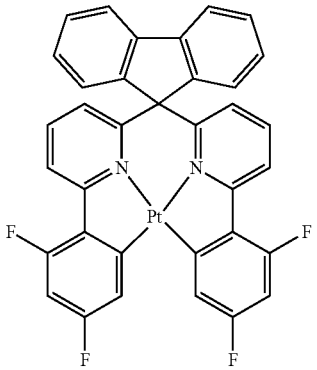
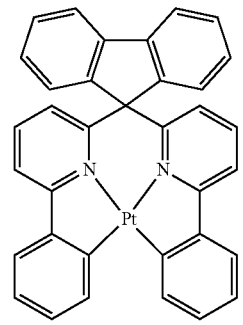

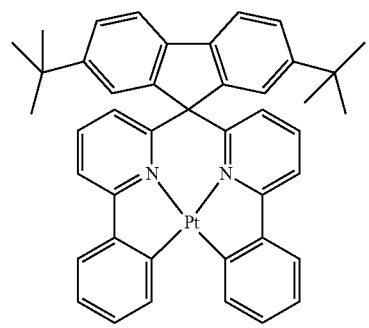
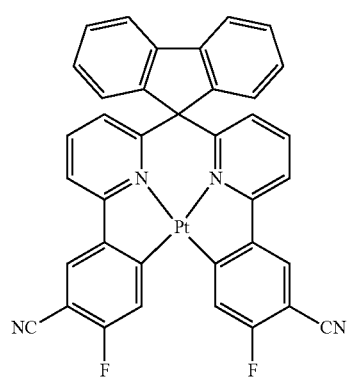
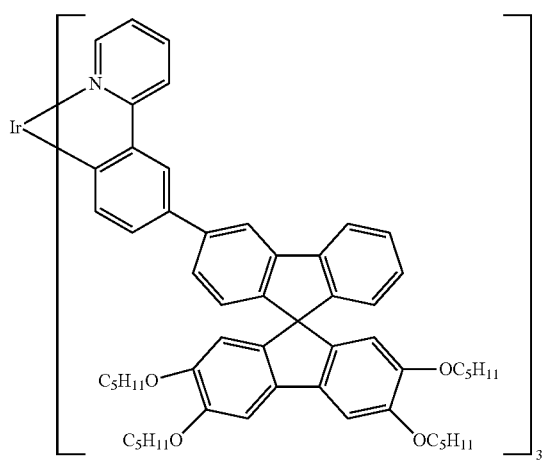
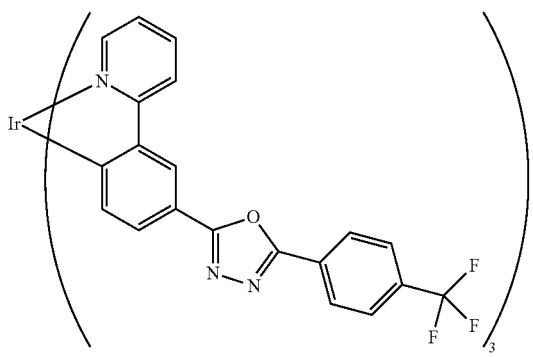
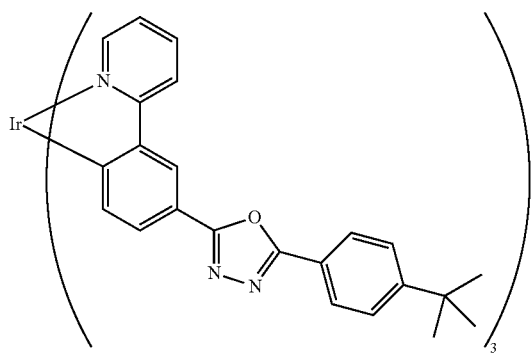
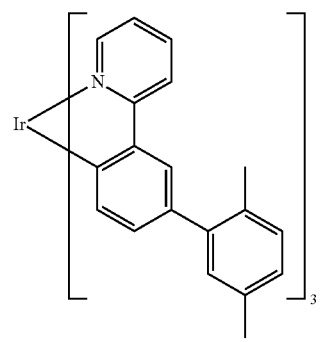
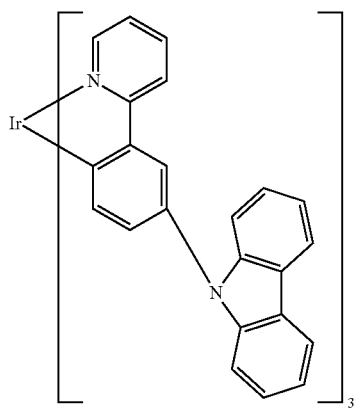
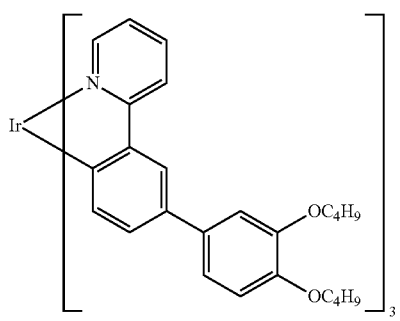

95
-continued
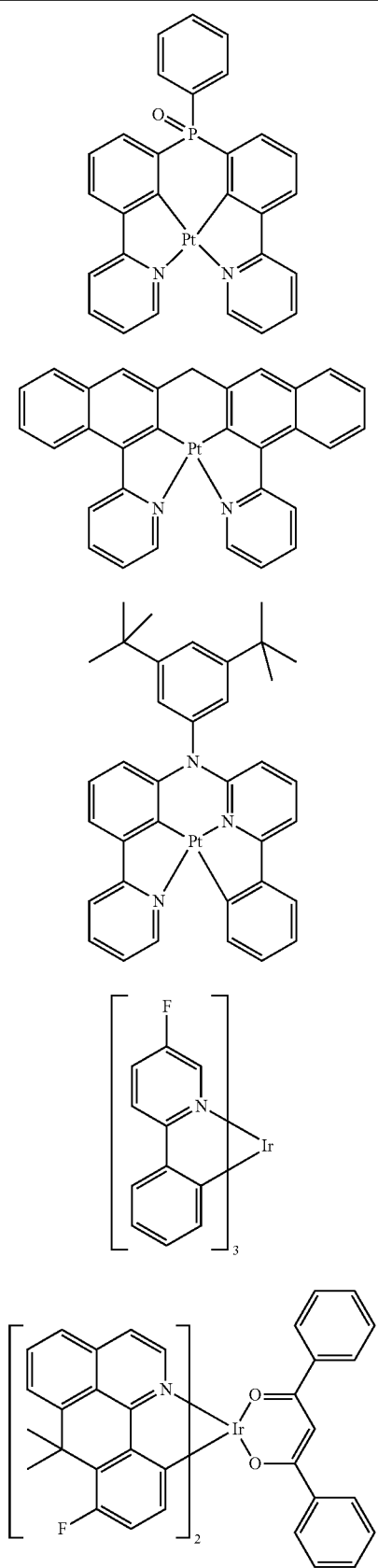
96
-continued
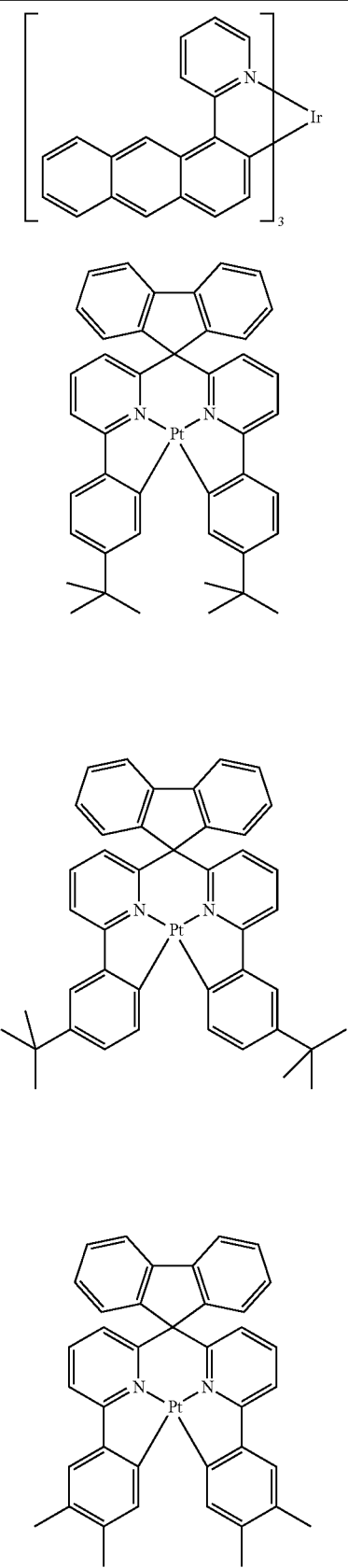

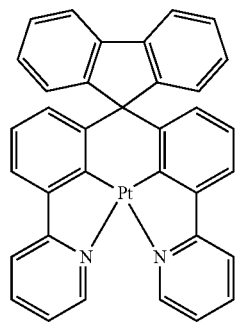
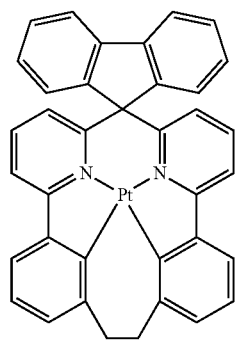
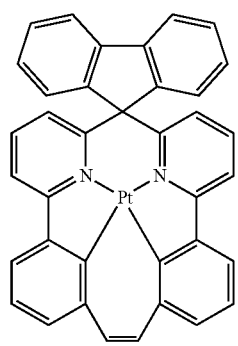
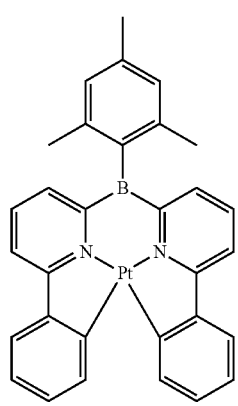
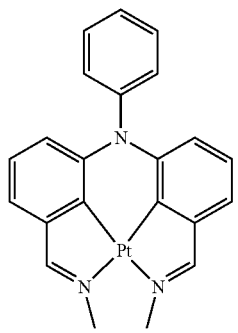
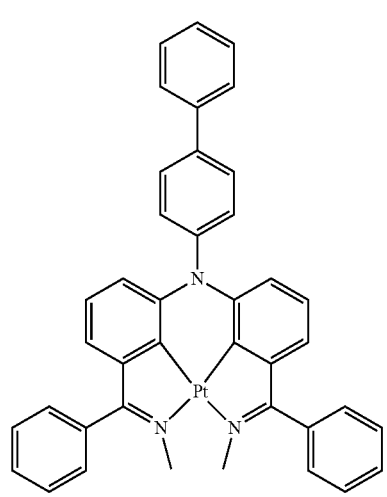
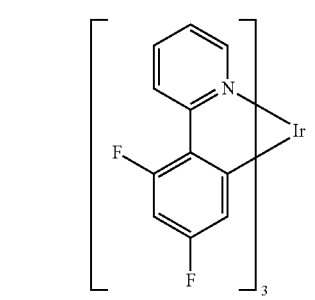
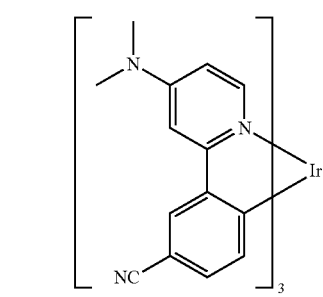

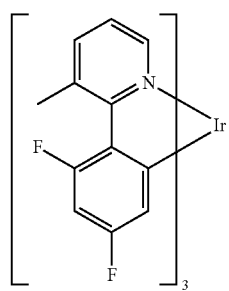
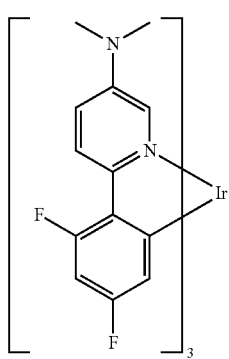
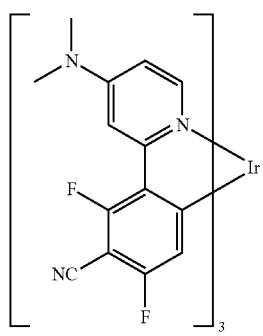
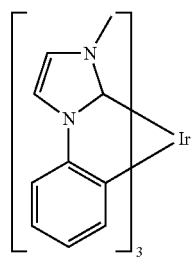
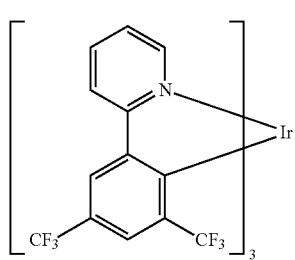
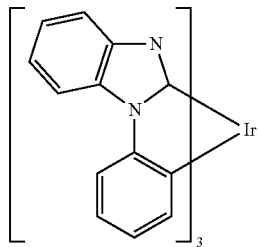
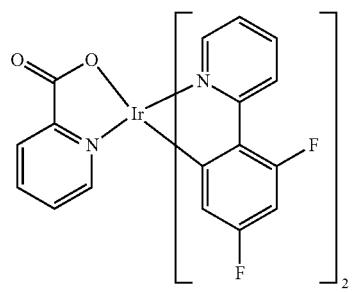
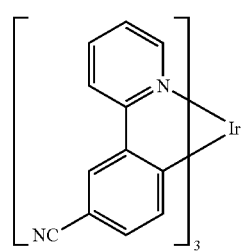
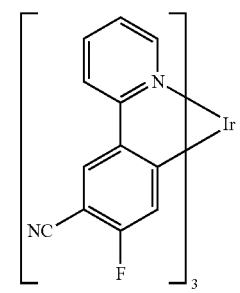
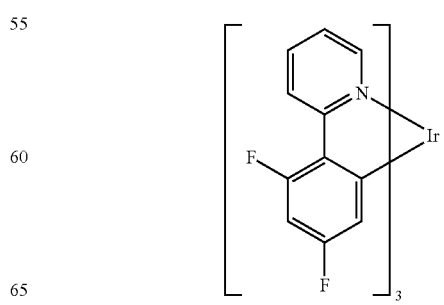

| 101 -continued | 102 -continued |
|---|---|
| 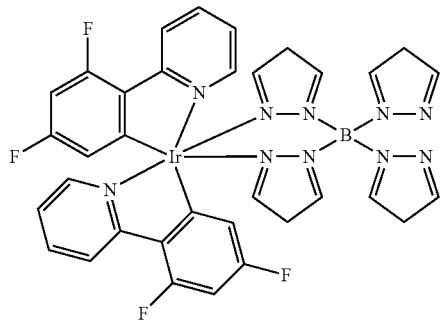 | 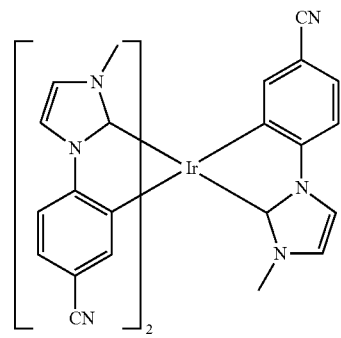 |
| 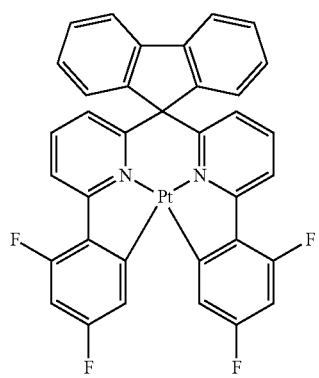 | 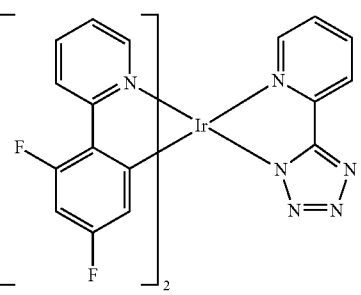 |
| 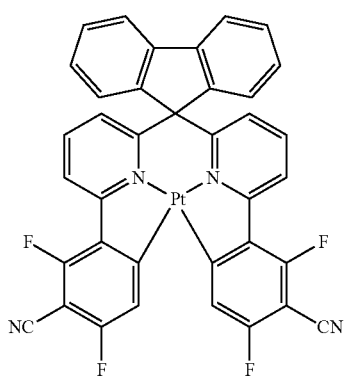 | 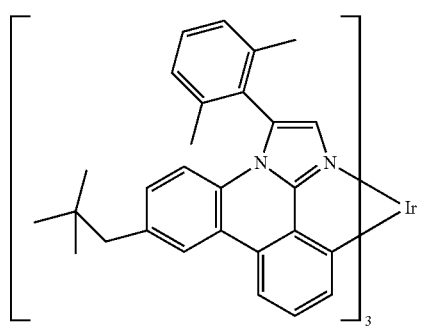 |
|  | 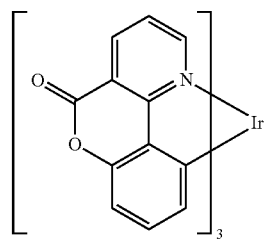 |
| 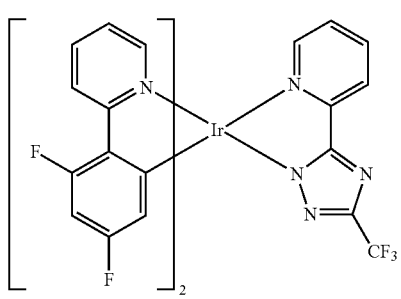 | 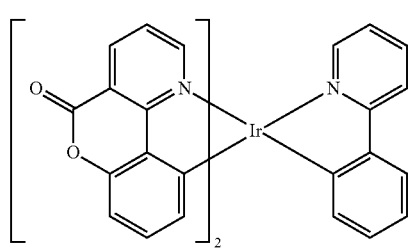 |

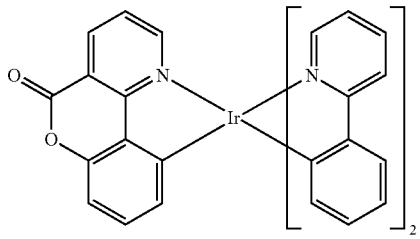
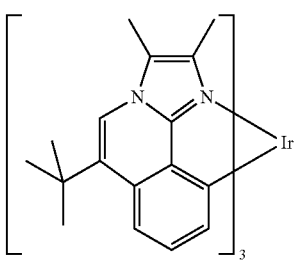
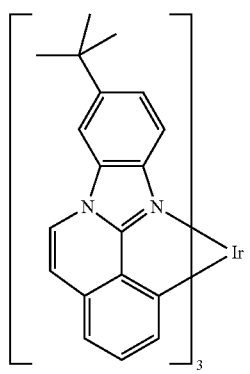
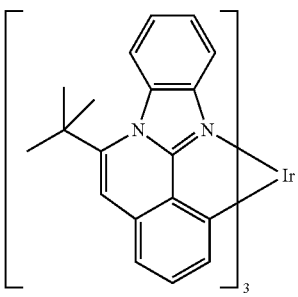
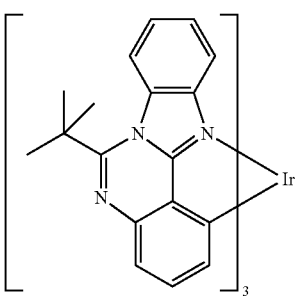
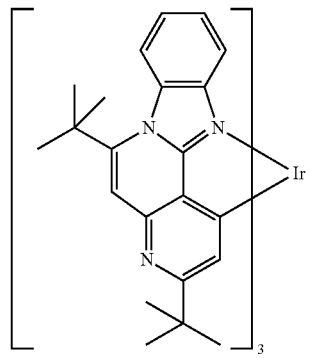
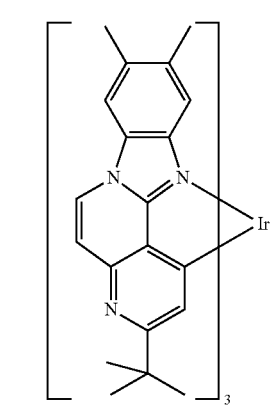

Preferred fluorescent dopants are selected from the class of the aryl-amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracen-amines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are indenofluorenamines and indenofluorenediamines, for example in accordance with WO 2006/108497 or WO 2006/122630, benzoindenofluorenamines and benzoindenofluorendiamines, for example in accordance with WO 2008/006449, and dibenzoindenofluorenamines and dibenzoindenofluorenediamines, for example in accordance with WO 2007/140847, and the indenofluorene derivatives containing condensed aryl groups disclosed in WO 2010/012328.

Suitable matrix materials, preferably for fluorescent dopants, besides the compounds of the formula (1), are materials from various classes of sub-stance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds of the formula (1), are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAIQ.

Apart from cathode, anode and the layer comprising the compound of the formula (1), the electronic device may also comprise further layers. These are selected, for example, from in each case one or more hole-injection layers, hole-transport layers, hole-blocking layers, emitting layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that each of these layers does not necessarily have to be present.

The sequence of the layers of the organic electroluminescent device is preferably the following:
  anode/hole-injection layer/hole-transport layer/emitting layer/electron-transport layer/electron-injection layer/cathode.

It should again be pointed out here that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

The hole-transport materials are particularly preferably materials which can be used in a hole-transport, hole-injection or electron-blocking layer, indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with the as yet unpublished applications EP 12005369.9, EP 12005370.7 and EP 12005371.5), spirodibenzopyranamines (for example in accordance with the as yet unpublished application EP 11009127.9) and dihydro-acridine derivatives (for example in accordance with the as yet unpublished EP 11007067.9).

The cathode of the electronic device preferably comprises metals having a low work function, metal alloys or multi-layered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or car-bonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example AVNi/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers. Furthermore, the anode may also consist of a plurality of layers, for example of an inner layer of ITO and an outer layer of a metal oxide, preferably tungsten oxide, molybdenum oxide or vanadium oxide During production, the electronic device is appropriately (depending on the application) structured, provided with contacts and finally sealed, since the lifetime of the devices according to the invention is shortened in the pres-ence of water and/or air.

In a preferred embodiment, the electronic device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The invention thus furthermore relates to a process for the production of the electronic device according to the invention, characterised in that at least one organic layer is applied by gas-phase deposition or from solution.

In accordance with the invention, the electronic devices comprising one or more compounds of the formula (1) can be employed in displays, as light sources in lighting applications and as light sources in medical and/or cos-metic applications (for example light therapy).

The present invention also relates to a formulation comprising at least one compound of the formula (1) or at least one of the above-mentioned compositions and at least one solvent.

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (-)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol mono-butyl ether, tripropylene glycol dimethyl ether, tetraethylene glycol dimethyl ether, 2-isopropylnaphthalene, pentylbenzene, hexylbenzene, heptyl-benzene, octylbenzene, 1,1-bis(3,4-dimethylphenyl)ethane or mixtures of these solvents.

Devices comprising the compounds of the formula (1) can be employed in a very versatile manner. Thus, for example, electroluminescent devices comprising one or more compounds of the formula (1) can be employed in displays for televisions, mobile telephones, computers and cameras. However, the devices can also be used in lighting applications. Furthermore, electroluminescent devices, for example in OLEDs or OLECs, comprising at least one of the compounds of the formula (1) can be used for phototherapy in medicine or cosmetics. Thus, a large number of diseases (psoriasis, atopic dermatitis, inflammation, acne, skin cancer, etc.) can be treated or skin wrinkling, skin reddening and skin ageing can be prevented or reduced. Furthermore, the light-emitting devices can be utilised in order to keep drinks, meals or foods fresh or in order to sterilise equipment (for example medical equipment).

The present invention therefore relates to an electronic device, preferably an organic electroluminescent device, very preferably an OLED or OLEC and very particularly preferably an OLED, comprising at least one compound of the formula (1) for use in medicine for phototherapy.

The present invention furthermore preferably relates to an electronic device, preferably an organic electroluminescent device, very preferably an OLED or OLEC and very particularly preferably an OLED, comprising at least one compound of the formula (1) for use for the phototherapeutic treatment of skin diseases.

The present invention furthermore very preferably relates to an electronic device, preferably an organic electroluminescent device, very preferably an OLED or OLEC and very particularly preferably an OLED, comprising at least one compound of the formula (1) for use for the phototherapeutic treatment of psoriasis, atopic dermatitis, inflammatory diseases, vitiligo, wound healing and skin cancer.

The present invention furthermore relates to the use of the electronic device, preferably an organic electroluminescent device, very preferably an OLED or OLEC and very particularly preferably an OLED, comprising at least one compound of the formula (1) in cosmetics, preferably for the treatment of acne, ageing skin and of cellulite.

The compounds according to the invention or the organic electroluminescent devices according to the invention are distinguished over the prior art by the following surprising advantages:

1. The compounds according to the invention are very highly suitable for use in an emission layer and exhibit improved performance data compared with compounds from the prior art.
2. The compounds according to the invention have a relatively low sublimation temperature, high temperature stability and can therefore be sublimed without decomposition and without a residue. Furthermore, they have high oxidation stability and a high glass-transition temperature, which is advantageous both for the processability, for example from solution or from the gas phase, and also for the compound in electronic devices.
3. The use of the compounds according to the invention in electronic devices, in particular employed as matrix material, but also as electron-transport or electron-injection material, result in high efficiencies, low operating voltages and in long lifetimes.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention claimed at present.

The teaching on technical action disclosed with the present invention can be abstracted and combined with other examples.

The invention is illustrated in greater detail by the following examples, without wishing to restrict it thereby.

EXAMPLES

The following syntheses are carried out, unless indicated otherwise, under a protective-gas atmosphere in dried solvents. The solvents and reagents can be purchased, for example, from Sigma-ALDRICH or ABCR. The numbers in square brackets for chemical compounds which are known from the literature relate to the CAS numbers.

Example 1

Synthesis of 3-dibenzofuran-4-yi-6,9-diphenyl-9H-carbazole

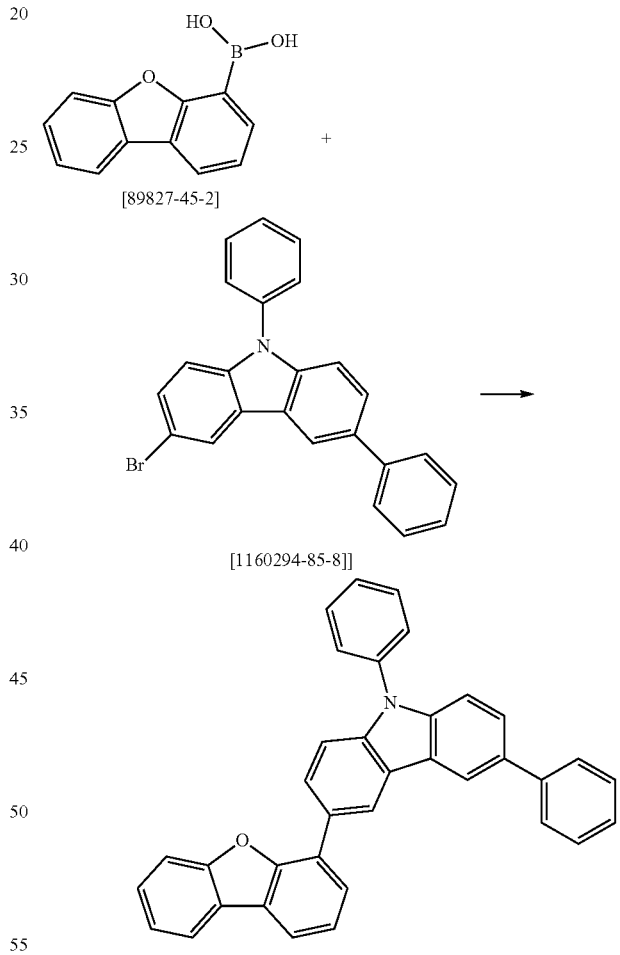

28.9 g (136 mmol) of dibenzofuran-4-boronic acid, 40 g (124.1 mmol) of 3-bromo-9-phenyl-9H-carbazole and 78.9 ml (158 mmol) of $Na_2CO_3$ (2 M solution) are suspended in 120 ml of toulene, 120 ml of ethanol and 100 ml of water. 2.6 g (2.2 mmol) of $Pd(PPh_3)_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 49.7 g (121 mmol), corresponding to 97% of theory.

The following compounds can be obtained analogously:
| Starting material 1 | Starting material 2 | Product | Yield |
|---|---|---|---|
| 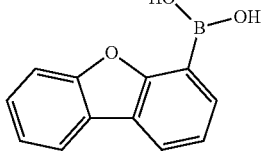 [89827-45-2] | 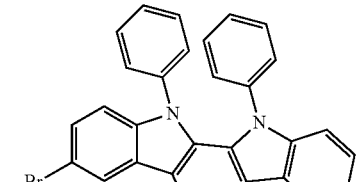 [206447-74-7] | 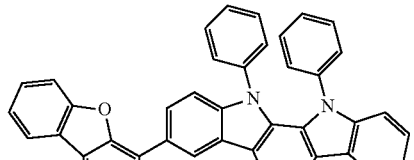 | 69% |
| 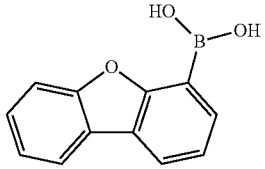 [89827-45-2] | 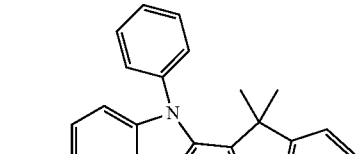 [1343493-06-0] | 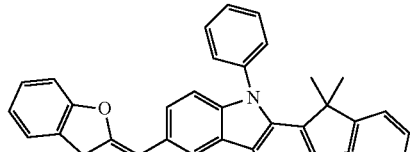 | 92% |
| 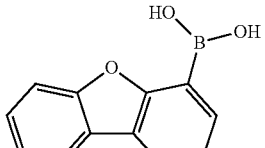 [89827-45-2] | 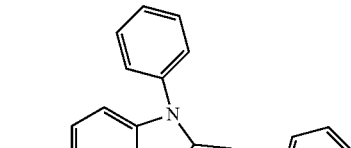 [1357572-26-9] | 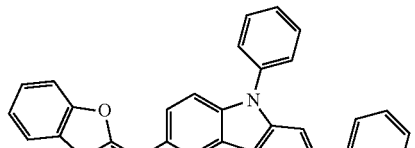 | 68% |
| 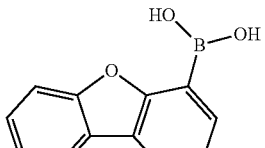 [89827-45-2] | 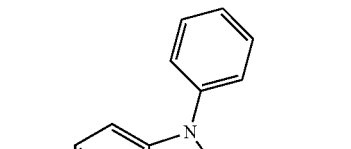 | 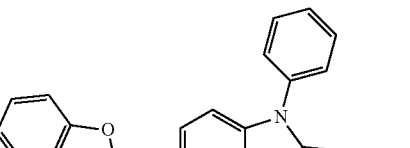 | 77% |
| 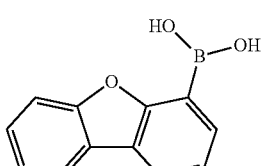 [89827-45-2] | 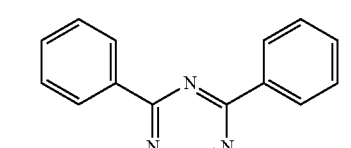 [3842-55-5] | 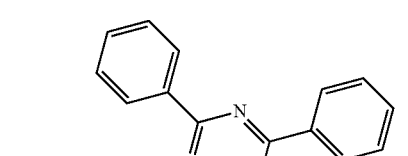 | 63% |

-continued
| Starting material 1 | Starting material 2 | Product | Yield |
|---|---|---|---|
| 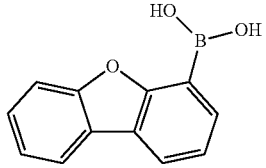 [89827-45-2] | 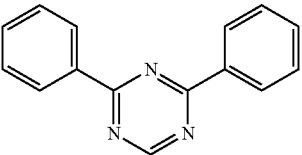 [56181-49-8] | 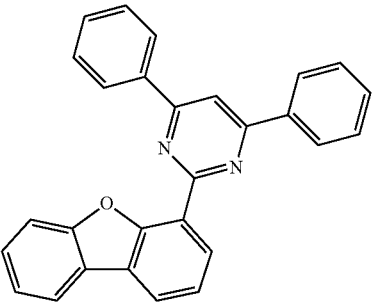 [SMILES: c1ccc(-c2cc(-c3ccccc3)nc(-c3cccc4c3oc3ccccc34)n2)cc1] | 75% |
| 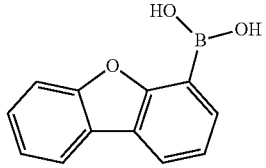 [89827-45-2] | 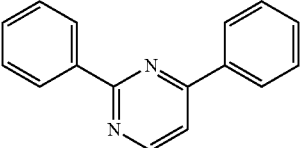 [40734-24-5] | 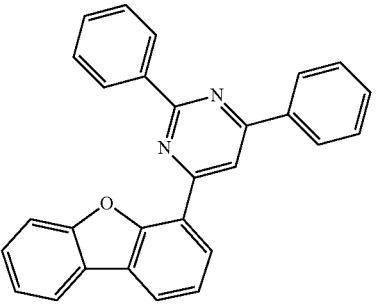 [SMILES: c1ccc(-c2cc(-c3cccc4c3oc3ccccc34)nc(-c3ccccc3)n2)cc1] | 71% |
| 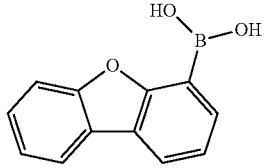 [89827-45-2] | 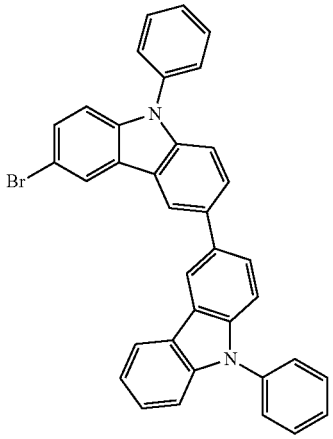 [918137-84-5] | 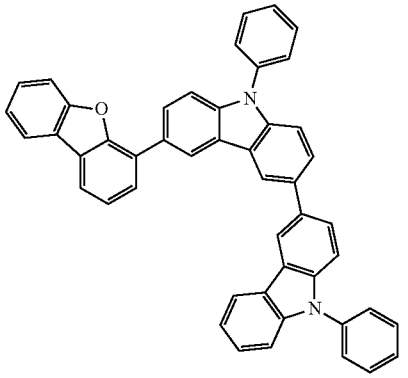 [SMILES: c1ccc(-n2c3ccccc3c3cc(-c4ccc5c(c4)c4cc(-c6cccc7c6oc6ccccc67)ccc4n5-c4ccccc4)ccc32)cc1] | 75% |
| 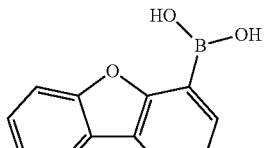 [89827-45-2] | 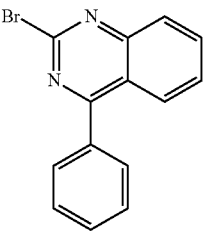 [354574-58-6] | 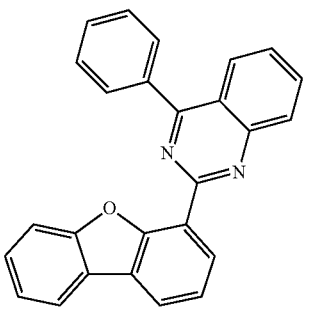 [SMILES: c1ccc(-c2nc(-c3cccc4c3oc3ccccc34)nc3ccccc23)cc1] | 83% |

Example 2

Synthesis of 1-dibenzofuran-4-yl-2-phenyl-1H-benzimidazole

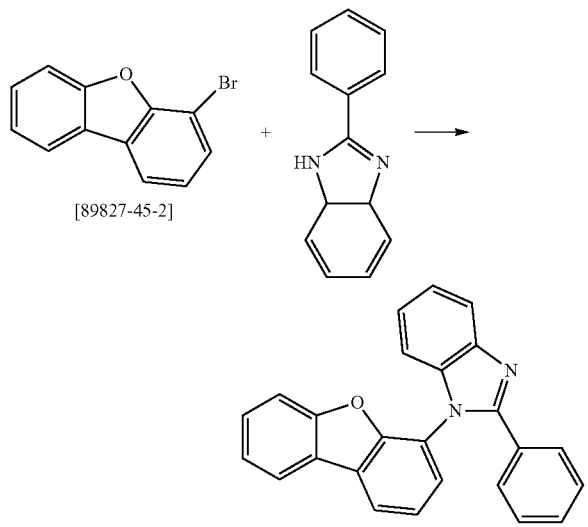

[89827-45-2]

8.0 g (42.2 mmol) of copper(I) iodide and 11.7 ml (97.5 mmol) of trans-cyclohexanediamine are added to a vigorously stirred suspension of 42 g (234 mmol) of 2-phenyl-1H-benzimidazole, 57.7 g (234 mmol) of 4-bromodibenzofuran and 416.4 g (1961 mmol) of potassium phosphate in 1170 ml of dioxane, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol. Yield: 52 g (144 mmol), 85% of theory.

The following compounds can be obtained analogously:

Example 3

Synthesis of 3,9-diphenyl-6-(6-trimethylsilanyldibenzofuran-4-yl)-9H-carbazole

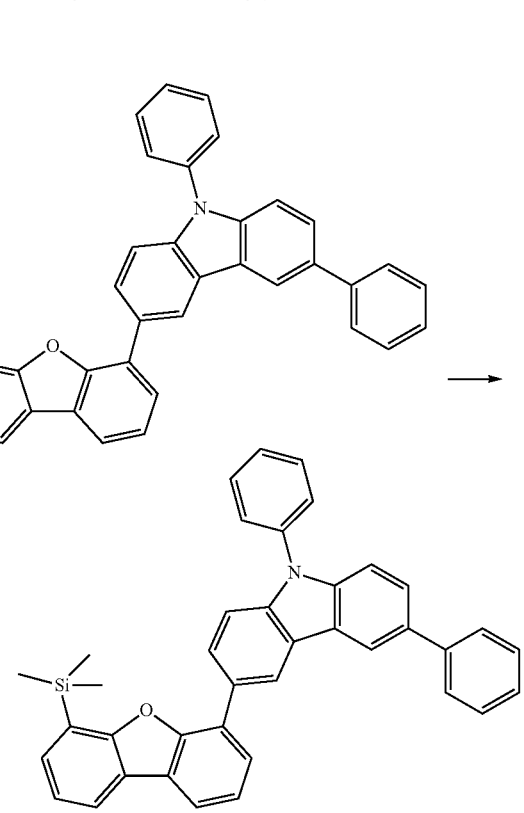

127 ml (225.4 mmol) of n-buthyllithium (2.5 M in hexane) are added dropwise to a solution, cooled to 20° C., of 58.7 g (121 mmol) of 3-dibenzofuran-4-yl-6,9-diphenyl-9H-carbazole and 28 g (242 mmol) of TMEDA in 1000 ml

| Starting material 1 | Starting material 2 | Product | Yield |
|---|---|---|---|
| [89827-45-2] | [1848-84-6] | | 88% |
| [97511-05-2] | [716-79-0] | | 82% | of THF. The reaction mixture is stirred at room temperature for 3 h, then cooled to 0° C., and 26 g (242 mmol) of chlorotrimetylsilane are added dropwise over the course of 30 min., and the mixture is stirred at room temperature for 8 h. The solvent is subsequently removed in vacuo, and the residue is purified by chromatography on silica gel with chloroform as eluent. Yield: 41 g (72 mmol), 61% of theory.

The following compounds can be obtained analogously:

| Starting material 1 | Product | Yield |
|---|---|---|
|  |  | 63% |
|  |  | 59% |
|  |  | 57% |
|  |  | 52% |

| Starting material 1 | Product | Yield |
|---|---|---|
| | | 60% |
| | | 54% |
| | | 59% |
| | | 76% |
| | | 78% |

| Starting material 1 | Product | Yield |
|---|---|---|
| | | 69% |

Example 4

Synthesis of 6-(3,9-diphenyl-9H-carbazol-3-yl)-4-dibenzofuranyl-boronic acid

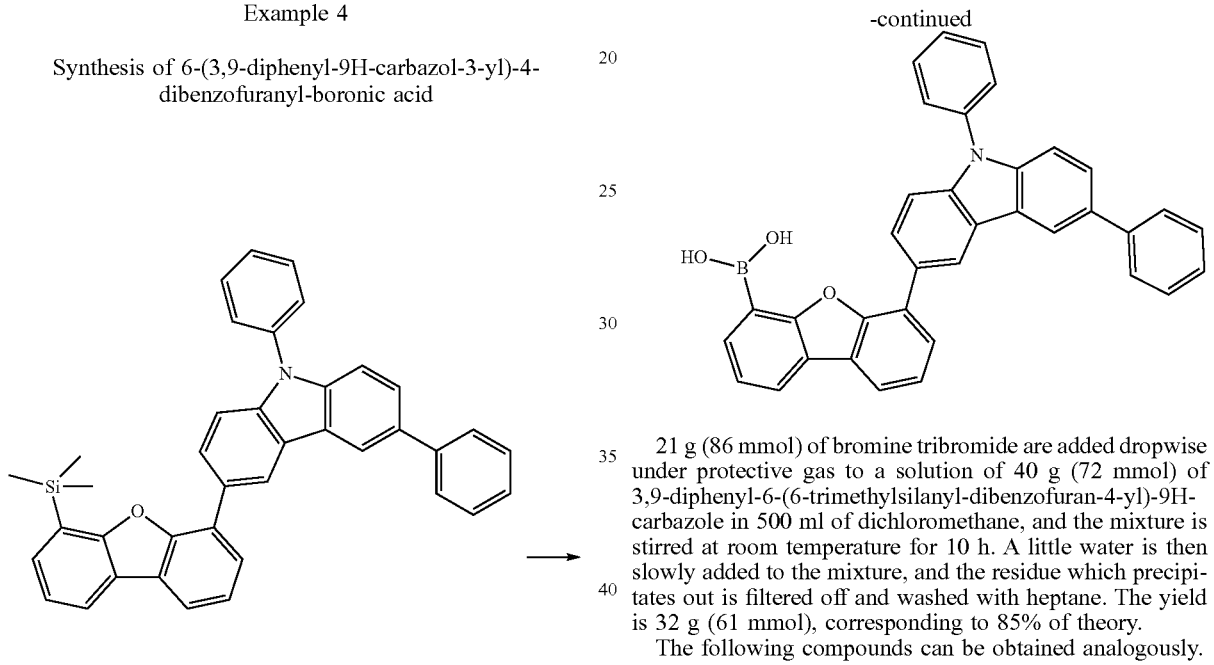

21 g (86 mmol) of bromine tribromide are added dropwise under protective gas to a solution of 40 g (72 mmol) of 3,9-diphenyl-6-(6-trimethylsilanyl-dibenzofuran-4-yl)-9H-carbazole in 500 ml of dichloromethane, and the mixture is stirred at room temperature for 10 h. A little water is then slowly added to the mixture, and the residue which precipitates out is filtered off and washed with heptane. The yield is 32 g (61 mmol), corresponding to 85% of theory.

The following compounds can be obtained analogously.

| Starting material 1 | Product | Yield |
|---|---|---|
| | | 80% |
| | | 83% |

-continued

| Starting material 1 | Product | Yield |
|---|---|---|
| | | 81% |
| | | 79% |
| | | 69% |
| | | 78% |

-continued
| Starting material 1 | Product | Yield |
|---|---|---|
| | | 77% |
| | | 82% |
| | | 85% |
| | | 80% |
Example 5
Synthesis of 6-(3,9-diphenyl-9H-carbazol-3-yl)-4-dibenzofuranyl-boronic acid
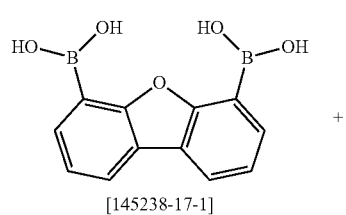
[145238-17-1]
+
-continued
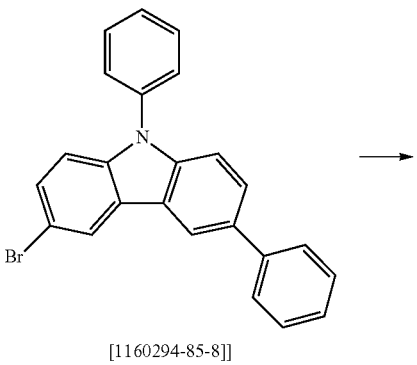
[1160294-85-8]]

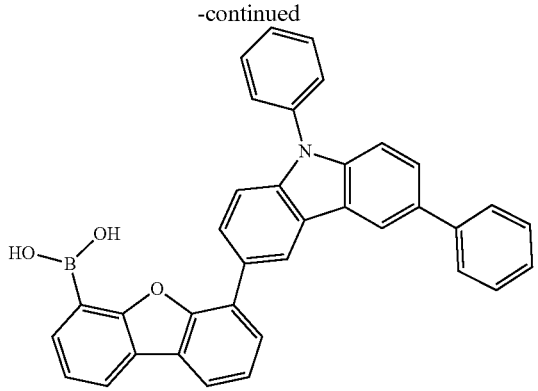

9 g (32 mmol) of 4,6-dibenzofurandiylbisboronic acid, 12.5 g (31.6 mmol) of 3-bromo-9-phenyl-9H-carbazole, 31 ml (63 mmol) of Na$_2$CO$_3$ (2 M solution) are suspended in 120 ml of toulene, 120 ml of ethanol. 0.73 g (0.63 mmol) of Pd(PPh$_3$)$_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 11.2 g (21 mmol), corresponding to 67% of theory.

The following compounds can be obtained analogously:

| Starting material 1 | Starting material 2 |
|---|---|
| 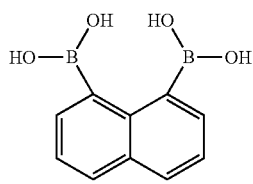<br>[947617-22-3] | 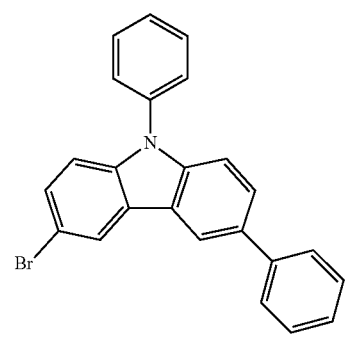<br>[1180294-85-8]] |
| 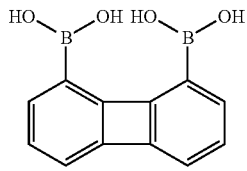<br>[480438-76-4] | 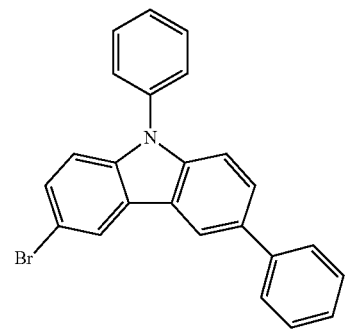<br>[1160294-85-8]] |
| 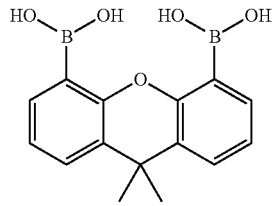<br>[862159-27-1] | 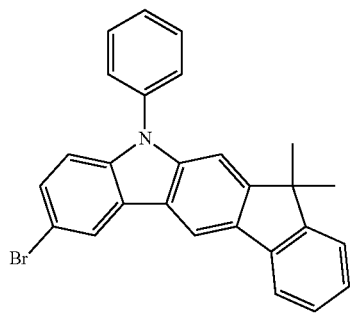<br>[1257220-44-2] |

-continued
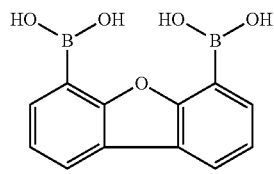
[145238-17-1]
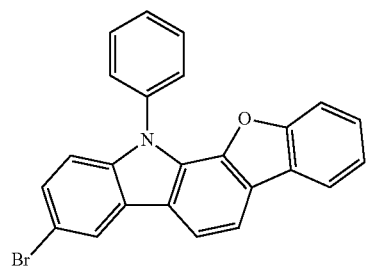
[1338919-75-7]
| Product | Yield |
|---|---|
| 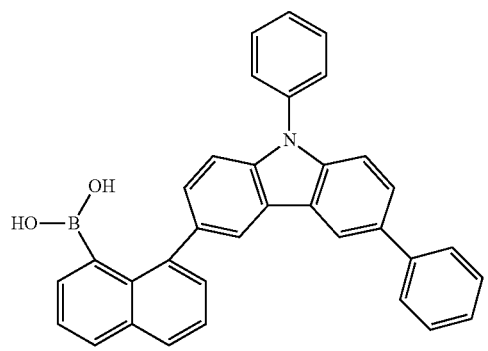 | 85% |
| 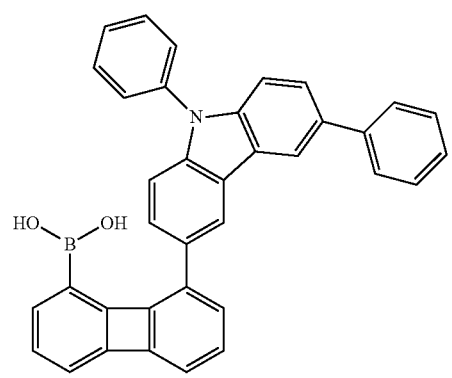 [SMILES: OB(O)c1cccc2c1-c1c(-c3ccc4c(c3)c3cc(-c5ccccc5)ccc3n4-c3ccccc3)cccc1-2] | 69% |
| 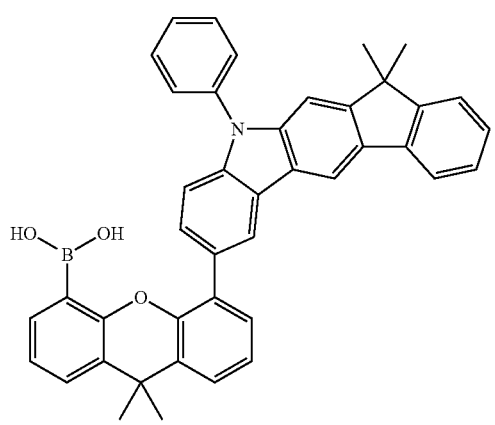 [SMILES: CC1(C)c2ccccc2-c2cc3c4cc(-c5cccc6c5Oc5c(B(O)O)cccc5C6(C)C)ccc4n(-c4ccccc4)c3cc21] | 74% |

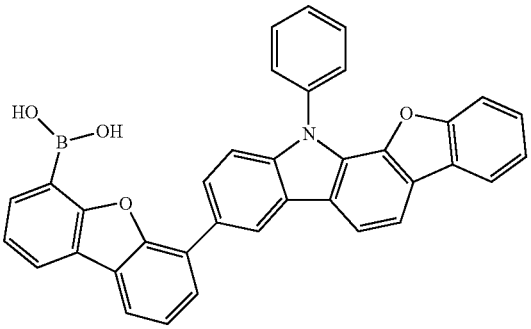 [SMILES: OB(O)c1cccc2c1oc1c(-c3ccc4c(c3)c3ccc5c6ccccc6oc5c3n4-c3ccccc3)cccc12]

76%

Example 6

Synthesis of 10-(6-bromodibenzofuran-4-yl)-7-phenyl-7H-12-thia-7-azaindeno[1,2-a]fluorene

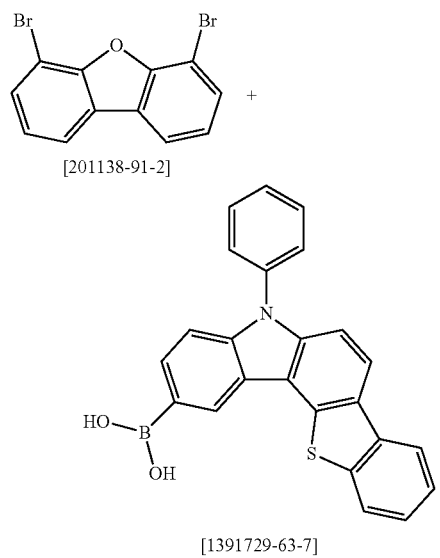

[201138-91-2]

[1391729-63-7]

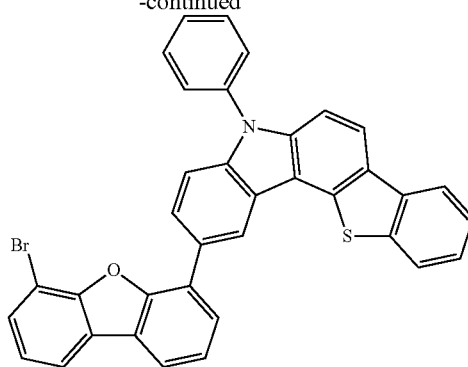

12.5 g (32 mmol) of 5-phenyl-5H[1]benzothieno[3,2-c]carbazol-3-yl) boronic acid, 8.9 g (31.6 mmol) of 4,6-dibromodibenzofuran, 31 ml (63 mmol) of $Na_2CO_3$ (2 M solution) are suspended in 120 ml of toluene and 120 ml of ethanol. 0.73 g (0.63 mmol) of $Pd(PPh_3)_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 13.3 g (22 mmol), corresponding to 73% of theory.

The following compounds can be obtained analogously.

| Starting material 1 | Starting material 2 |
|---|---|
| 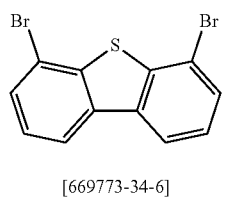 [SMILES: Brc1cccc2c1sc1c(Br)cccc12]<br>[669773-34-6] | 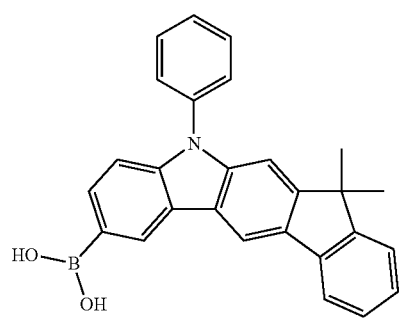<br>[1379585-25-7] |

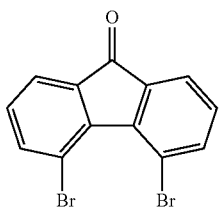
[69414-97-7]
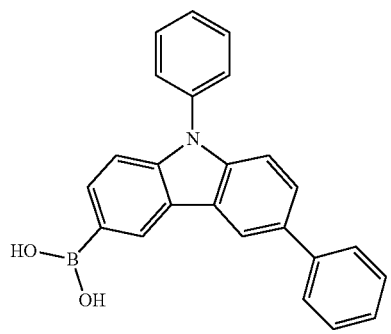
[1133058-06-6]
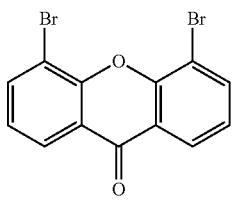
[1262398-42-4]
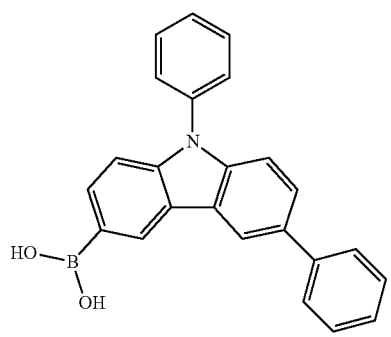
[1133058-06-6]
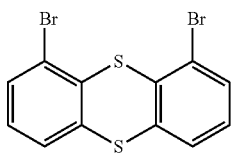
[176646-34-7]
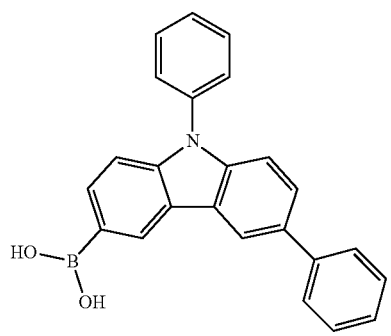
[1133058-06-6]
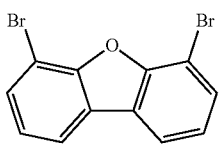
[201138-91-2]
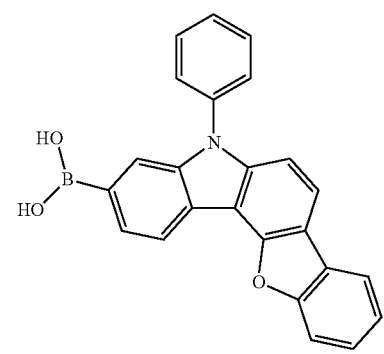
[1391729-62-6]

-continued
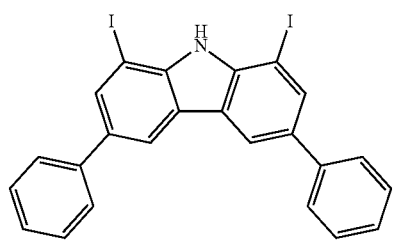
[501330-43-4]
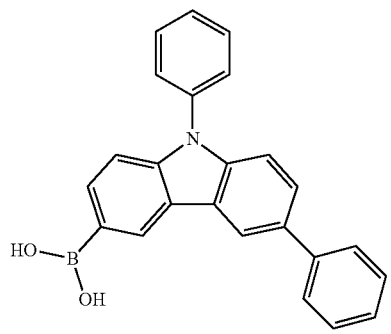
[1133058-06-6]
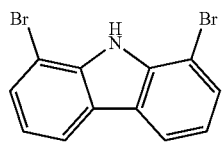
[553663-65-3]
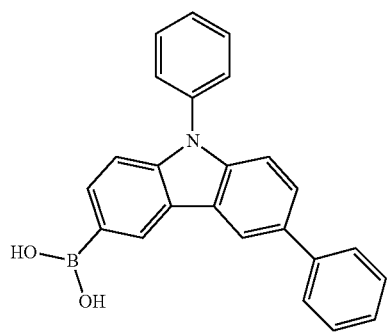
[1133058-06-6]
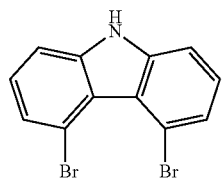
[905702-33-2]
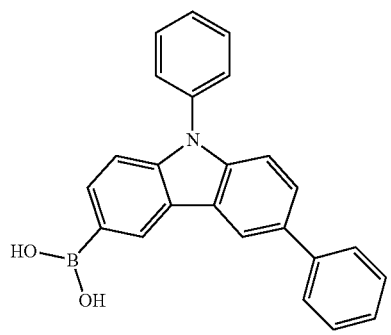
[1133058-06-6]
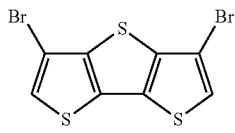
[502764-54-7]
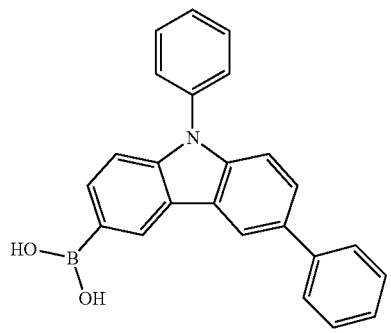
[1133058-06-6]

-continued
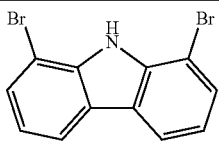
[553663-65-3]
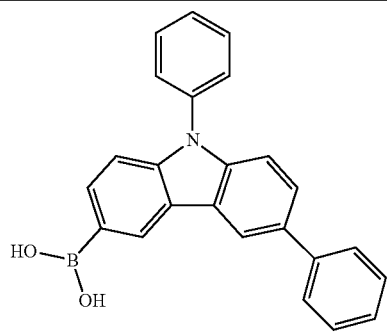
[1133058-06-6]
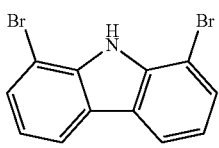
[553663-65-3]
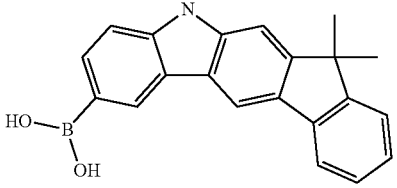
[1379585-25-7]
| Product | Yield |
|---|---|
| 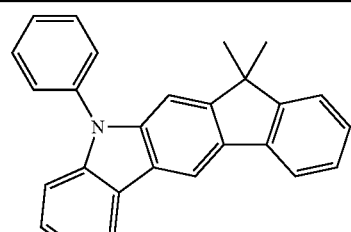 | 51% |
| 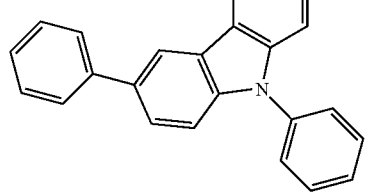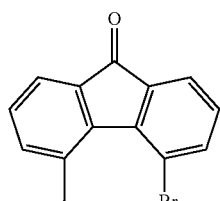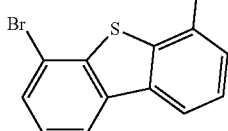 | 65% |

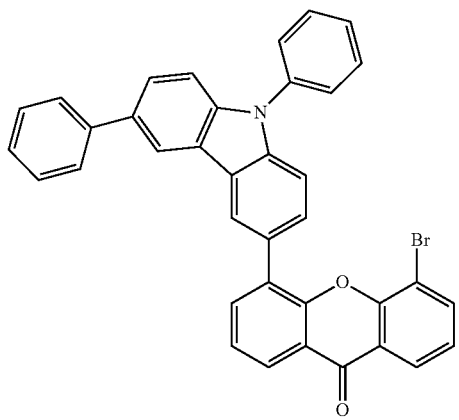 [SMILES: O=c1c2cccc(Br)c2oc2c(-c3ccc4c(c3)c3cc(-c5ccccc5)ccc3n4-c3ccccc3)cccc12]
69%
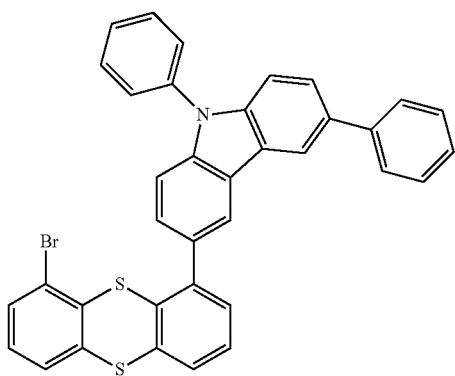 [SMILES: Brc1cccc2c1Sc1c(cccc1-c1ccc3c(c1)c1cc(-c4ccccc4)ccc1n3-c1ccccc1)S2]
67%
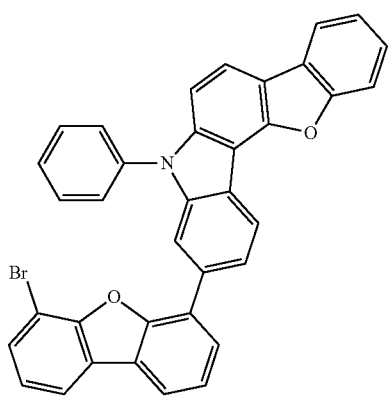 [SMILES: Brc1cccc2c1oc1c(-c3ccc4c5c6oc7ccccc7c6ccc5n(-c5ccccc5)c4c3)cccc12]
62%
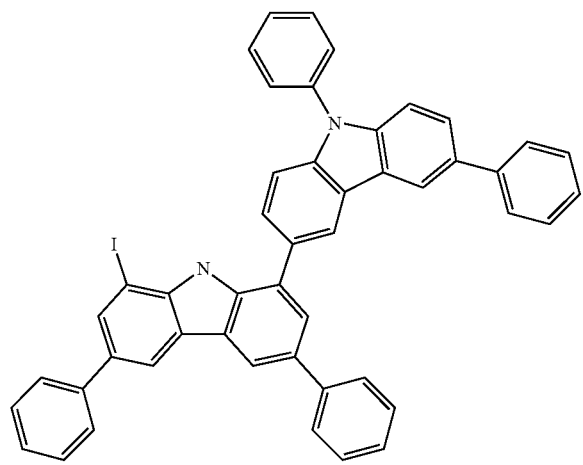 [SMILES: Ic1cc(-c2ccccc2)cc2c1[nH]c1c(-c3ccc4c(c3)c3cc(-c5ccccc5)ccc3n4-c3ccccc3)cc(-c3ccccc3)cc12]
62%

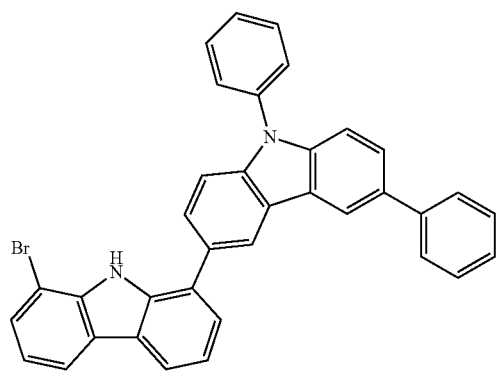 [SMILES: Brc1cccc2c1[nH]c1c(-c3ccc4c(c3)c3cc(-c5ccccc5)ccc3n4-c3ccccc3)cccc12] 61%
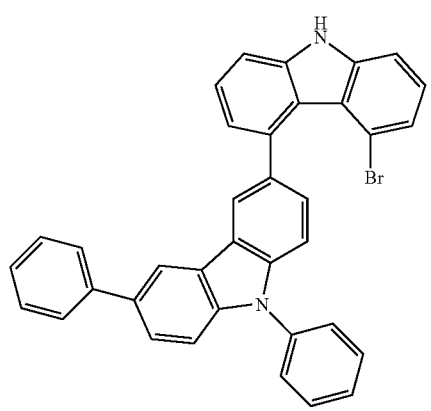 [SMILES: Brc1cccc2[nH]c3cccc(-c4ccc5c(c4)c4cc(-c6ccccc6)ccc4n5-c4ccccc4)c3c12] 64%
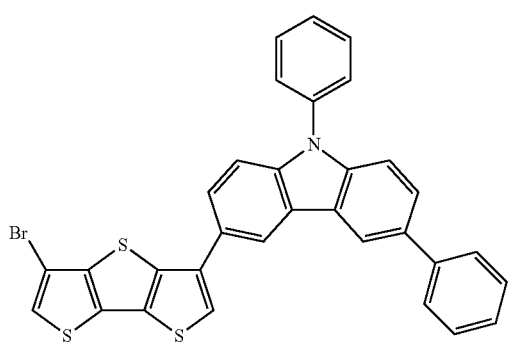 [SMILES: Brc1csc2c1sc1c(-c3ccc4c(c3)c3cc(-c5ccccc5)ccc3n4-c3ccccc3)csc12] 66%
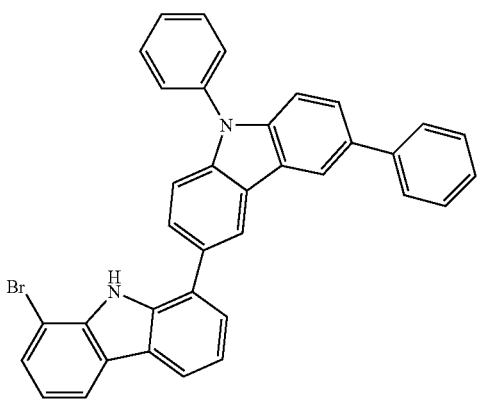 [SMILES: Brc1cccc2c1[nH]c1c(-c3ccc4c(c3)c3cc(-c5ccccc5)ccc3n4-c3ccccc3)cccc12] 56%

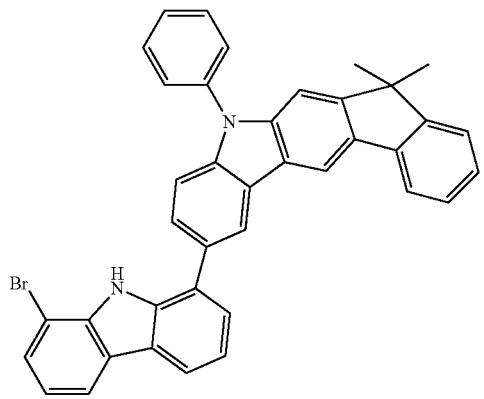 [SMILES: CC1(C)c2ccccc2-c2cc3c4cc(-c5cccc6c5[nH]c5c(Br)cccc56)ccc4n(-c4ccccc4)c3cc21]
72%
The following compounds can also be obtained analogously by a second addition reaction with the corresponding boro acids: The residue is recrystallised from toluene and finally sublimed in a high vacuum (p=5×10 mbar).
| Starting material 1 | Starting material 2 |
|---|---|
| 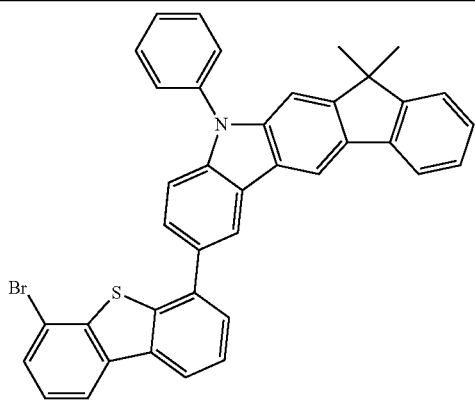 | 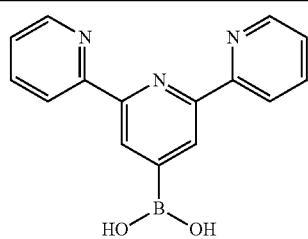 [1036005-64-7] |
| 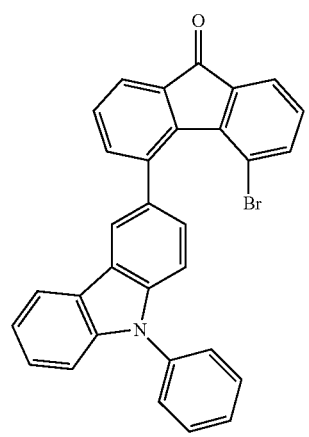 [SMILES: O=C1c2cccc(Br)c2-c2c1cccc2-c1ccc2c(c1)c1ccccc1n2-c1ccccc1] | 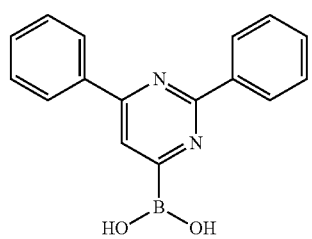 [1251825-66-7] |

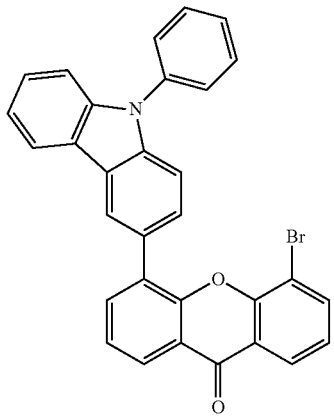 [SMILES: O=c1c2cccc(Br)c2oc2c(-c3ccc4c(c3)c3ccccc3n4-c3ccccc3)cccc12]
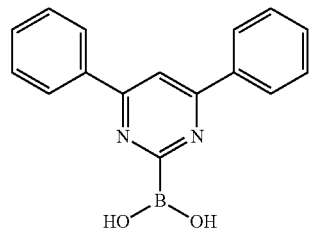
[1314221-56-1]
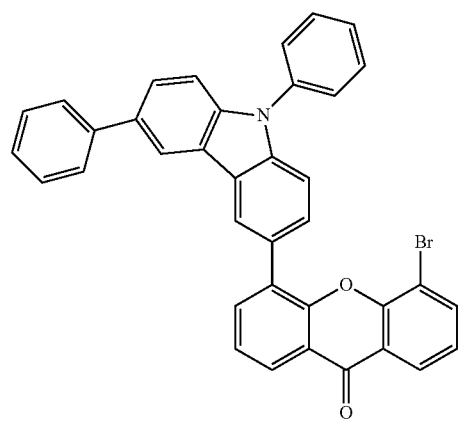 [SMILES: O=c1c2cccc(Br)c2oc2c(-c3ccc4c(c3)c3cc(-c5ccccc5)ccc3n4-c3ccccc3)cccc12]
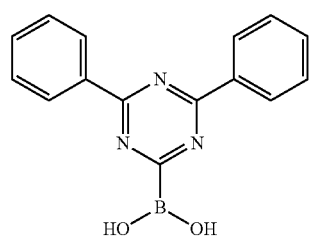
[1251825-65-6]
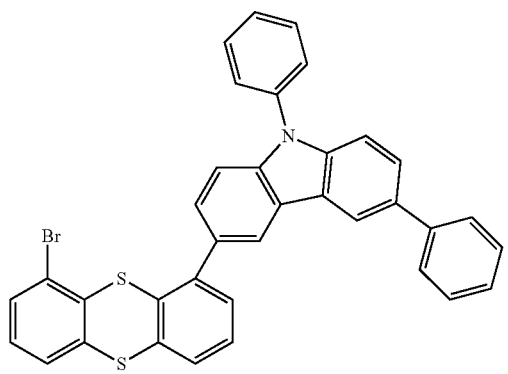 [SMILES: Brc1cccc2c1Sc1c(cccc1-c1ccc3c(c1)c1cc(-c4ccccc4)ccc1n3-c1ccccc1)S2]
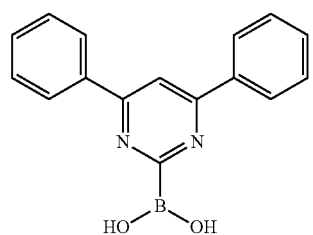
[1314221-56-1]
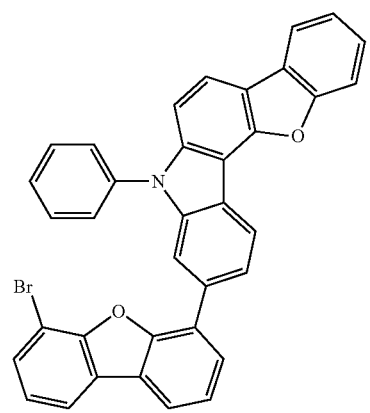 [SMILES: Brc1cccc2c1oc1c(-c3ccc4c5c6oc7ccccc7c6ccc5n(-c5ccccc5)c4c3)cccc12]
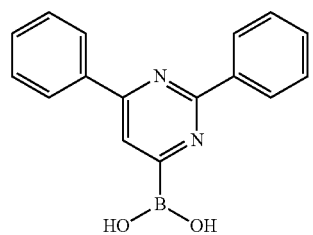
[1251825-66-7]

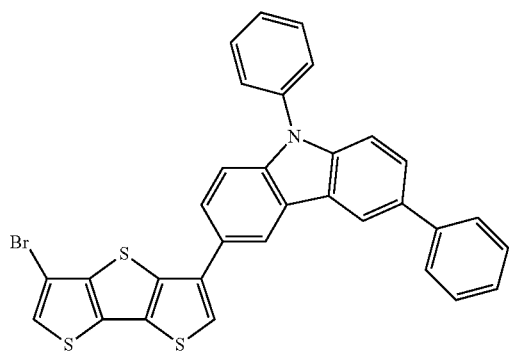 [SMILES: Brc1csc2c1sc1c(-c3ccc4c(c3)c3cc(-c5ccccc5)ccc3n4-c3ccccc3)csc12]
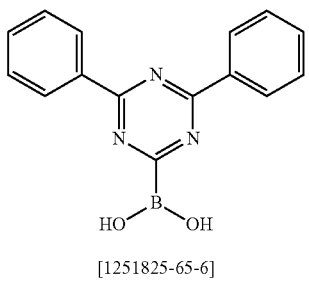 [SMILES: OB(O)c1nc(-c2ccccc2)nc(-c2ccccc2)n1]
[1251825-65-6]
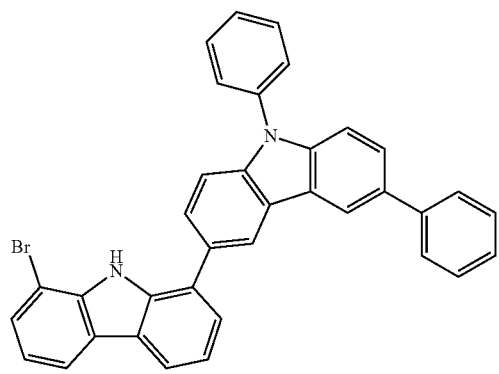 [SMILES: Brc1cccc2c1[nH]c1c(-c3ccc4c(c3)c3cc(-c5ccccc5)ccc3n4-c3ccccc3)cccc12]
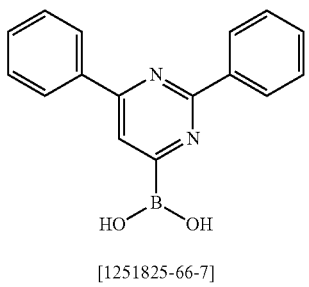 [SMILES: OB(O)c1cc(-c2ccccc2)nc(-c2ccccc2)n1]
[1251825-66-7]
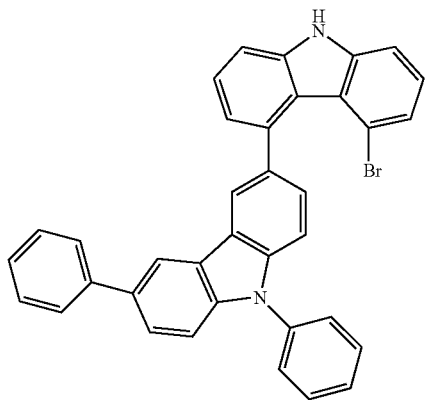 [SMILES: Brc1cccc2[nH]c3cccc(-c4ccc5c(c4)c4cc(-c6ccccc6)ccc4n5-c4ccccc4)c3c12]
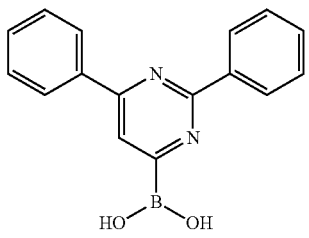
[1251825-66-7]
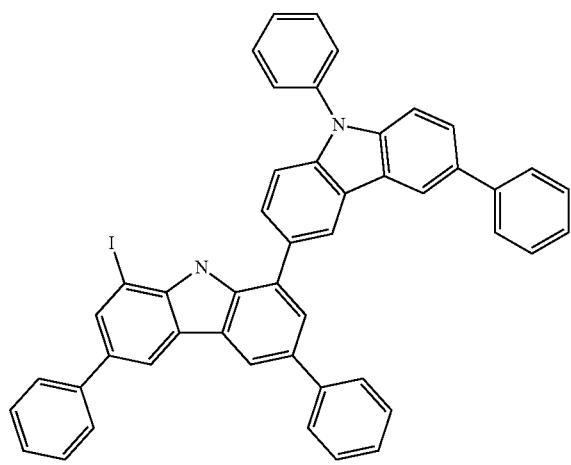 [SMILES: Ic1cc(-c2ccccc2)cc2c1[nH]c1c(-c3ccc4c(c3)c3cc(-c5ccccc5)ccc3n4-c3ccccc3)cc(-c3ccccc3)cc12]
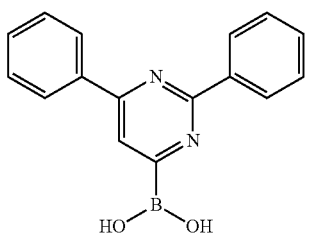
[1251825-66-7]

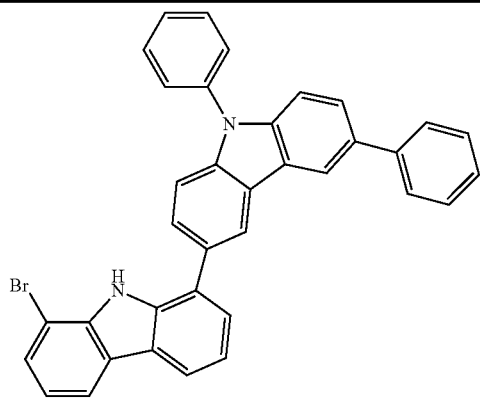
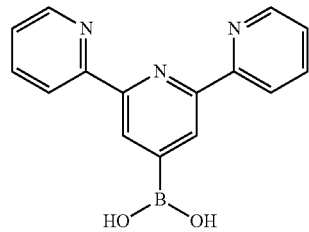
[1036005-64-7]
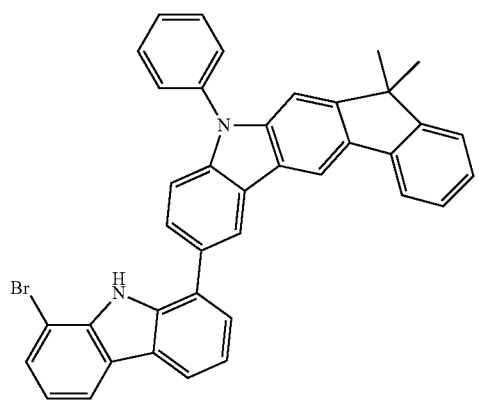 [SMILES: CC1(C)c2ccccc2-c2cc3c4cc(-c5cccc6c5[nH]c5c(Br)cccc56)ccc4n(-c4ccccc4)c3cc21]
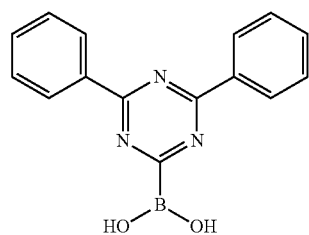
[1251825-65-6]
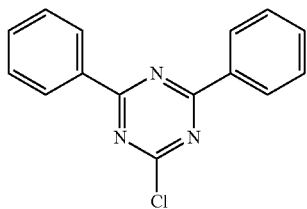
[3842-55-5]
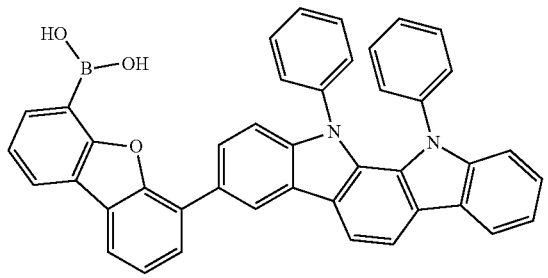 [SMILES: OB(O)c1cccc2c1oc1c(-c3ccc4c(c3)c3ccc5c6ccccc6n(-c6ccccc6)c5c3n4-c3ccccc3)cccc12]
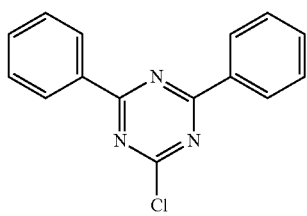
[3842-55-5]
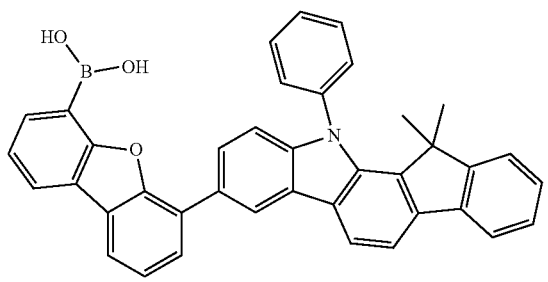 [SMILES: CC1(C)c2ccccc2-c2ccc3c4cc(-c5cccc6c5oc5c(B(O)O)cccc56)ccc4n(-c4ccccc4)c3c21]

151 152
-continued
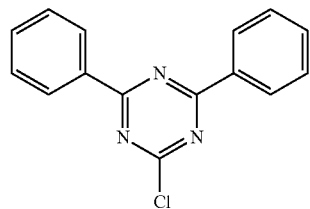
[3842-55-5]
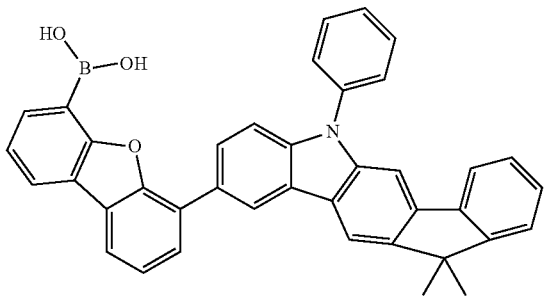 [SMILES: CC1(C)c2ccccc2-c2cc3c(cc21)c1cc(-c2cccc4c2oc2c(B(O)O)cccc24)ccc1n3-c1ccccc1]
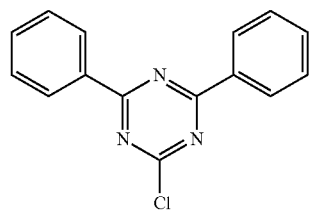
[3842-55-5]
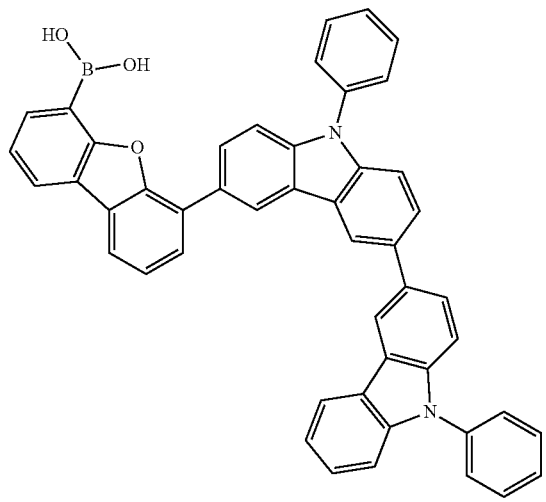 [SMILES: OB(O)c1cccc2c1oc1c(-c3ccc4c(c3)c3cc(-c5ccc6c(c5)c5ccccc5n6-c5ccccc5)ccc3n4-c3ccccc3)cccc12]
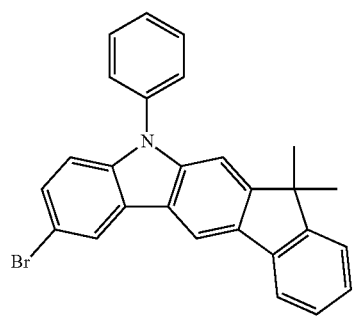
[1257220-44-2]
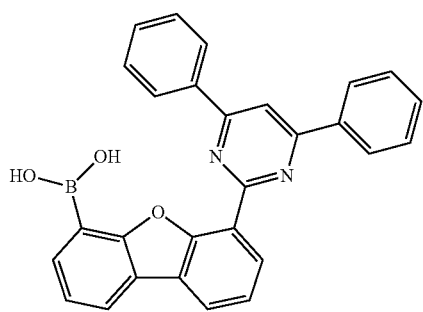 [SMILES: OB(O)c1cccc2c1oc1c(-c3nc(-c4ccccc4)cc(-c4ccccc4)n3)cccc12]
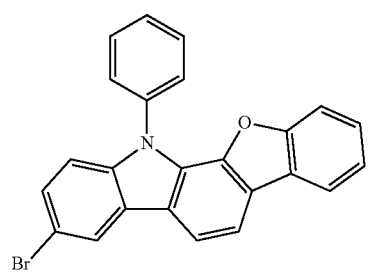
[133819-75-7]
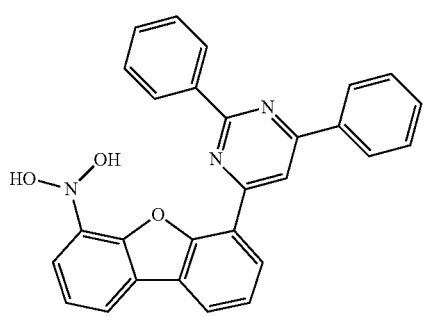

-continued
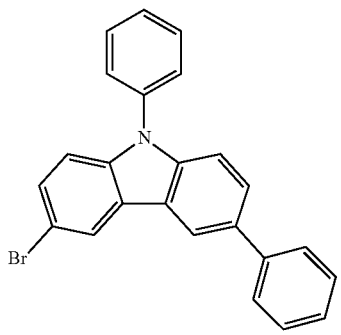
[1160294-85-8]]
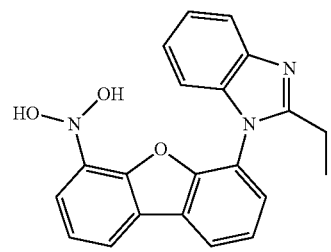 [SMILES: CCc1nc2ccccc2n1-c1cccc2c1oc1c(N(O)O)cccc12]
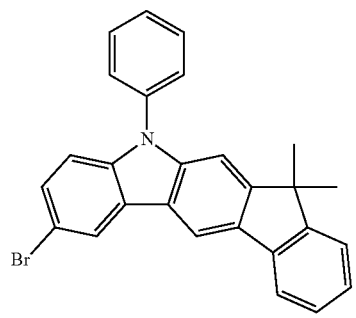
[1257220-44-2]
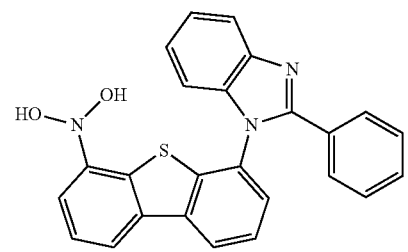 [SMILES: ON(O)c1cccc2c1sc1c(-n3c(-c4ccccc4)nc4ccccc43)cccc12]
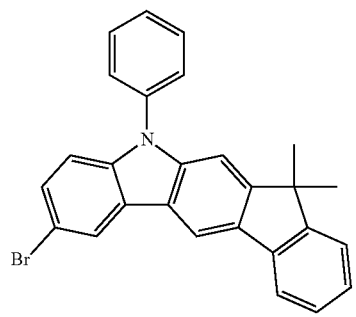
[1257220-44-2]
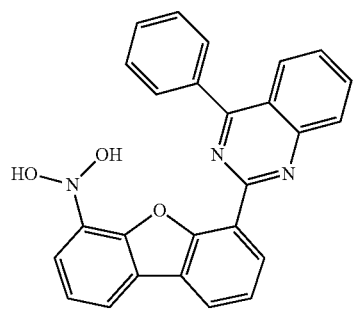 [SMILES: ON(O)c1cccc2c1oc1c(-c3nc(-c4ccccc4)c4ccccc4n3)cccc12]
| Product | Yield |
|---|---|
| | 81% |
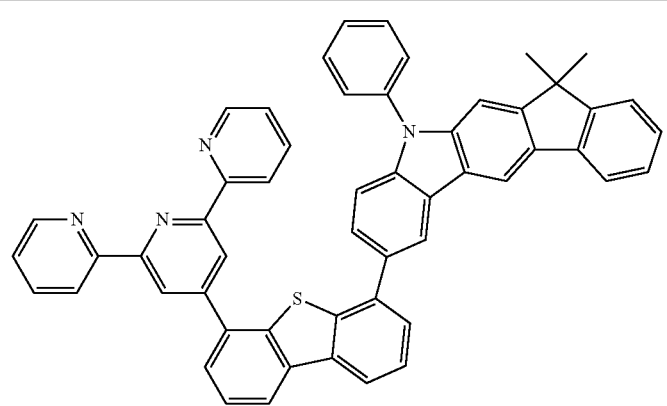 [SMILES: CC1(C)c2ccccc2-c2cc3c4cc(-c5cccc6c5sc5c(-c7cc(-c8ccccn8)nc(-c8ccccn8)c7)cccc56)ccc4n(-c4ccccc4)c3cc21]

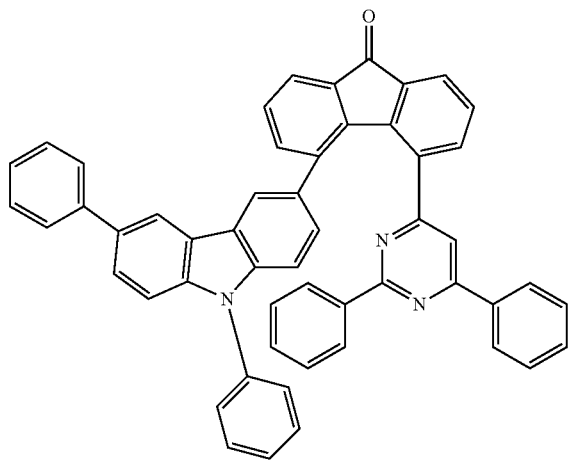 [SMILES: O=C1c2cccc(-c3ccc4c(c3)c3cc(-c5ccccc5)ccc3n4-c3ccccc3)c2-c2c1cccc2-c1cc(-c2ccccc2)nc(-c2ccccc2)n1]
79%
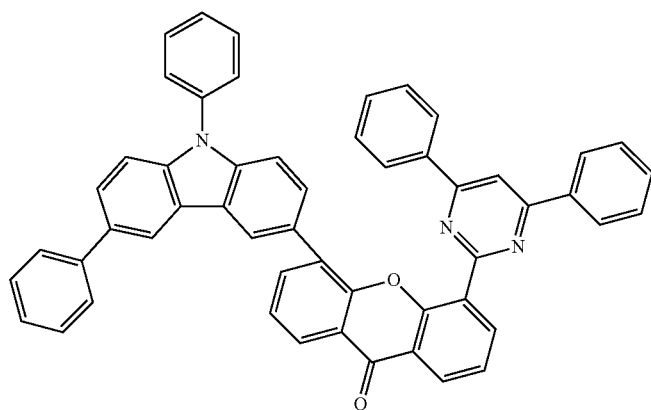 [SMILES: O=c1c2cccc(-c3ccc4c(c3)c3cc(-c5ccccc5)ccc3n4-c3ccccc3)c2oc2c(-c3nc(-c4ccccc4)cc(-c4ccccc4)n3)cccc12]
66%
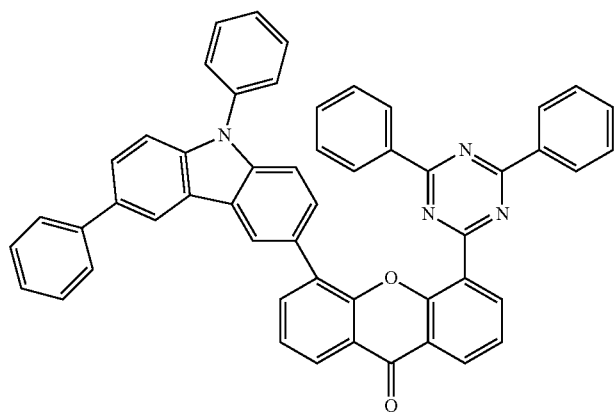 [SMILES: O=c1c2cccc(-c3ccc4c(c3)c3cc(-c5ccccc5)ccc3n4-c3ccccc3)c2oc2c(-c3nc(-c4ccccc4)nc(-c4ccccc4)n3)cccc12]
78%
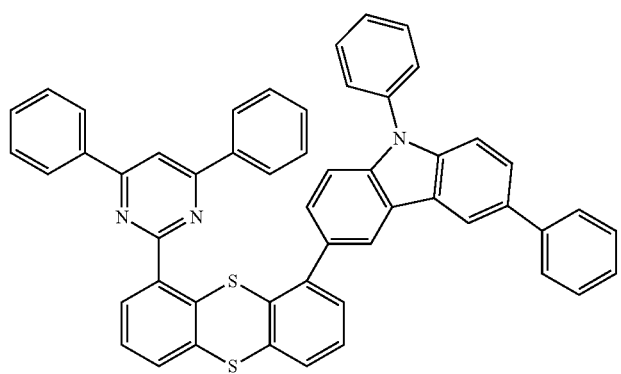 [SMILES: c1ccc(-c2ccc3c(c2)c2cc(-c4cccc5c4Sc4c(cccc4-c4nc(-c6ccccc6)cc(-c6ccccc6)n4)S5)ccc2n3-c2ccccc2)cc1]
77%

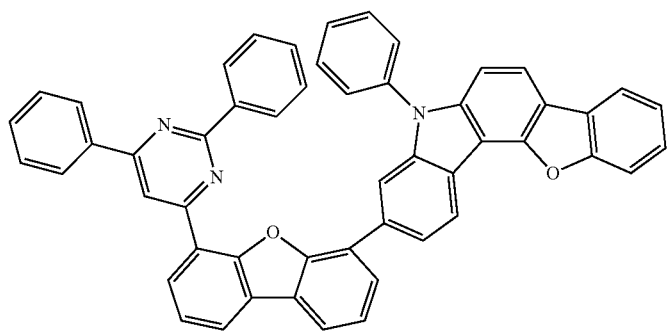 [SMILES: c1ccc(-c2cc(-c3cccc4c3oc3c(-c5ccc6c7c8oc9ccccc9c8ccc7n(-c7ccccc7)c6c5)cccc34)nc(-c3ccccc3)n2)cc1]
79%
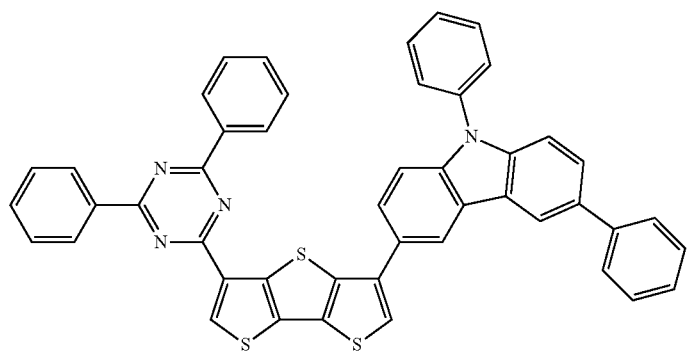 [SMILES: c1ccc(-c2ccc3c(c2)c2cc(-c4csc5c4sc4c(-c6nc(-c7ccccc7)nc(-c7ccccc7)n6)csc45)ccc2n3-c2ccccc2)cc1]
83%
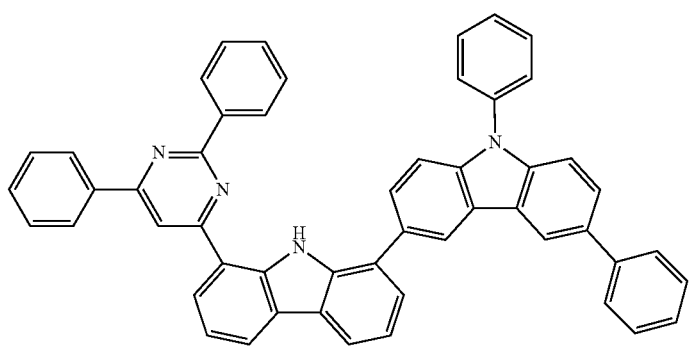 [SMILES: c1ccc(-c2ccc3c(c2)c2cc(-c4cccc5c4[nH]c4c(-c6cc(-c7ccccc7)nc(-c7ccccc7)n6)cccc45)ccc2n3-c2ccccc2)cc1]
83%
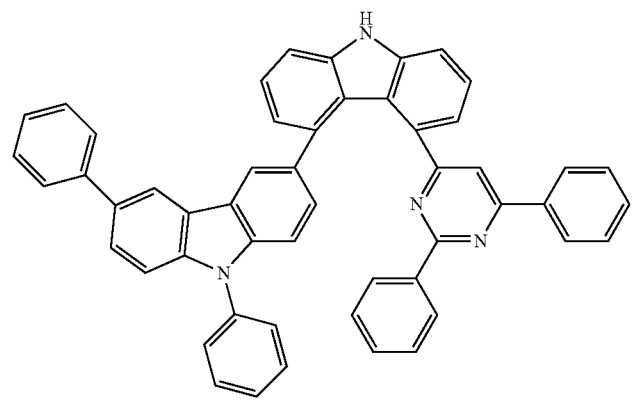 [SMILES: c1ccc(-c2ccc3c(c2)c2cc(-c4cccc5[nH]c6cccc(-c7cc(-c8ccccc8)nc(-c8ccccc8)n7)c6c45)ccc2n3-c2ccccc2)cc1]
74%

-continued
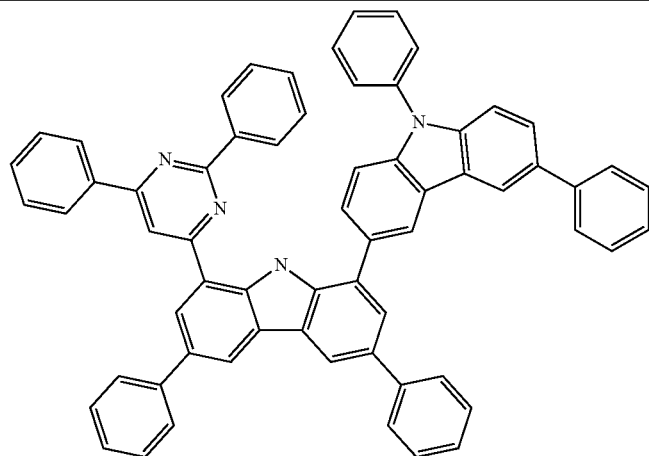
78%
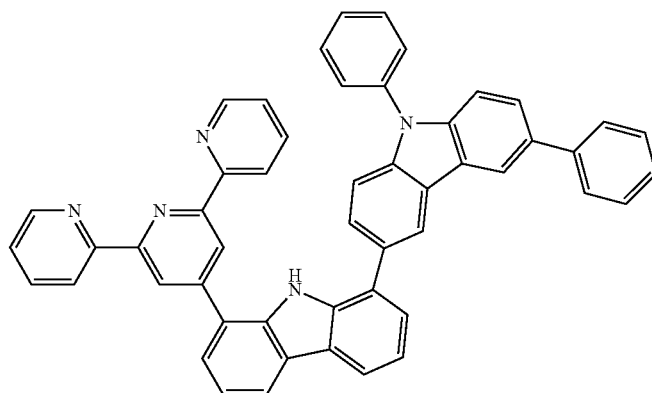
79%
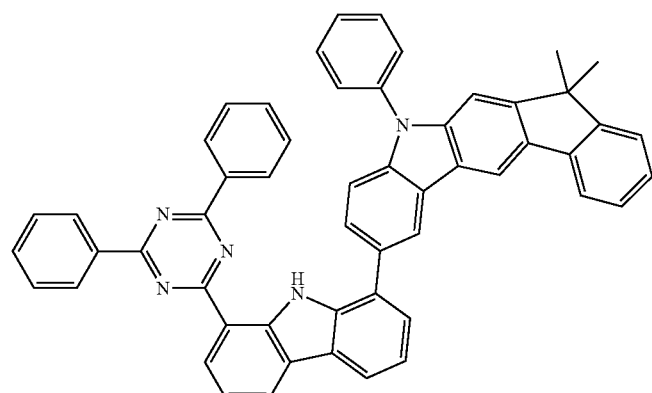
77%
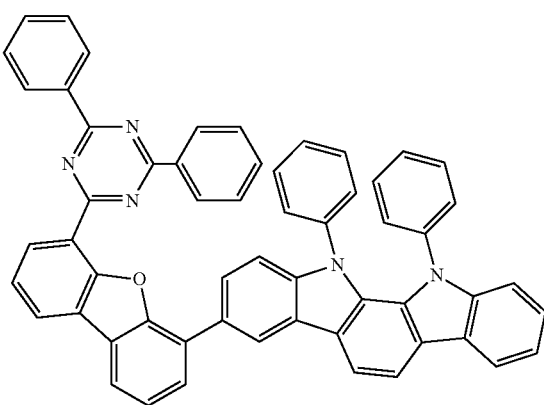 [SMILES: c1ccc(-c2nc(-c3ccccc3)nc(-c3cccc4c3oc3c(-c5ccc6c(c5)c5ccc7c8ccccc8n(-c8ccccc8)c7c5n6-c5ccccc5)cccc34)n2)cc1]
65%

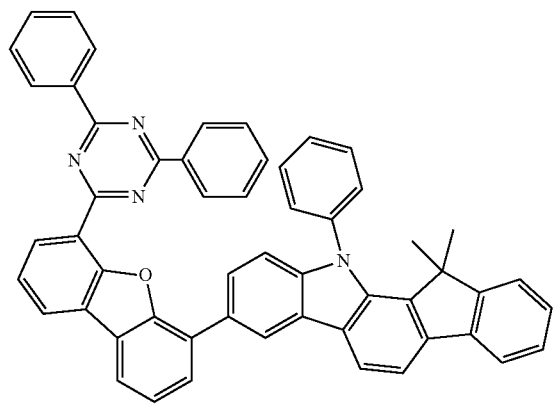 [SMILES: CC1(C)c2ccccc2-c2ccc3c4cc(-c5cccc6c5oc5c(-c7nc(-c8ccccc8)nc(-c8ccccc8)n7)cccc56)ccc4n(-c4ccccc4)c3c21]
69%
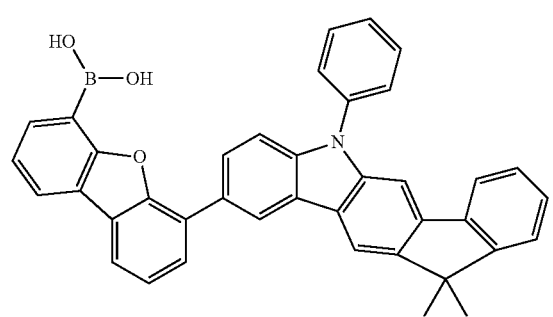 [SMILES: CC1(C)c2ccccc2-c2cc3c(cc21)c1cc(-c2cccc4c2oc2c(B(O)O)cccc24)ccc1n3-c1ccccc1]
69%
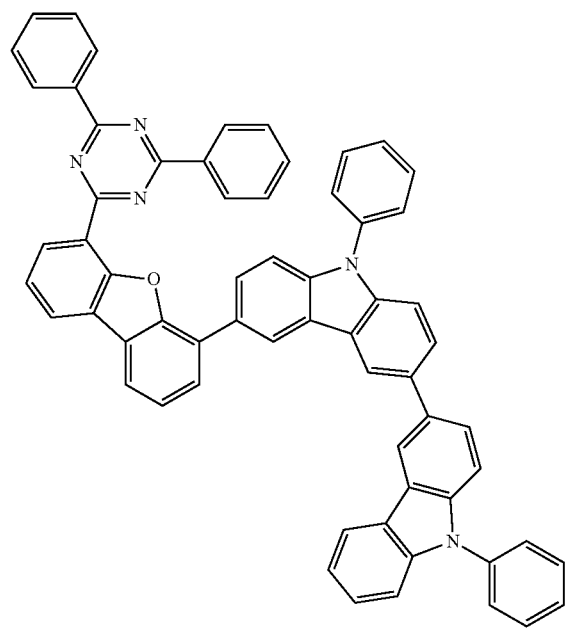 [SMILES: c1ccc(-c2nc(-c3ccccc3)nc(-c3cccc4c3oc3c(-c5ccc6c(c5)c5cc(-c7ccc8c(c7)c7ccccc7n8-c7ccccc7)ccc5n6-c5ccccc5)cccc34)n2)cc1]
71%

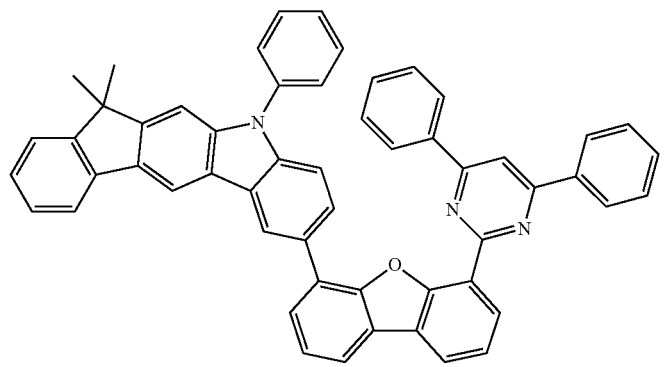 [SMILES: CC1(C)c2ccccc2-c2cc3c4cc(-c5cccc6c5oc5c(-c7nc(-c8ccccc8)cc(-c8ccccc8)n7)cccc56)ccc4n(-c4ccccc4)c3cc21]
79%
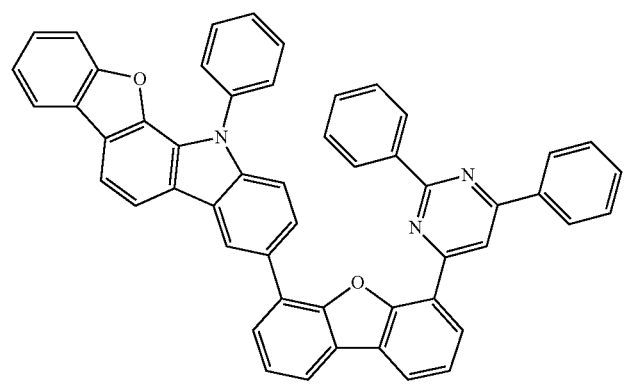 [SMILES: c1ccc(-c2cc(-c3cccc4c3oc3c(-c5ccc6c(c5)c5ccc7c8ccccc8oc7c5n6-c5ccccc5)cccc34)nc(-c3ccccc3)n2)cc1]
76%
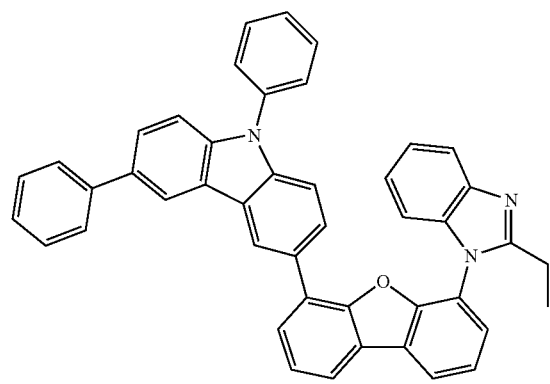 [SMILES: CCc1nc2ccccc2n1-c1cccc2c1oc1c(-c3ccc4c(c3)c3cc(-c5ccccc5)ccc3n4-c3ccccc3)cccc12]
83%
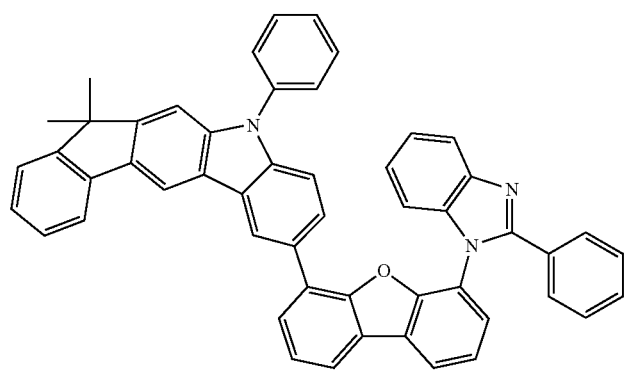 [SMILES: CC1(C)c2ccccc2-c2cc3c4cc(-c5cccc6c5oc5c(-n7c(-c8ccccc8)nc8ccccc87)cccc56)ccc4n(-c4ccccc4)c3cc21]
80%

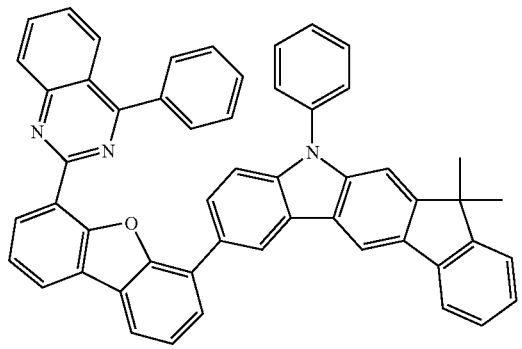 [SMILES: CC1(C)c2ccccc2-c2cc3c4cc(-c5cccc6c5oc5c(-c7nc(-c8ccccc8)c8ccccc8n7)cccc56)ccc4n(-c4ccccc4)c3cc21]

81%

Example 7

Synthesis of 3-[6-(4,6-diphenyl-1,3,5-triazin-2-yl)dibenzofuran-4-yl]-6,9-diphenyl-9H-carbazole

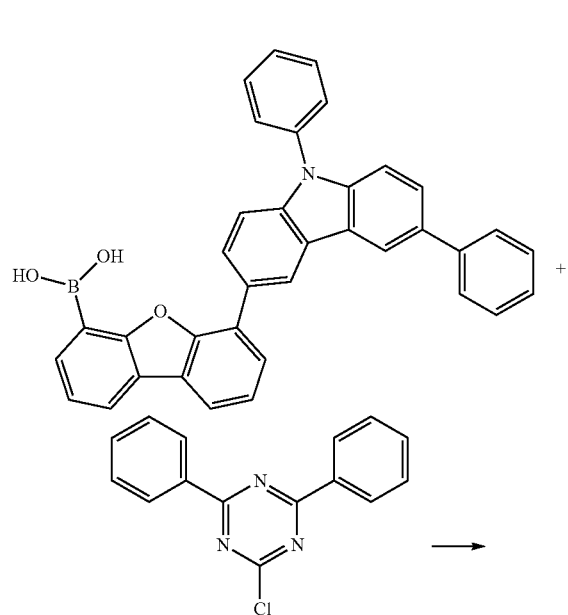

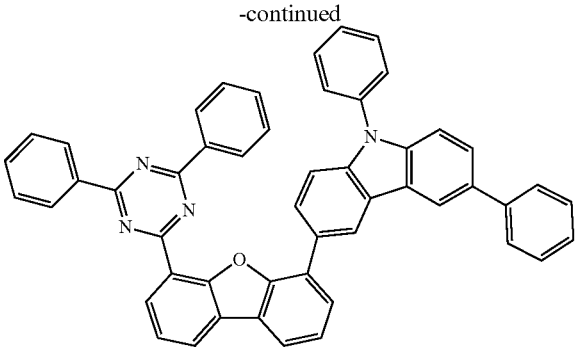

37 g (70 mmol) of 6-(3,9-diphenyl-9H-carbazol-3-yl)-4-dibenzofuranyl-boronic acid, 18.8 g (70 mmol) of 2-chloro-4,6-diphenyl-1,3,5-triazine, 78.9 ml (158 mmol) of $Na_2CO_3$ (2 M solution) are suspended in 120 ml of ethanol and 100 ml of water. 1.3 g (1.1 mmol) of $Pd(PPh_3)_4$ are added to this suspension, and the reaction mixture is heated under reflux for 16 h. After the mixture has been cooled, dichloromethane is added, and the organic phase is separated off and filtered through silica gel. The yield is 41 g (58 mmol), corresponding to 83% of theory. The residue is recrystallised from toluene and finally sublimed in a high vacuum (p=5×10$^{-5}$ mbar). The purity is 99.9%.

The following compounds can be obtained analogously.

| Starting material 1 | Starting material 2 |
|---|---|
| 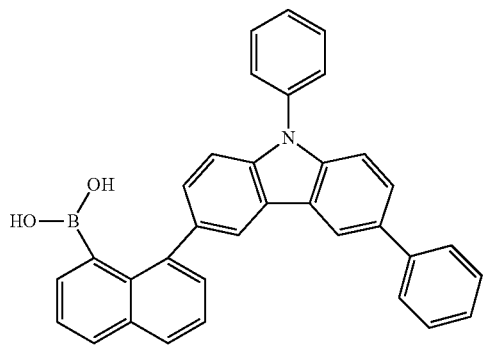 [SMILES: OB(O)c1cccc2cccc(-c3ccc4c(c3)c3cc(-c5ccccc5)ccc3n4-c3ccccc3)c12] | 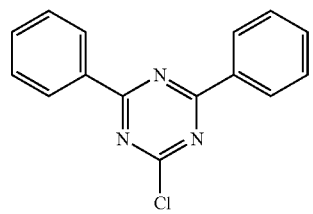  [3842-55-5] |

-continued
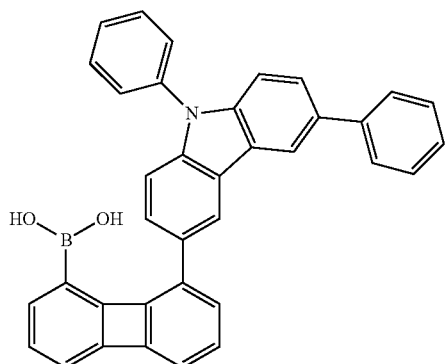 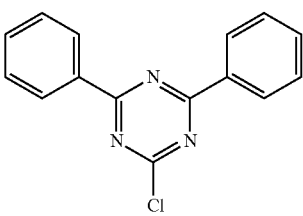
[3842-55-5]
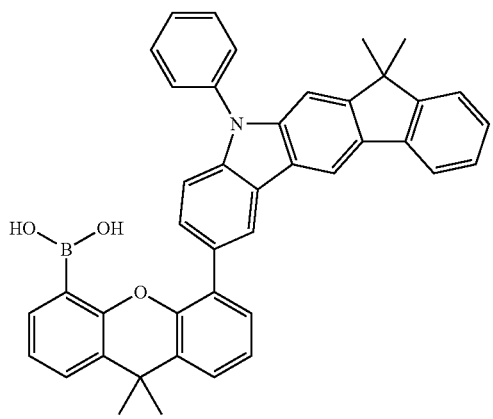 [SMILES: CC1(C)c2ccccc2-c2cc3c4cc(-c5cccc6c5Oc5c(B(O)O)cccc5C6(C)C)ccc4n(-c4ccccc4)c3cc21] 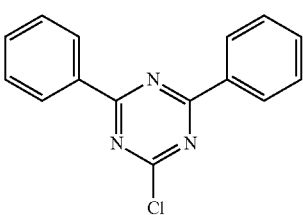
[3842-55-5]
| Product | Yield |
|---|---|
| 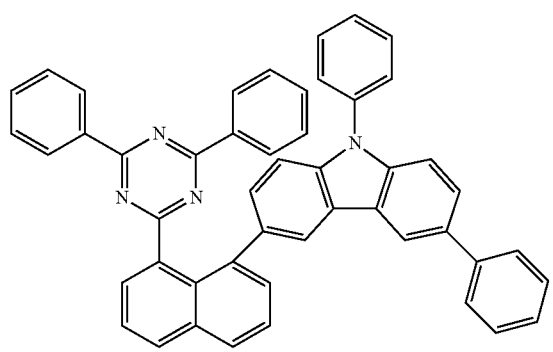 [SMILES: c1ccc(-c2ccc3c(c2)c2cc(-c4cccc5cccc(-c6nc(-c7ccccc7)nc(-c7ccccc7)n6)c45)ccc2n3-c2ccccc2)cc1] | 59% |
| 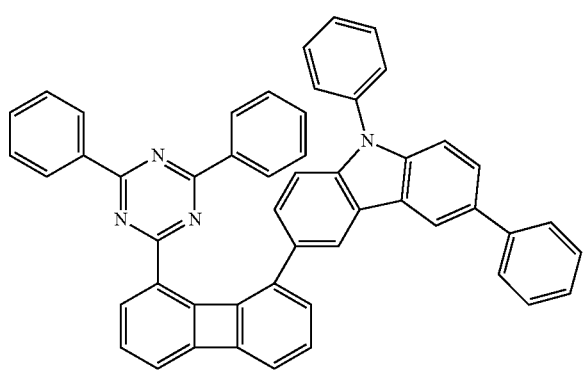 [SMILES: c1ccc(-c2ccc3c(c2)c2cc(-c4cccc5c4-c4c(-c6nc(-c7ccccc7)nc(-c7ccccc7)n6)cccc4-5)ccc2n3-c2ccccc2)cc1] | 67% |

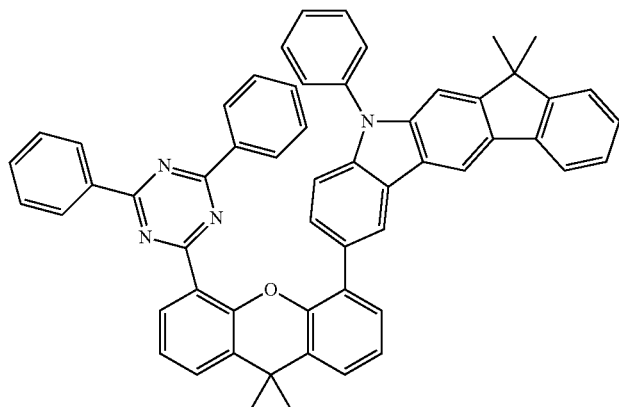 [SMILES: CC1(C)c2ccccc2-c2cc3c4cc(-c5cccc6c5Oc5c(-c7nc(-c8ccccc8)nc(-c8ccccc8)n7)cccc5C6(C)C)ccc4n(-c4ccccc4)c3cc21]

68%

Example 8

Synthesis of 8-(4,6-diphenyl-1,3,5-triazin-2-yl)-9,6',9'-triphenyl-9H,9'H-[1,2']bicarbazolyl

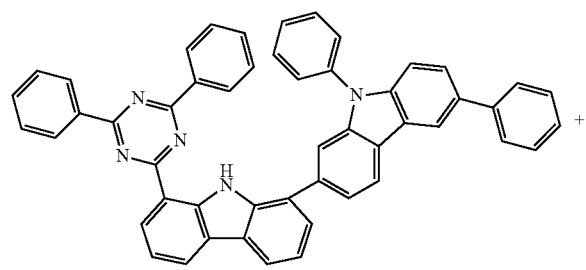
+
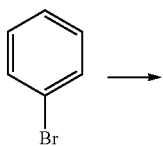
→
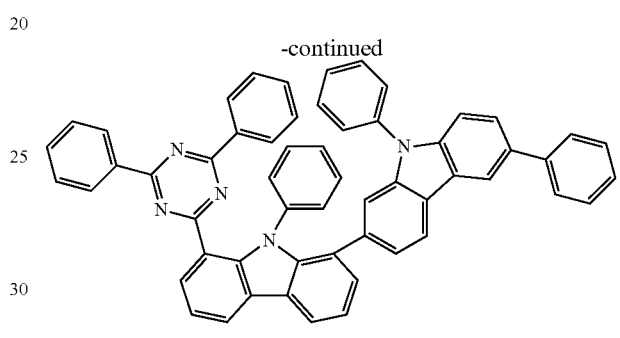

50.4 g (70.58 mmol) of 8-(4,6-diphenyl-1,3,5-triazin-2-yl)-6',9'-diphenyl-9H,9'H-[1,2']bicarbazolyl and 16.4 g (105.87 mmol) of bromobenzene are dissolved in toluene, and the mixture is degassed by introduction of a protective gas. 7 ml (7 mmol, 1 M solution in toluene) of tri-tert-butylphos-phine, 633.8 mg (2.82 mmol) of Pd(OAc)$_2$ and 10.2 g (105.87 mmol) of NaOtBu are subsequently added. The solids are degassed in advance, and the reaction mixture is subsequently degassed and then stirred under reflux for 3 h. The warm reaction solution is filtered through aluminium oxide B (activity grade 1), washed with water, dried and evaporated. The yield is 44 g (55 mmol), corresponding to 79% of theory. The residue is recrystallised from toluene and finally sublimed in a high vacuum (p=5×10$^{-5}$ mbar). The purity is 99.9%.

The following compounds can be obtained analogously.

| Starting material 1 | Starting material 2 |
|---|---|
| 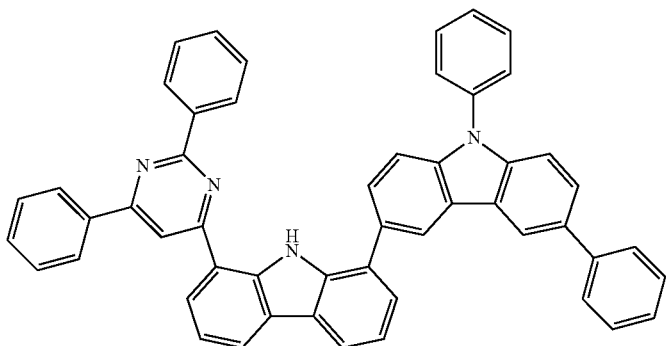 [SMILES: c1ccc(-c2ccc3c(c2)c2cc(-c4cccc5c4[nH]c4c(-c6cc(-c7ccccc7)nc(-c7ccccc7)n6)cccc45)ccc2n3-c2ccccc2)cc1] | 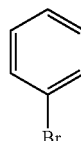 |

-continued
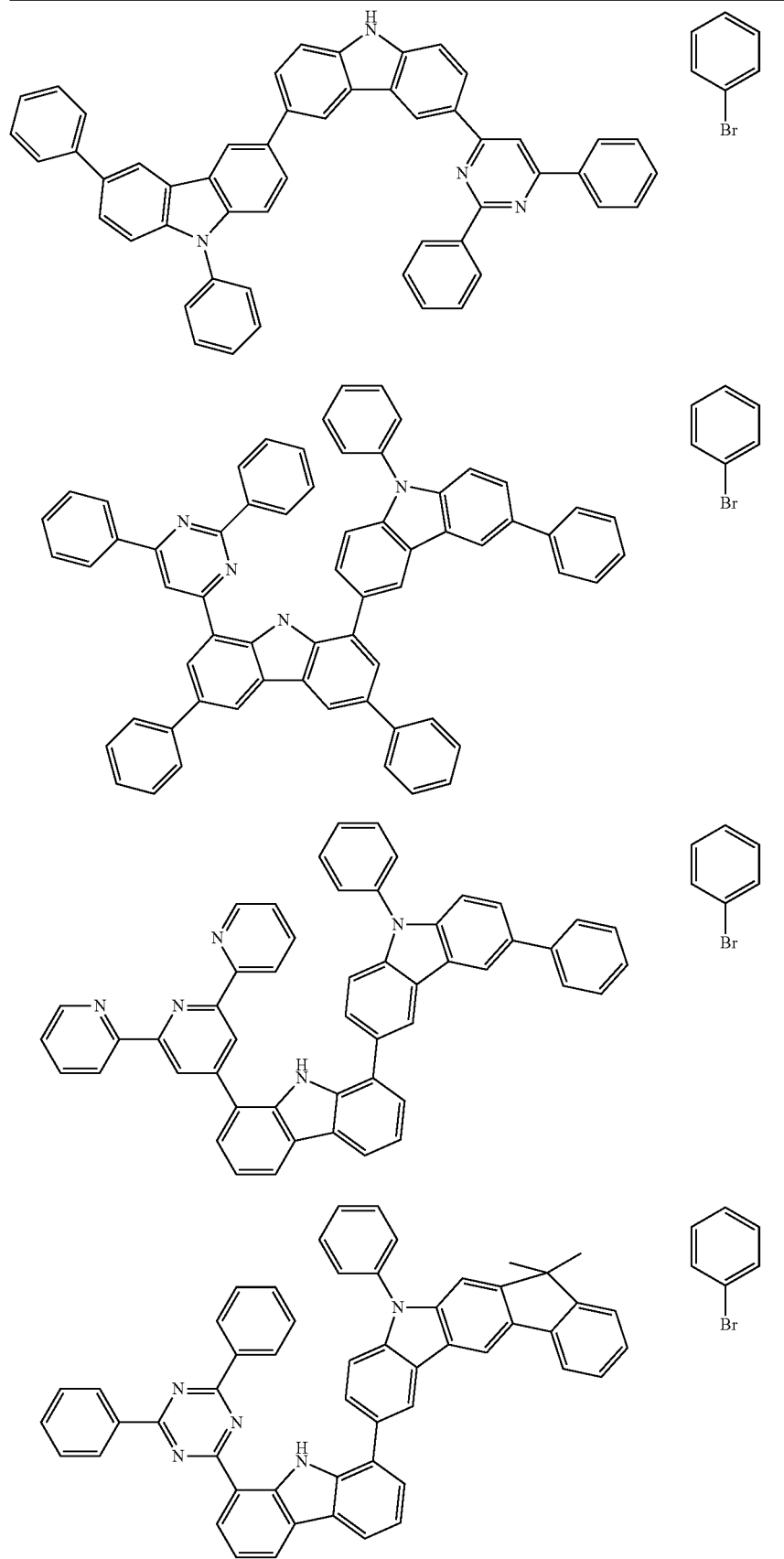

-continued
| Product | Yield |
|---|---|
| 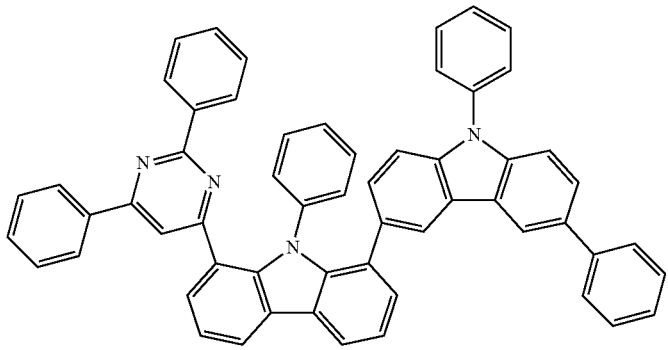 [SMILES: c1ccc(-c2ccc3c(c2)c2cc(-c4cccc5c6cccc(-c7cc(-c8ccccc8)nc(-c8ccccc8)n7)c6n(-c6ccccc6)c45)ccc2n3-c2ccccc2)cc1] | 79% |
| 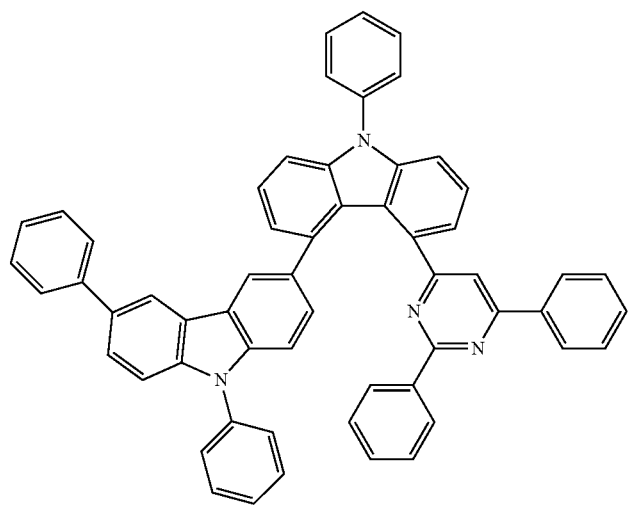 [SMILES: c1ccc(-c2ccc3c(c2)c2cc(-c4cccc5c4c4c(-c6cc(-c7ccccc7)nc(-c7ccccc7)n6)cccc4n5-c4ccccc4)ccc2n3-c2ccccc2)cc1] | 80% |
| 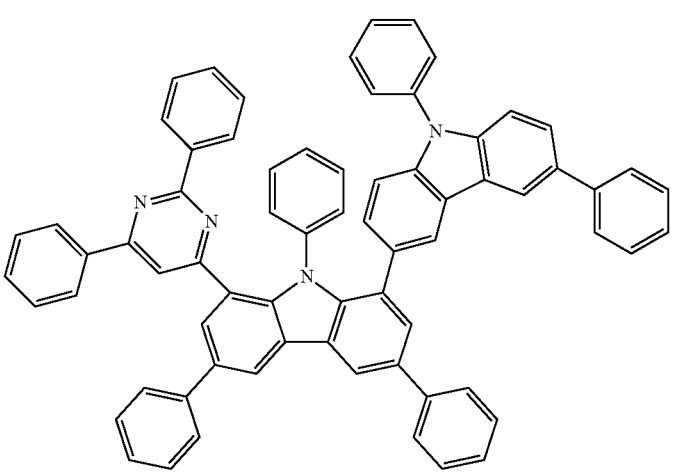 [SMILES: c1ccc(-c2ccc3c(c2)c2cc(-c4cc(-c5ccccc5)cc5c6cc(-c7ccccc7)cc(-c7cc(-c8ccccc8)nc(-c8ccccc8)n7)c6n(-c6ccccc6)c45)ccc2n3-c2ccccc2)cc1] | 80% |

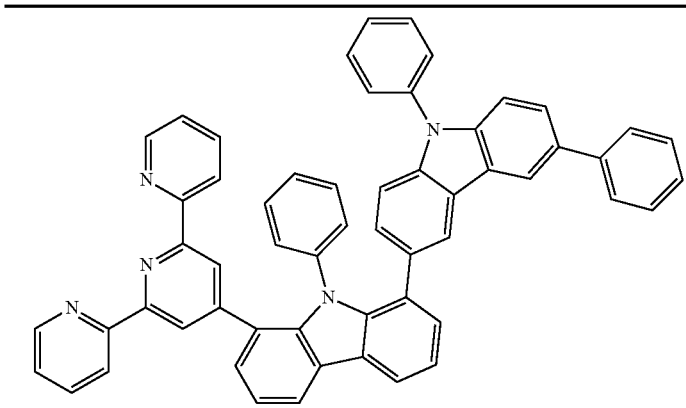

70%

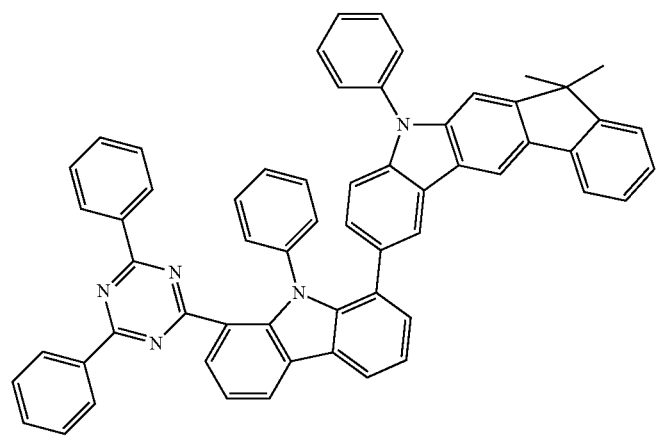 [SMILES: CC1(C)c2ccccc2-c2cc3c4cc(-c5cccc6c7cccc(-c8nc(-c9ccccc9)nc(-c9ccccc9)n8)c7n(-c7ccccc7)c56)ccc4n(-c4ccccc4)c3cc21]

69%

Example 10 (Comparison)

Synthesis of 3-(4-[6-(4,6-diphenyl-1,3,5-triazin-2-yl)dibenzofuran-4-yl]-phenyl)-9-phenyl-9H-carbazole a) Synthesis of 2-(6-bromodibenzofuran-4-yl)-4,6-diphenyl-1,3,5-triazine

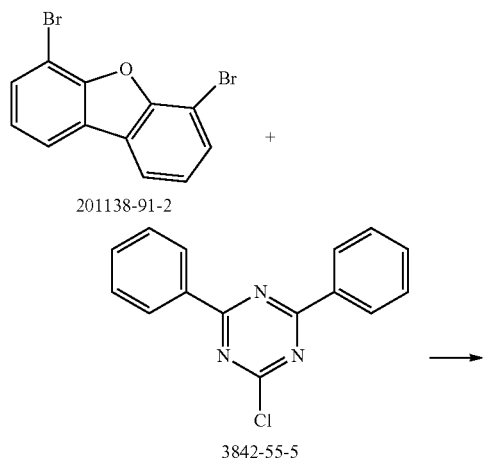

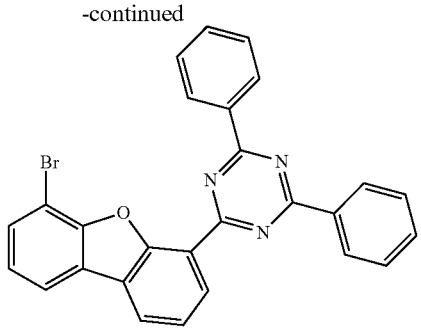

80 g (245 mmol) of 4,6-dibromodibenzofuran are dissolved in 500 ml of dried THF in a flask which has been dried by heating. The reaction mixture is cooled to −78° C. 57 ml of a 1.9 M solution of n-phenyllithium in dibutyl ether (115 mmol) are slowly added dropwise at this temperature. The batch is stirred at −73° C. for a further 1 hour. 65 g of 2-chloro-4,6-diphenyl-1,3,5-triazine (245 mmol) are subsequently dissolved in 150 ml of THF and added dropwise at −70° C. When the addition is complete, the reaction mixture is slowly warmed to room temperature, stirred at room temperature overnight, quenched with water and subsequently evaporated in a rotary evaporator, during which a white solid precipitates out. The batch is then cooled to room temperature, and the solid which has precipitated out is filtered off with suction and rinsed with methanol. The yield is 40 g (84 mmol), corresponding to 34% of theory.

b) Synthesis of 3-{4-[6-(4,6-diphenyl-1,3,5-triazin-2-yl)dibenzofuran-4-yl]phenyl}-9-phenyl-9H-carbazole

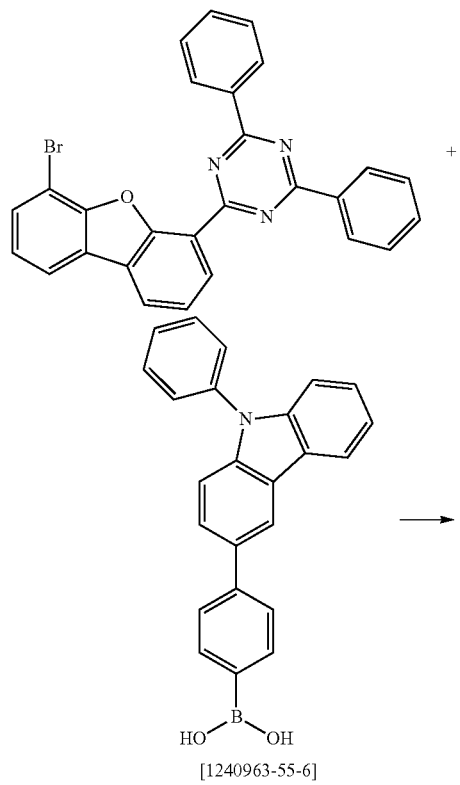

[1240963-55-6]

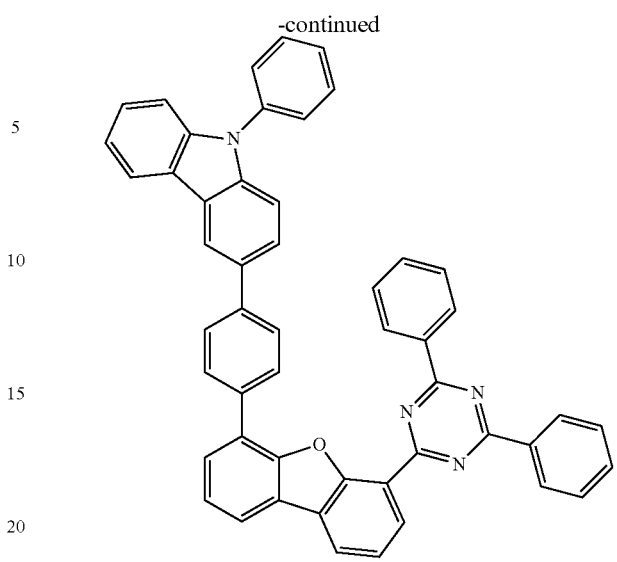

33.4 g (70 mmol) of 2-(6-bromodibenzofuran-4-yl)-4,6-diphenyl-1,3,5-triazine, 25.4 g (70 mmol) of 4-(9-phenyl-9H-carbazol-3-yl)phenylboromic acid, 78.9 ml (158 mmol) of Na$_2$CO$_3$(2 M solution) are suspended in 120 ml of ethanol and 100 ml of water. 1.3 g (1.1 mmol) of Pd(PPh$_3$)$_4$ are added to this suspension, and the reaction mixture is heated under reflux for 16 h. After the mixture has been cooled, dichloromethane is added, and the organic phase is separated off, filtered through silica gel and recrystallised from toluene. The yield is 40 g (56 mmol), corresponding to 80% of theory.

The following compound can be prepared analogously.

| Starting material 1 | Starting material 2 |
|---|---|//

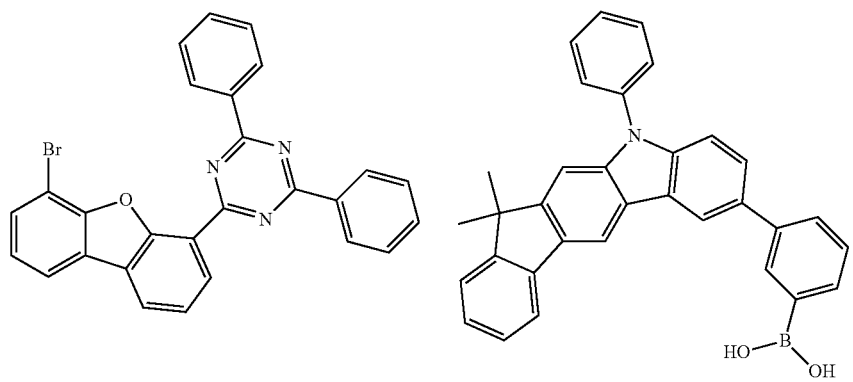

[1436854-43-1]

| Product | Yield |
|---|---|
|  | 86% |

Example 11 (Comparison)

Synthesis of 3-(7-[4-(4,6-diphenyl-1,3,5-triazin-2-yl)phenyl]dibenzo-furan-4-yl)-9-phenyl-9H-carbazole a) Preparation of 2-(4-dibenzofuran-3-ylphenyl)-4,6-diphenyl-1,3,5-triazine

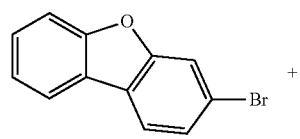

26608-06-0

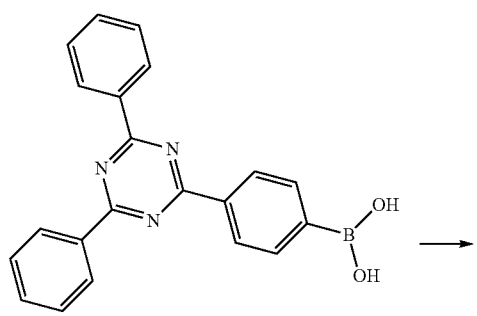

1313018-07-3

→

-continued

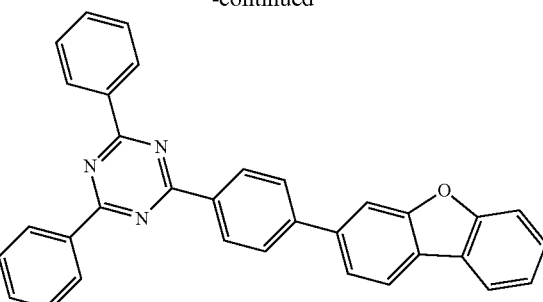

24 g (70 mmol) of 4-(4,6-diphenyl-1,3,5-triazin-2-yl)phenyl) boronic acid, 17.3 g (70 mmol) of 3-bromodibenzofuran, 78.9 ml (158 mmol) of $Na_2CO_3$ (2 M solution) are suspended in 120 ml of ethanol and 100 ml of water. 1.3 g (1.1 mmol) of $Pd(PPh_3)_4$ are added to this suspension, and the reaction mixture is heated under reflux for 16 h. After the mixture has been cooled, dichloromethane is added, and the organic phase is separated off, filtered through silica gel and recrystallised from toluene. The yield is 28 g (58 mmol), corresponding to 86% of theory.

The following compound can be prepared analogously.

| Starting material 1 | Starting material 2 | Product | Yield |
|---|---|---|---|
| 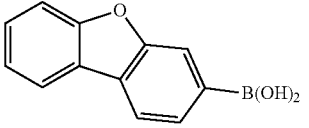 395087-89-5 | 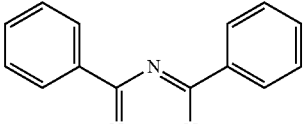 [3842-55-5] | 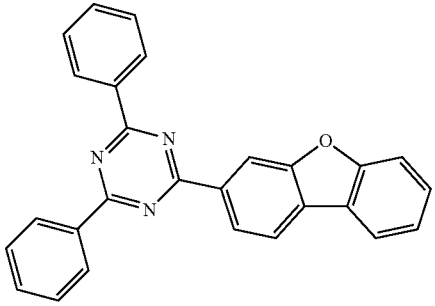 [SMILES: c1ccc(-c2nc(-c3ccccc3)nc(-c3ccc4c(c3)oc3ccccc34)n2)cc1] | 87% | b) Synthesis of 2,4-diphenyl-6-[4-(6-trimethylsilanyldibenzofuran-3-yl)-phenyl]-1,3,5 triazine

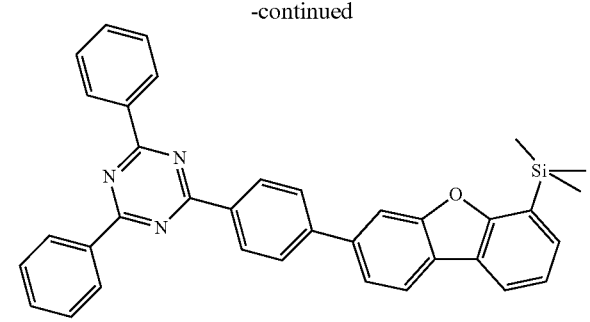

-continued

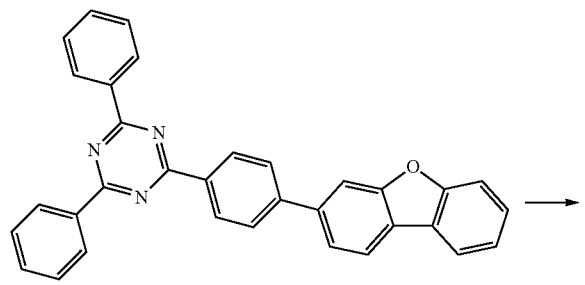

127 ml (225.4 mmol) of n-buthyllithium (2.5 M in hexane) are added dropwise to a solution, cooled to 20° C., of 57.4 g (121 mmol) of 2-(4-dibenzo-furan-3-ylphenyl)-4,6-diphenyl-1,3,5 triazine and 28 g (242 mmol) of TMEDA in 1000 ml of THF. The reaction mixture is stirred at room temperature for 3 h, then cooled to 0° C., and 26 g (242 mmol) of chlorotrimetylsilane are added dropwise over the course of 30 min. The mixture is stirred at room temperature for 8 h. The solvent is subsequently removed in vacuo, and the residue is purified by chromatography on silica gel with chloroform as eluent. Yield: 41 g (74 mmol), 63% of theory.

The following compound can be prepared analogously.

| Starting material 1 | Product | Yield |
|---|---|---|
| 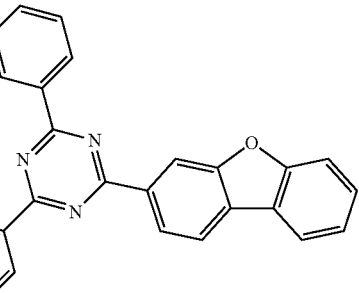 | 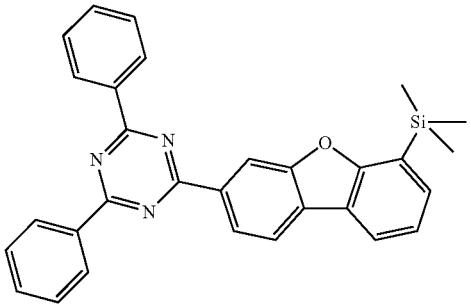 [SMILES: C[Si](C)(C)c1cccc2c1oc1cc(-c3nc(-c4ccccc4)nc(-c4ccccc4)n3)ccc12] | 87% | c) Synthesis of 3-[4-(4,6-diphenyl-1,3,5-triazin-2-yl)phenyl]dibenzo-furan-6-boronic acid

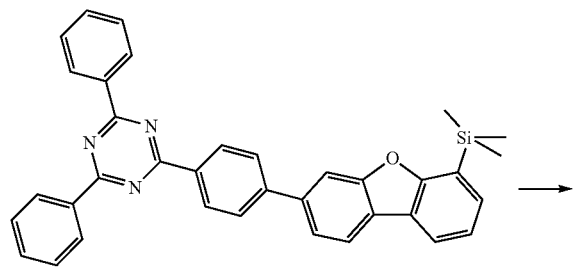

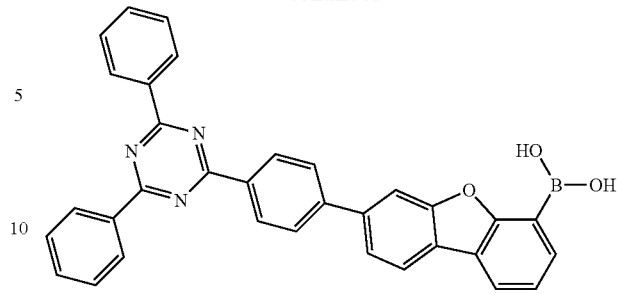

21 g (86 mmol) of bromine tribromide are added dropwise under protective gas to a solution of 39 g of 2,4-diphenyl-6-[4-(6-trimethylsilanyldibenzo-furan-3-yl)phenyl]-1,3,5-triazine in 500 ml of dichloromethane, and the mixture is stirred at room temperature for 10 h. A little water is then slowly added to the mixture, and the residue which precipitates out is filtered off and washed with heptane. The yield is 32 g (62 mmol), corresponding to 87% of theory.

The following compound can be prepared analogously.

| Starting material 1 | Product | Yield |
|---|---|---|
|  |  | 90% | d) Synthesis of 3-(7-[4-(4,6-diphenyl-1,3,5-triazin-2-yl)phenyl]-dibenzofuran-4-yl)-6,9-diphenyl-9H-carbazoles

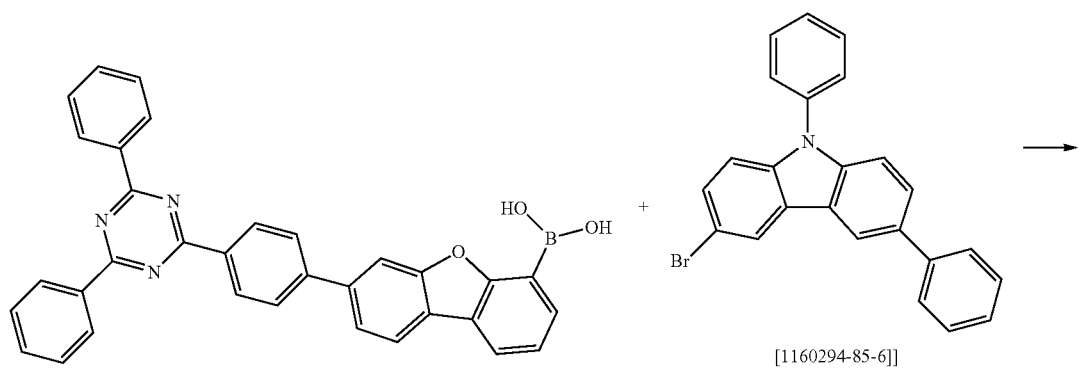

[1160294-85-6]

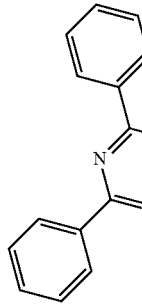

36 g (70 mmol) of 3-[4-(4,6-diphenyl-1,3,5-triazin-2-yl)]phenyl]dibenzo-furan-6-boronic acid 27 g (70 mmol) of 3-bromo-6,9-diphenyl-9H-carbazole and 78.9 ml (158 mmol) of $Na_2CO_3$ (2 M solution) are suspended in 120 ml of ethanol and 100 ml of water. 1.3 g (1.1 mmol) of $Pd(PPh_3)_4$ are added to this suspension, and the reaction mixture is heated under reflux for 16 h. After the mixture has been cooled, dichloromethane is added, and the organic phase is separated off, filtered through silica gel and recrystallised from toluene. The residue is recrystallised from toluene and finally sublimed in a high vacuum (p=$5\times10^{-5}$ mbar). The yield is 36 g (53 mmol), corresponding to 80% of theory.

The following compound can be prepared analogously,

| Starting material 1 | Starting material 2 |
|---|---|
| 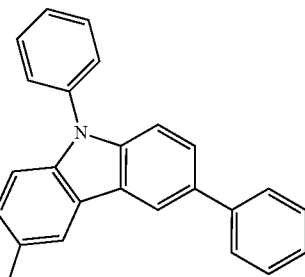 | |

[1160294-85-5]

| Product | Yield |
|---|---|
| | 86% |

Example 12

Synthesis of
3-dibenzofuran-4-yl-9-phenyl-9H-carbazole

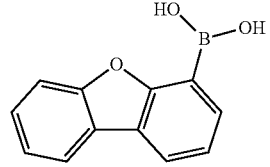

[89827-45-2]

+

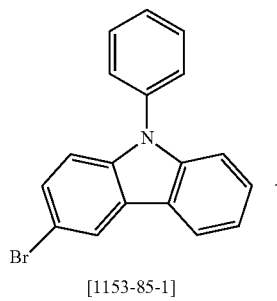

[1153-85-1]

→

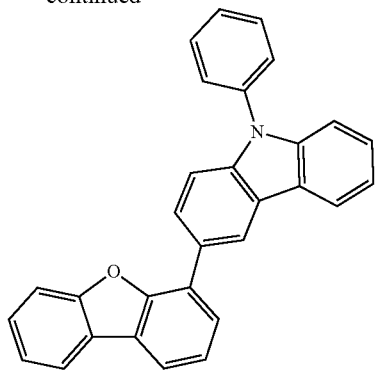

28.9 g (136 mmol) of dibenzofuran-4-boronic acid, 40 g (124.1 mmol) of 3-bromo-9-phenyl-9H-carbazoles and 78.9 ml (158 mmol) of $Na_2CO_3$ (2 M solution) are suspended in 120 ml of toluene, 120 ml of ethanol and 100 ml of water. 2.6 g (2.2 mmol) of $Pd(PPh_3)_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 49.7 g (121 mmol), corresponding to 97% of theory.

The following compound can be obtained analogously:

| Starting material 1 | Starting material 2 | Product | Yield |
|---|---|---|---|
| [89827-45-2] | [3842-55-5] | | 69% |

Example 13

Synthesis of 9-phenyl-3-(6-trimethylsilanyldibenzo-furan-4-yl)-9H-carbazole

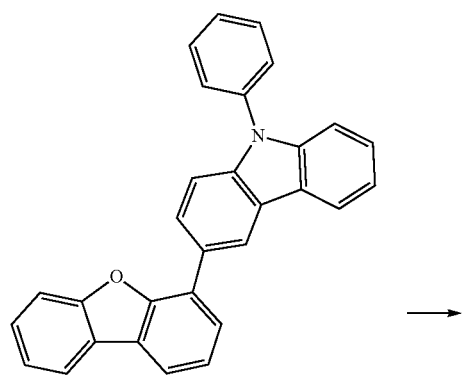

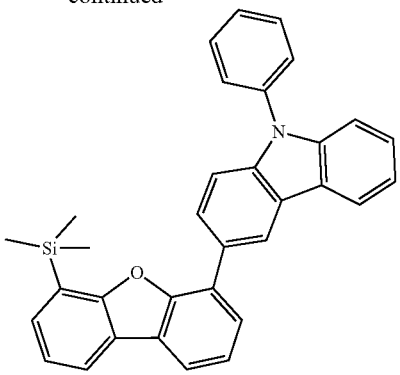

127 ml (225.4 mmol) of n-buthyllithium (2.5 M in hexane) are added dropwise to a solution, cooled to 20° C., of 49 g (121 mmol) of 3-dibenzofuran-4-yl-9-phenyl-9H-carbazole and 28 g (242 mmol) of TMEDA in 1000 ml of THF. The reaction mixture is stirred at room temperature for 3 h, then cooled to 0° C., and 26 g (242 mmol) of chlorotrimetylsilane are added dropwise over the course of 30 min., and the mixture is stirred at room temperature for 8 h. The solvent is subsequently removed in vacuo, and the residue is purified by chromatography on silica gel with chloroform as eluent. Yield: 34 g (72 mmol), 60% of theory.

The following compounds can be obtained analogously.

| Starting material 1 | Product | Yield |
|---|---|---|
| 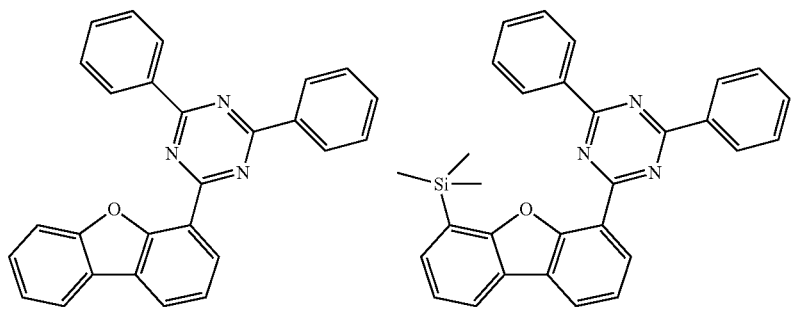 | | 65% |
| 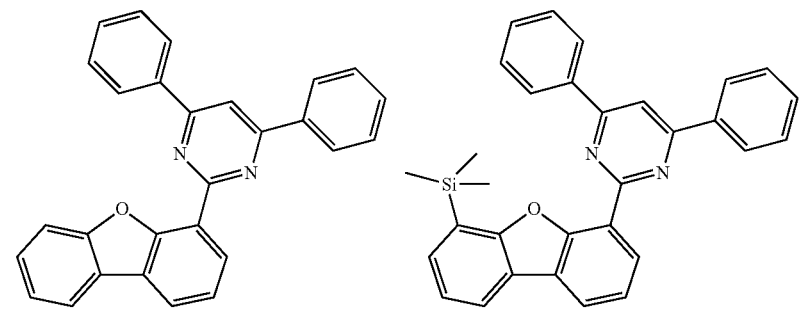 | | 64% |

Example 14

Synthesis of B-[6-(phenyl-9H-carbazol-3-yl)-4-benzofuranyl]boronic acid

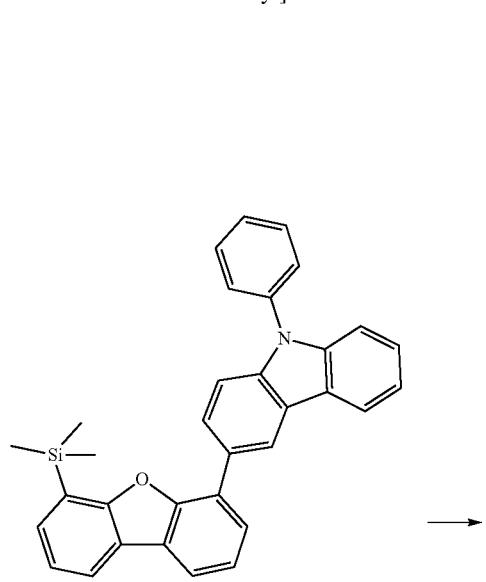

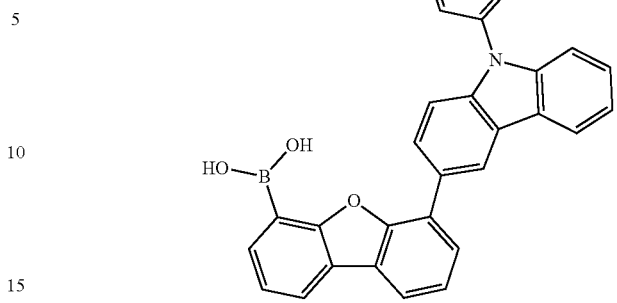

21 g (86 mmol) of bromine tribromide are added dropwise under protective gas to a solution of 34 g (72 mmol) of B-[6-(phenyl-9H-carbazol-3-yl)-4-dibenzofuranyl]boronic acid in 500 ml of dichloromethane, and the mixture is stirred at room temperature for 10 h. A little water is then slowly added to the mixture, and the residue which precipitates out is filtered off and washed with heptane. The yield is 28 g (62 mmol), corresponding to 86% of theory.

The following compounds can be obtained analogously.

| Starting material 1 | Product | Yield |
|---|---|---|
|  |  | 69% |
|  |  | 78% |

Example 15

Synthesis of 10-(6-bromodibenzofuran-4-yl)-7-phenyl-7H-12-thia-7-azaindeno[1,2-a]fluorene

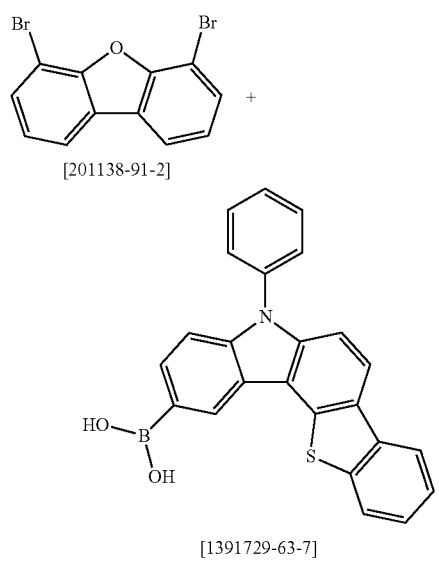

[201138-91-2]

[1391729-63-7]

→

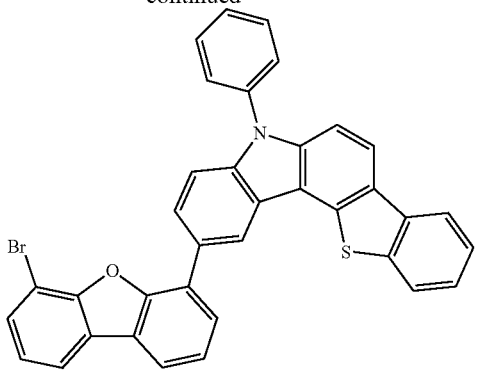

12.5 g (32 mmol) of 5-phenyl-5H[1]benzothieno[3,2-c]carbazol-3-ylboronic acid, 8.9 g (31.6 mmol) of 4,6-dibromodibenzofuran, 31 ml (63 mmol) of $Na_2CO_3$ (2 M solution) are suspended in 120 ml of toluene, 120 ml of ethanol. 0.73 g (0.63 mmol) of $Pd(PPh_3)_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 13.3 g (22 mmol), corresponding to 73% of theory.

The following compounds can be obtained analogously

| Starting material 1 | Starting material 2 |
|---|---|
| 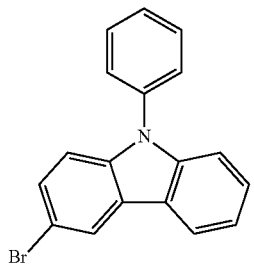 [SMILES: Brc1ccc2c(c1)c1ccccc1n2-c1ccccc1] | 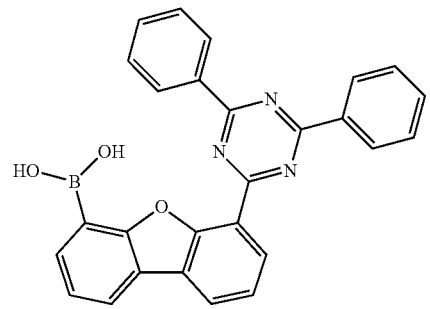 [SMILES: OB(O)c1cccc2c1oc1c(-c3nc(-c4ccccc4)nc(-c4ccccc4)n3)cccc12] |
| 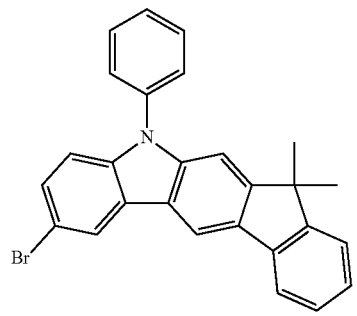<br>[1257220-44-2] | 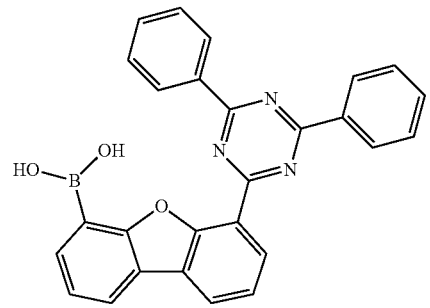 [SMILES: OB(O)c1cccc2c1oc1c(-c3nc(-c4ccccc4)nc(-c4ccccc4)n3)cccc12] |

| Product | Yield |
|---|---|
| 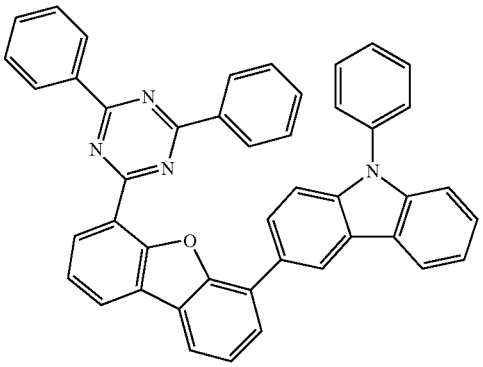 [SMILES: c1ccc(-c2nc(-c3ccccc3)nc(-c3cccc4c3oc3c(-c5ccc6c(c5)c5ccccc5n6-c5ccccc5)cccc34)n2)cc1] | 87% |
| 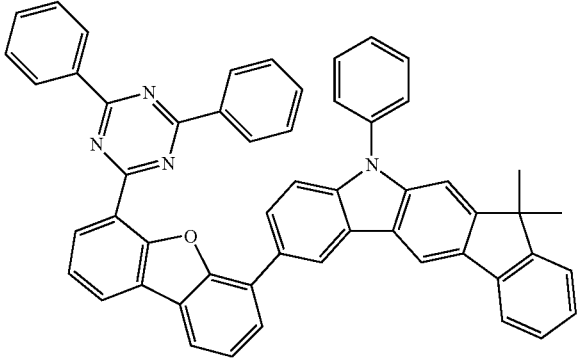 [SMILES: CC1(C)c2ccccc2-c2cc3c4cc(-c5cccc6c5oc5c(-c7nc(-c8ccccc8)nc(-c8ccccc8)n7)cccc56)ccc4n(-c4ccccc4)c3cc21] | 89% |

Example 16

Production and Characterisation of the OLEDs

The data of various OLEDs are presented in the following examples V1-V7 and E1-E23 (see Tables 1 and 2).

Pretreatment for Examples V1-E23: Glass plates which have been coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied.

The OLEDs have in principle the following layer structure: substrate/hole-transport layer (HTL)/interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum cham-ber. The emission layer here always consists of at least one matrix material (host material) and an emitting dopant (emitter), which are admixed with the matrix material or matrix materials in a certain proportion by volume by co-evaporation. An expression such as IC1:IC3:TEG1 (55%:35%:10%) here means that material IC1 is present in the layer in a proportion by volume of 55%, IC3 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordi-nates are calculated therefrom. The term U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$. The lifetime LT is defined as the time after which the luminous density drops to a certain proportion L1 from the initial luminous density on operation at constant current. An expression of L0;j0=4000 cd/m$^2$ and L1=70% in Table 2 means that the lifetime indicated in column LT corresponds to the time after which the initial luminous density drops from 4000 cd/m$^2$ to 2800 cd/m$^2$. Analogously, L0;j0=20 mA/cm$^2$, L1=80%, means that the luminous density drops to 80% of its initial value after time LT on operation at 20 mA/cm$^2$.

The data of the various OLEDs are summarised in Table 2. Examples V1-V7 are comparative examples in accordance with the prior art, Examples E1-E23 show data of OLEDs according to the invention.

Some of the examples are explained in greater detail below in order to illustrate the advantages of the OLEDs according to the invention.

Use of Mixtures According to the Invention in the Emission Layer of Phosphorescent OLEDs The materials according to the invention give rise to significant improvements over the prior art in all parameters, especially with respect to lifetime and external quantum efficiency, on use as matrix materials in phosphorescent OLEDs.

The use of compounds FF1 and FF2 according to the invention in combination with the green-emitting dopant TEG1 enables an increase in the lifetime by about 3040% compared with the prior art StdT1 and StdT2 to be observed (Examples V1, E1 and V2, E2). Furthermore, compound FF3 according to the invention enables an external quantum efficiency which is increased by about 25% compared with the prior art StdT3 (Examples V3, E3).

TABLE 1

Structure of the OLEDS

| Ex. | HTL Thickness | IL Thickness | EBL Thickness | EML Thickness | HBL Thickness | ETL Thickness | EIL Thickness |
|---|---|---|---|---|---|---|---|
| V1 | SpA1 70 nm | HATCN 5 nm | SpMA1 90 nm | StdT1:TEG1 (90%:10%) 30 nm | — | ST1:LiQ (50%:50%) 40 nm | — |
| V2 | SpA1 70 nm | HATCN 5 nm | SpMA1 90 nm | StdT2:TEG1 (90%:10%) 30 nm | — | ST1:LiQ (50%:50%) 40 nm | — |
| V3 | SpA1 70 nm | HATCN 5 nm | SpMA1 90 nm | StdT3:TEG1 (90%:10%) 30 nm | — | ST1:LiQ (50%:50%) 40 nm | — |
| V4 | SpA1 70 nm | HATCN 5 nm | SpMA1 90 nm | StdT4:TEG1 (90%:10%) 30 nm | — | ST1:LiQ (50%:50%) 40 nm | — |
| V5 | SpA1 70 nm | HATCN 5 nm | SpMA1 90 nm | StdT5:TEG1 (90%:10%) 30 nm | — | ST1:LiQ (50%:50%) 40 nm | — |
| V6 | SpA1 70 nm | HATCN 5 nm | SpMA1 90 nm | StdT6:TEG1 (90%:10%) 30 nm | — | ST1:LiQ (50%:50%) 40 nm | — |
| V7 | SpA1 70 nm | HATCN 5 nm | SpMA1 90 nm | StdT7:TEG1 (90%:10%) 30 nm | — | ST1:LiQ (50%:50%) 40 nm | — |
| E1 | SpA1 70 nm | HATCN 5 nm | SpMA1 90 nm | FF1:TEG1 (90%:10%) 30 nm | — | ST1:LiQ (50%:50%) 40 nm | — |
| E2 | SpA1 70 nm | HATCN 5 nm | SpMA1 90 nm | FF2:TEG1 (90%:10%) 30 nm | — | ST1:LiQ (50%:50%) 40 nm | — |
| E3 | SpA1 70 nm | HATCN 5 nm | SpMA1 90 nm | FF3:TEG1 (90%:10%) 30 nm | — | ST1:LiQ (50%:50%) 40 nm | — |
| E4 | SpA1 70 nm | HATCN 5 nm | SpMA1 90 nm | FF4:TEG1 (90%:10%) 40 nm | — | ST1:LiQ (50%:50%) 30 nm | — |
| E5 | HATCN 5 nm | SpMA1 70 nm | SpMA2 15 nm | FF2:L1:TEY1 (45%:45%:10%) 25 nm | — | ST1 45 nm | LiQ 3 nm |
| E6 | SpA1 70 nm | HATCN 5 nm | SpMA1 90 nm | FF5:TEG1 (90%:10%) 30 nm | — | ST1:LiQ (50%:50%) 40 nm | — |
| E7 | SpA1 70 nm | HATCN 5 nm | SpMA1 90 nm | FF2:TEG1 (90%:10%) 30 nm | — | FF6:ST1 (50%:50%) 40 nm | LiQ 3 nm |
| E8 | SpA1 70 nm | HATCN 5 nm | SpMA1 90 nm | FF7:TEG1 (90%:10%) 30 nm | — | ST1:LiQ (50%:50%) 40 nm | — |
| E9 | SpA1 70 nm | HATCN 5 nm | SpMA1 90 nm | FF8:TEG1 (90%:10%) 30 nm | — | ST1:LiQ (50%:50%) 40 nm | — |
| E10 | SpA1 90 nm | HATCN 5 nm | SpMA1 130 nm | FF9:TER3 (92%:8%) 30 nm | — | ST1:LiQ (50%:50%) 40 nm | — |
| E11 | SpA1 70 nm | HATCN 5 nm | SpMA1 90 nm | FF10:TEG1 (90%:10%) 30 nm | — | ST1:LiQ (50%:50%) 40 nm | — |
| E12 | SpA1 70 nm | HATCN 5 nm | SpMA1 90 nm | FF11:TEG1 (90%:10%) 30 nm | — | ST1:LiQ (50%:50%) 40 nm | — |
| E13 | SpA1 70 nm | HATCN 5 nm | SpMA1 90 nm | FF12:TEG1 (90%:10%) 30 nm | — | ST1:LiQ (50%:50%) 40 nm | — |
| E14 | SpA1 70 nm | HATCN 5 nm | SpMA1 90 nm | FF13:TEG1 (45%:45%:10%) 30 nm | IC1 10 nm | ST1:LiQ (50%:50%) 30 nm | — |
| E15 | SpA1 70 nm | HATCN 5 nm | SpMA1 90 nm | FF14:IC3:TEG1 (45%:45%:10%) 30 nm | IC1 10 nm | ST1:LiQ (50%:50%) 30 nm | — |
| E16 | SpA1 70 nm | HATCN 5 nm | SpMA1 90 nm | FF15:IC3:TEG1 (90%:10%) 30 nm | IC1 10 nm | ST1:LiQ (50%:50%) 30 nm | — |
| E17 | SpA1 70 nm | HATCN 5 nm | SpMA1 90 nm | IC1:TEG1 (90%:10%) 30 nm | — | FF16:ST1 (50%:50%) 40 nm | LiF 1 nm |
| E18 | SpA1 70 nm | HATCN 5 nm | SpMA1 90 nm | IC1:TEG1 (90%:10%) 30 nm | FF17 10 nm | ST1:LiQ (50%:50%) 30 nm | — |
| E19 | SpA1 70 nm | HATCN 5 nm | SpMA1 90 nm | IC1:TEG1 (90%:10%) 30 nm | — | FF18:ST1 (50%:50%) 40 nm | LiQ 3 nm |
| E20 | SpA1 70 nm | HATCN 5 nm | SpMA1 90 nm | FF19:TEG1 (90%:10%) 30 nm | — | ST1:LiQ (50%:50%) 40 nm | — |
| E21 | SpA1 70 nm | HATCN 5 nm | SpMA1 90 nm | FF20:TEG1 (90%:10%) 30 nm | — | ST1:LiQ (50%:50%) 40 nm | — |
| E22 | SpA1 70 nm | HATCN 5 nm | SpMA1 90 nm | FF21:TEG1 (90%:10%) 30 nm | — | ST1:LiQ (50%:50%) 40 nm | — |
| E23 | SpA1 70 nm | HATCN 5 nm | SpMA1 90 nm | FF22:TEG1 (90%:10%) 30 nm | — | ST1:LiQ (50%:50%) 40 nm | — |

TABLE 2

Data of the OLEDs

| Ex. | U1000 (V) | CE1000 (cd/A) | PE1000 (lm/W) | EQE 1000 | CIE x/y at 1000 cd/m$^2$ | $L_0$; $j_0$ | L1 % | LT (h) |
|---|---|---|---|---|---|---|---|---|
| V1 | 3.6 | 50 | 44 | 14.4% | 0.33/0.62 | 20 mA/cm$^2$ | 80 | 120 |
| V2 | 3.3 | 60 | 57 | 17.0% | 0.34/0.62 | 20 mA/cm$^2$ | 80 | 110 |
| V3 | 4.1 | 41 | 31 | 11.9% | 0.32/0.63 | 20 mA/cm$^2$ | 80 | 110 |
| V4 | 3.3 | 57 | 54 | 15.5% | 0.32/0.63 | 20 mA/cm$^2$ | 80 | 100 |
| V5 | 3.7 | 59 | 50 | 15.6% | 0.33/0.62 | 20 mA/cm$^2$ | 80 | 110 |
| V6 | 3.8 | 61 | 50 | 16.3% | 0.33/0.62 | 20 mA/cm$^2$ | 80 | 120 |
| V7 | 3.7 | 65 | 55 | 17.3% | 0.33/0.63 | 20 mA/cm$^2$ | 80 | 160 |
| E1 | 3.5 | 52 | 46 | 14.6% | 0.33/0.62 | 20 mA/cm$^2$ | 80 | 160 |
| E2 | 3.3 | 63 | 59 | 17.2% | 0.33/0.63 | 20 mA/cm$^2$ | 80 | 155 |
| E3 | 3.5 | 51 | 45 | 14.8% | 0.34/0.62 | 20 mA/cm$^2$ | 80 | 100 |
| E4 | 3.1 | 65 | 66 | 17.4% | 0.33/0.63 | 20 mA/cm$^2$ | 80 | 150 |
| E5 | 2.7 | 86 | 100 | 24.5% | 0.42/0.57 | 50 mA/cm$^2$ | 90 | 95 |
| E6 | 3.4 | 65 | 60 | 17.1% | 0.33/0.62 | 20 mA/cm$^2$ | 80 | 150 |
| E7 | 3.3 | 56 | 53 | 16.2% | 0.33/0.62 | 20 mA/cm$^2$ | 80 | 145 |
| E8 | 3.5 | 62 | 56 | 16.9% | 0.38/0.59 | 20 mA/cm$^2$ | 80 | 130 |
| E9 | 3.4 | 60 | 55 | 16.8% | 0.38/0.59 | 20 mA/cm$^2$ | 80 | 145 |
| E10 | 4.5 | 11 | 8 | 12.0% | 0.67/0.33 | 4000 cd/m$^2$ | 80 | 310 |
| E11 | 3.6 | 50 | 44 | 14.4% | 0.33/0.62 | 20 mA/cm$^2$ | 80 | 130 |
| E12 | 3.4 | 63 | 58 | 17.0% | 0.32/0.63 | 20 mA/cm$^2$ | 80 | 160 |
| E13 | 3.5 | 62 | 56 | 17.3% | 0.32/0.63 | 20 mA/cm$^2$ | 80 | 150 |
| E14 | 3.6 | 57 | 50 | 15.3% | 0.33/0.62 | 20 mA/cm$^2$ | 80 | 105 |
| E15 | 3.4 | 57 | 53 | 16.0% | 0.34/0.63 | 20 mA/cm$^2$ | 80 | 410 |
| E16 | 3.5 | 58 | 52 | 16.1% | 0.34/0.63 | 20 mA/cm$^2$ | 80 | 290 |
| E17 | 3.2 | 67 | 66 | 18.1% | 0.33/0.62 | 20 mA/cm$^2$ | 80 | 160 |
| E18 | 3.3 | 66 | 62 | 17.8% | 0.33/0.62 | 20 mA/cm$^2$ | 80 | 170 |
| E19 | 3.1 | 69 | 70 | 18.4% | 0.33/0.62 | 20 mA/cm$^2$ | 80 | 165 |
| E20 | 3.5 | 62 | 56 | 17.1% | 0.34/0.62 | 20 mA/cm$^2$ | 80 | 135 |
| E21 | 3.5 | 57 | 51 | 15.6% | 0.33/0.63 | 20 mA/cm$^2$ | 80 | 85 |
| E22 | 3.4 | 51 | 47 | 14.8% | 0.34/0.62 | 20 mA/cm$^2$ | 80 | 80 |
| E23 | 3.6 | 53 | 46 | 15.0% | 0.33/0.62 | 20 mA/cm$^2$ | 80 | 95 |

TABLE 3

Structural formulae of the materials for the OLEDs

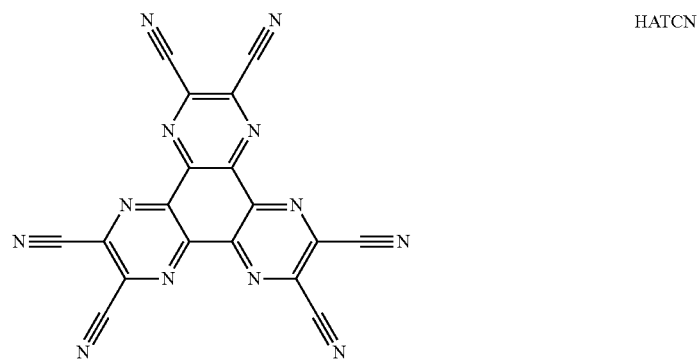

HATCN

TABLE 3-continued
Structural formulae of the materials for the OLEDs
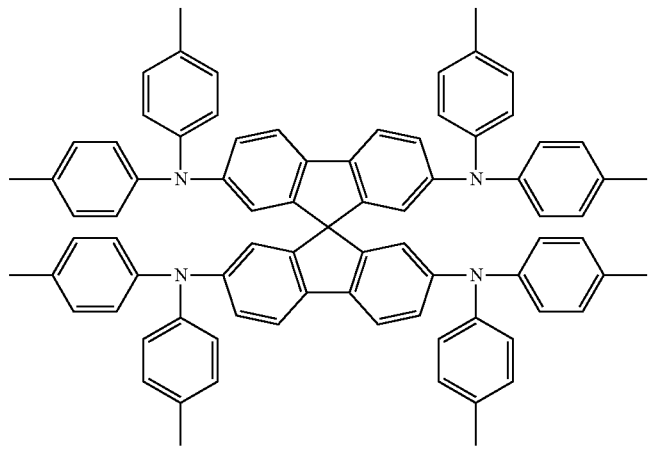
SpA1
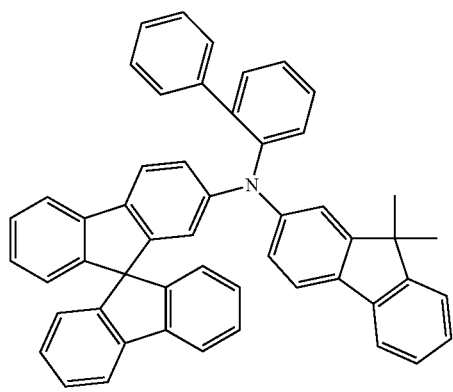 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
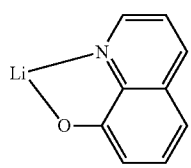
LiQ
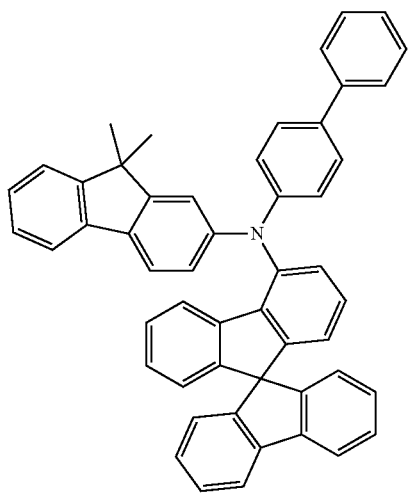 [SMILES: CC1(C)c2ccccc2-c2ccc(N(c3ccc(-c4ccccc4)cc3)c3cccc4c3-c3ccccc3C43c4ccccc4-c4ccccc43)cc21]
SpMA2

TABLE 3-continued
Structural formulae of the materials for the OLEDs
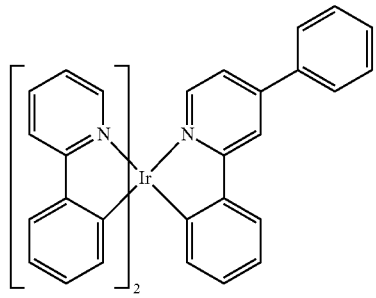
TEY1
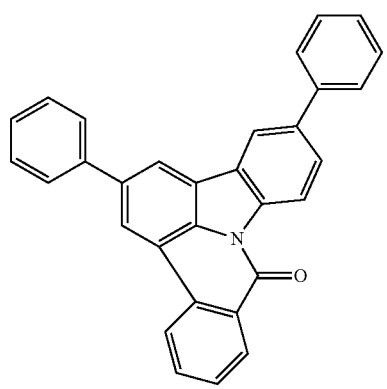 [SMILES: O=c1c2ccccc2c2cc(-c3ccccc3)cc3c4cc(-c5ccccc5)ccc4n1c23]
L1
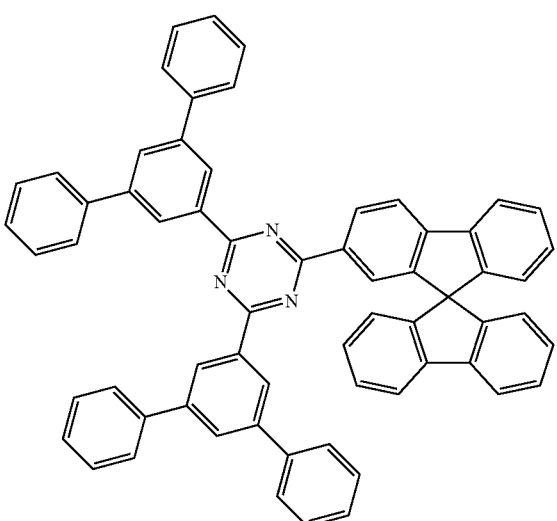
ST1
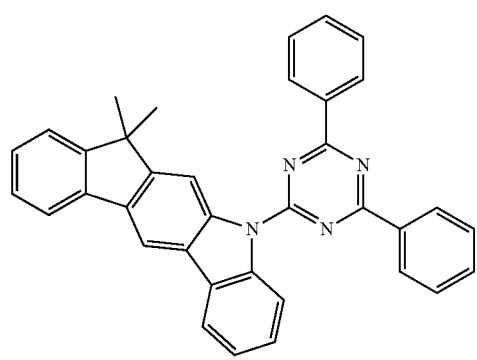 [SMILES: CC1(C)c2ccccc2-c2cc3c4ccccc4n(-c4nc(-c5ccccc5)nc(-c5ccccc5)n4)c3cc21]
IC1

TABLE 3-continued
Structural formulae of the materials for the OLEDs
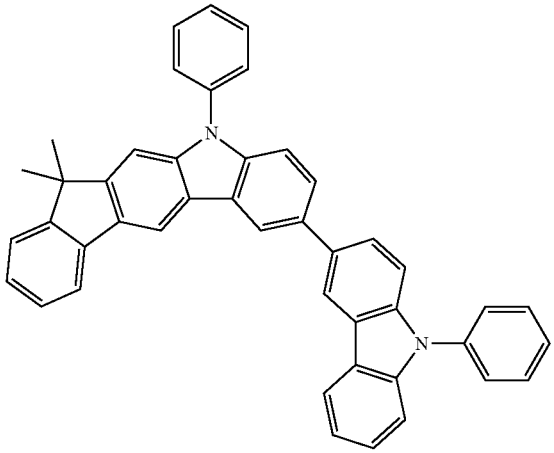 [SMILES: CC1(C)c2ccccc2-c2cc3c4cc(-c5ccc6c(c5)c5ccccc5n6-c5ccccc5)ccc4n(-c4ccccc4)c3cc21]
IC3
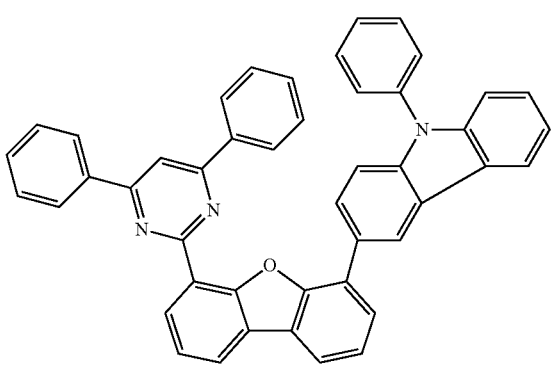 [SMILES: c1ccc(-c2cc(-c3ccccc3)nc(-c3cccc4c3oc3c(-c5ccc6c(c5)c5ccccc5n6-c5ccccc5)cccc34)n2)cc1]
StdT1
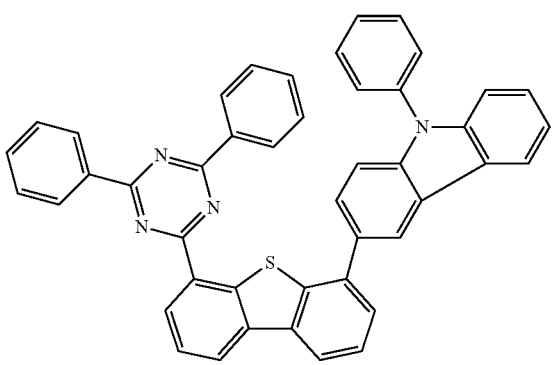 [SMILES: c1ccc(-c2nc(-c3ccccc3)nc(-c3cccc4c3sc3c(-c5ccc6c(c5)c5ccccc5n6-c5ccccc5)cccc34)n2)cc1]
StdT2

TABLE 3-continued
Structural formulae of the materials for the OLEDs
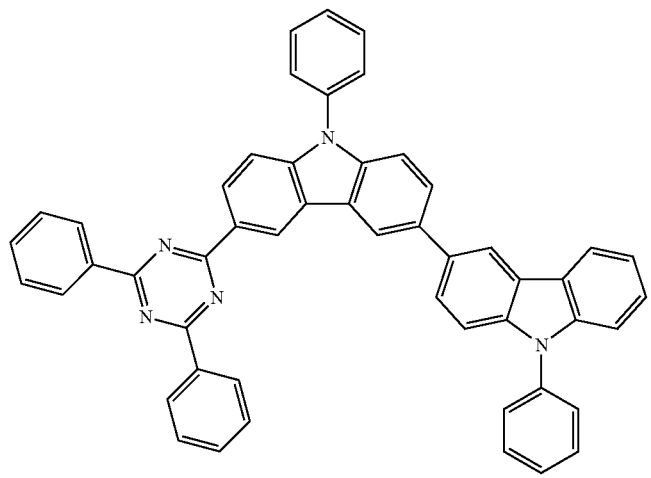 [SMILES: c1ccc(-c2nc(-c3ccccc3)nc(-c3ccc4c(c3)c3cc(-c5ccc6c(c5)c5ccccc5n6-c5ccccc5)ccc3n4-c3ccccc3)n2)cc1]
StdT3
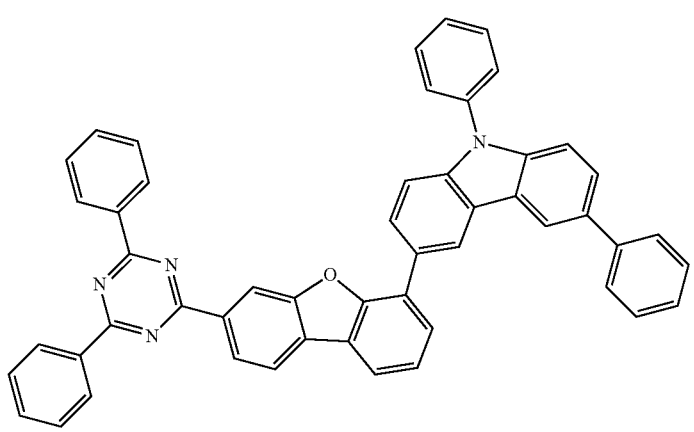 [SMILES: c1ccc(-c2ccc3c(c2)c2cc(-c4cccc5c4oc4cc(-c6nc(-c7ccccc7)nc(-c7ccccc7)n6)ccc45)ccc2n3-c2ccccc2)cc1]
StdT4
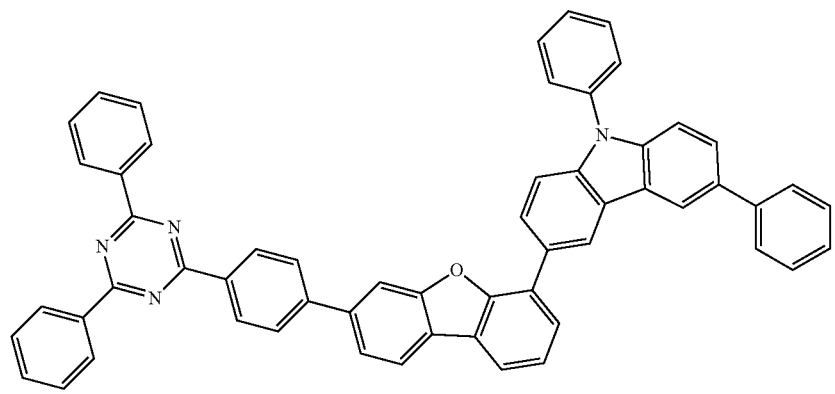 [SMILES: c1ccc(-c2ccc3c(c2)c2cc(-c4cccc5c4oc4cc(-c6ccc(-c7nc(-c8ccccc8)nc(-c8ccccc8)n7)cc6)ccc45)ccc2n3-c2ccccc2)cc1]
StdT5

TABLE 3-continued
Structural formulae of the materials for the OLEDs
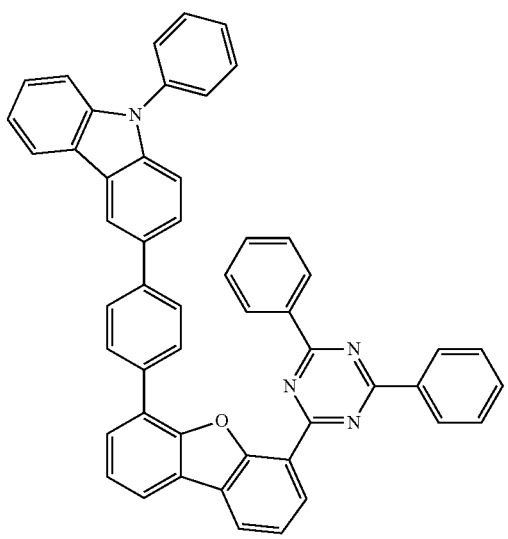 [SMILES: c1ccc(-c2nc(-c3ccccc3)nc(-c3cccc4c3oc3c(-c5ccc(-c6ccc7c(c6)c6ccccc6n7-c6ccccc6)cc5)cccc34)n2)cc1] StdT6
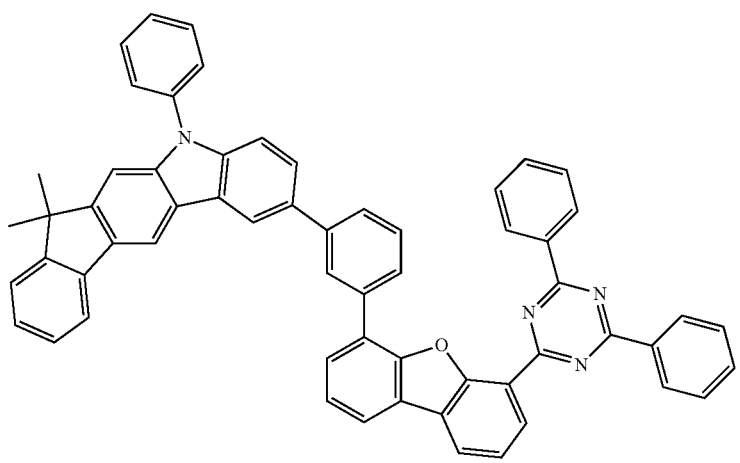 [SMILES: CC1(C)c2ccccc2-c2cc3c4cc(-c5cccc(-c6cccc7c6oc6c(-c8nc(-c9ccccc9)nc(-c9ccccc9)n8)cccc67)c5)ccc4n(-c4ccccc4)c3cc21] StdT7
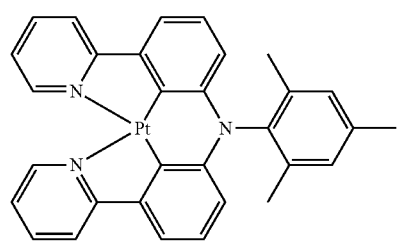 TER3
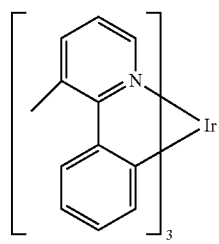 TEG1

TABLE 3-continued
Structural formulae of the materials for the OLEDs
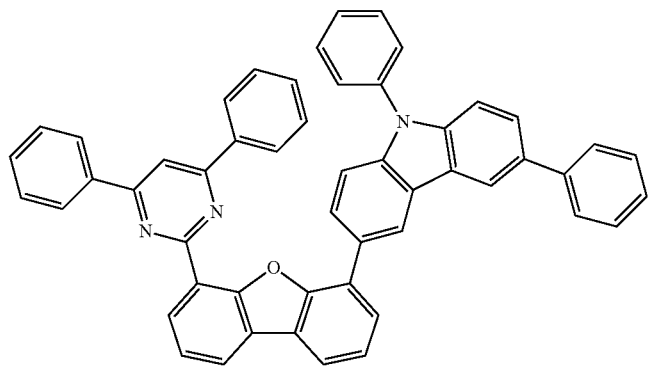 [SMILES: c1ccc(-c2ccc3c(c2)c2cc(-c4cccc5c4oc4c(-c6nc(-c7ccccc7)cc(-c7ccccc7)n6)cccc45)ccc2n3-c2ccccc2)cc1]
FF1
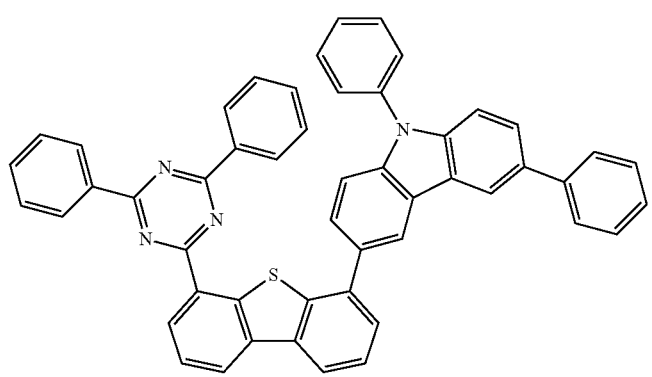 [SMILES: c1ccc(-c2ccc3c(c2)c2cc(-c4cccc5c4sc4c(-c6nc(-c7ccccc7)nc(-c7ccccc7)n6)cccc45)ccc2n3-c2ccccc2)cc1]
FF2
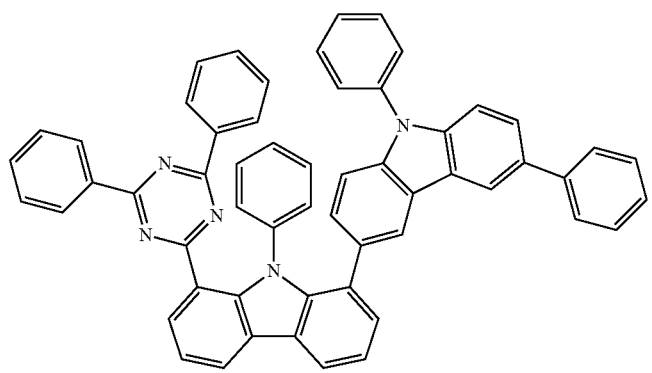 [SMILES: c1ccc(-c2ccc3c(c2)c2cc(-c4cccc5c6cccc(-c7nc(-c8ccccc8)nc(-c8ccccc8)n7)c6n(-c6ccccc6)c45)ccc2n3-c2ccccc2)cc1]
FF3
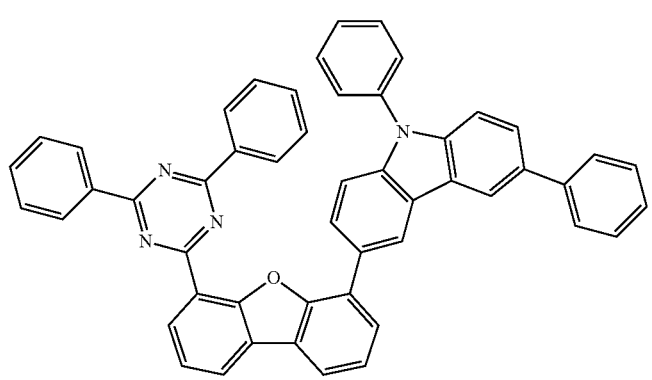 [SMILES: c1ccc(-c2ccc3c(c2)c2cc(-c4cccc5c4oc4c(-c6nc(-c7ccccc7)nc(-c7ccccc7)n6)cccc45)ccc2n3-c2ccccc2)cc1]
FF4

TABLE 3-continued
Structural formulae of the materials for the OLEDs
FF5
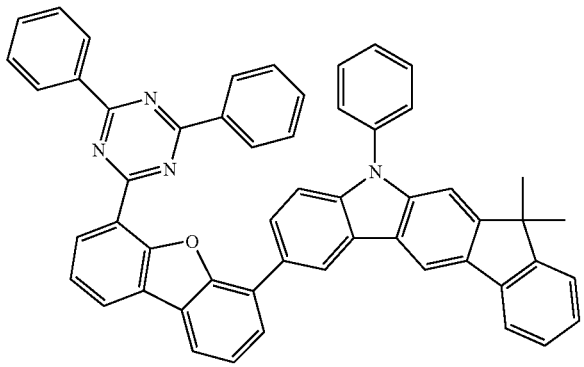 [SMILES: CC1(C)c2ccccc2-c2cc3c4cc(-c5cccc6c5oc5c(-c7nc(-c8ccccc8)nc(-c8ccccc8)n7)cccc56)ccc4n(-c4ccccc4)c3cc21]
FF6
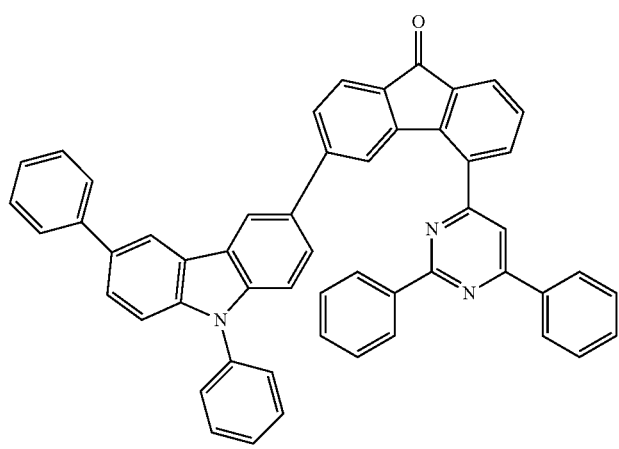 [SMILES: O=C1c2ccc(-c3ccc4c(c3)c3cc(-c5ccccc5)ccc3n4-c3ccccc3)cc2-c2c1cccc2-c1cc(-c2ccccc2)nc(-c2ccccc2)n1]
FF7
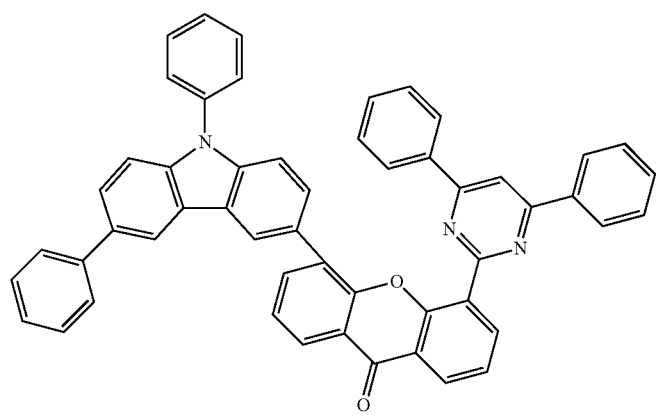 [SMILES: O=c1c2cccc(-c3ccc4c(c3)c3cc(-c5ccccc5)ccc3n4-c3ccccc3)c2oc2c(-c3nc(-c4ccccc4)cc(-c4ccccc4)n3)cccc12]

TABLE 3-continued
Structural formulae of the materials for the OLEDs
FF8
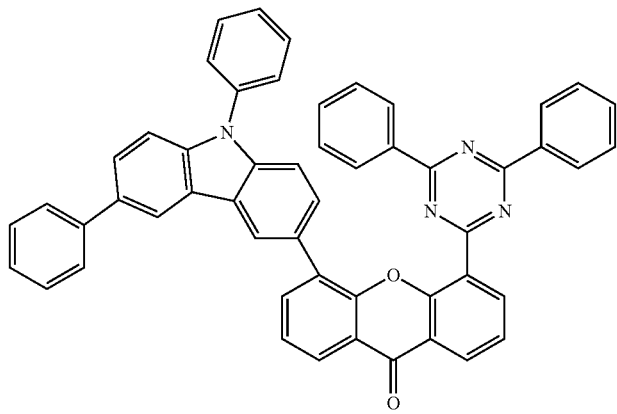 [SMILES: O=c1c2cccc(-c3ccc4c(c3)c3cc(-c5ccccc5)ccc3n4-c3ccccc3)c2oc2c(-c3nc(-c4ccccc4)nc(-c4ccccc4)n3)cccc12]
FF9
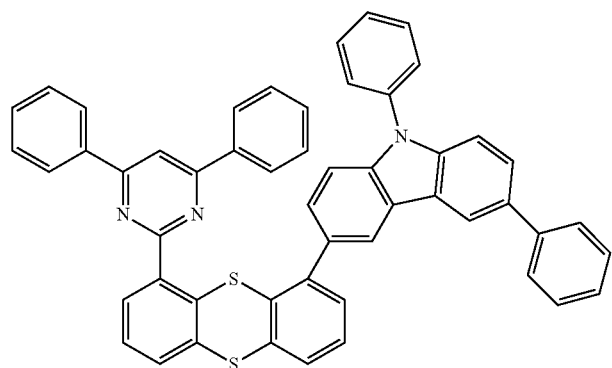 [SMILES: c1ccc(-c2ccc3c(c2)c2cc(-c4cccc5c4Sc4c(cccc4-c4nc(-c6ccccc6)cc(-c6ccccc6)n4)S5)ccc2n3-c2ccccc2)cc1]
FF10
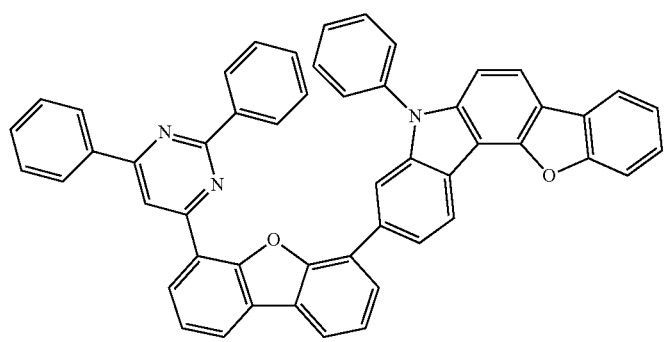 [SMILES: c1ccc(-c2cc(-c3cccc4c3oc3c(-c5ccc6c7c8oc9ccccc9c8ccc7n(-c7ccccc7)c6c5)cccc34)nc(-c3ccccc3)n2)cc1]
FF11
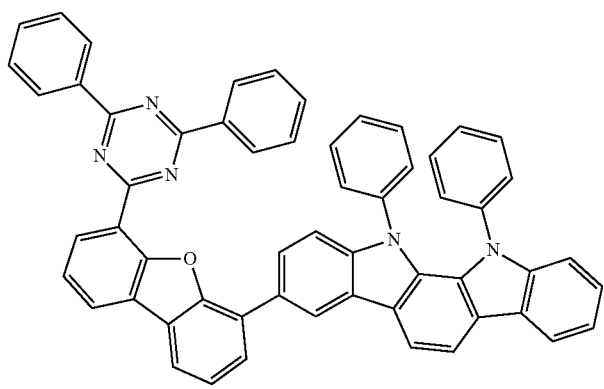 [SMILES: c1ccc(-c2nc(-c3ccccc3)nc(-c3cccc4c3oc3c(-c5ccc6c(c5)c5ccc7c8ccccc8n(-c8ccccc8)c7c5n6-c5ccccc5)cccc34)n2)cc1]

TABLE 3-continued
Structural formulae of the materials for the OLEDs
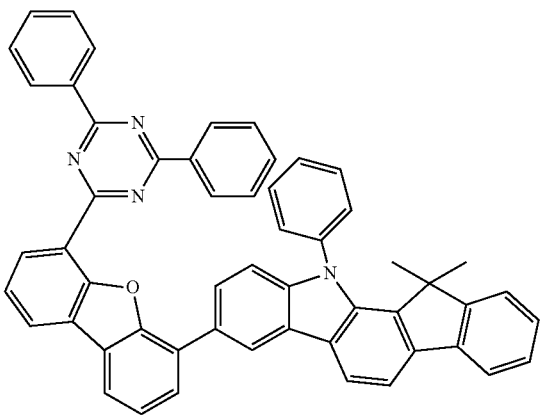 [SMILES: CC1(C)c2ccccc2-c2ccc3c4cc(-c5cccc6c5oc5c(-c7nc(-c8ccccc8)nc(-c8ccccc8)n7)cccc56)ccc4n(-c4ccccc4)c3c21]
FF12
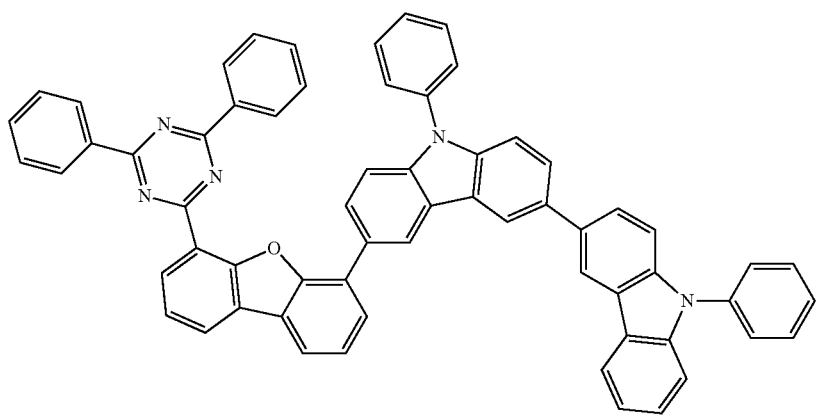 [SMILES: c1ccc(-c2nc(-c3ccccc3)nc(-c3cccc4c3oc3c(-c5ccc6c(c5)c5cc(-c7ccc8c(c7)c7ccccc7n8-c7ccccc7)ccc5n6-c5ccccc5)cccc34)n2)cc1]
FF13
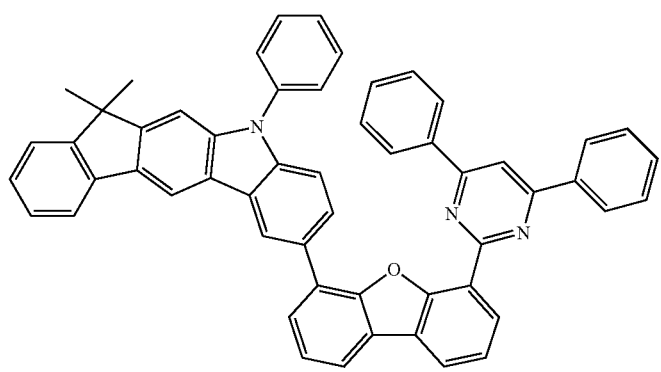 [SMILES: CC1(C)c2ccccc2-c2cc3c4cc(-c5cccc6c5oc5c(-c7nc(-c8ccccc8)cc(-c8ccccc8)n7)cccc56)ccc4n(-c4ccccc4)c3cc21]
FF14
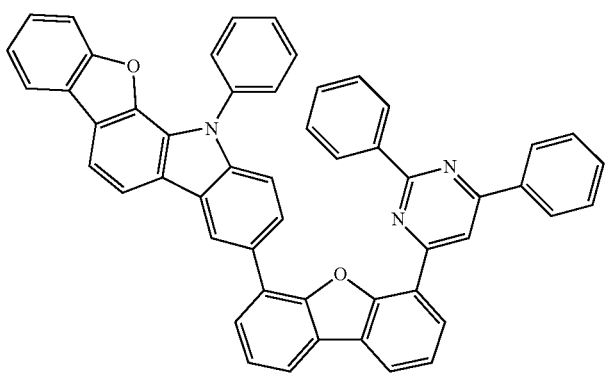 [SMILES: c1ccc(-c2cc(-c3cccc4c3oc3c(-c5ccc6c(c5)c5ccc7c8ccccc8oc7c5n6-c5ccccc5)cccc34)nc(-c3ccccc3)n2)cc1]
FF15

TABLE 3-continued
Structural formulae of the materials for the OLEDs
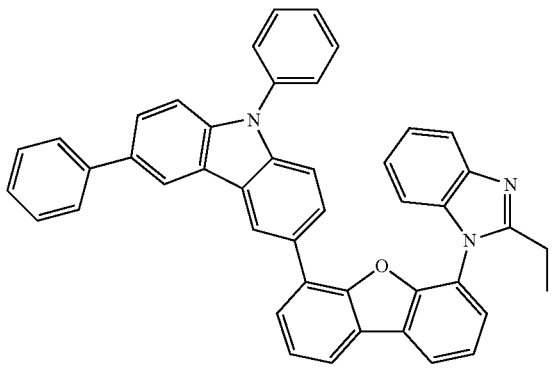 [SMILES: CCc1nc2ccccc2n1-c1cccc2c1oc1c(-c3ccc4c(c3)c3cc(-c5ccccc5)ccc3n4-c3ccccc3)cccc12]
FF16
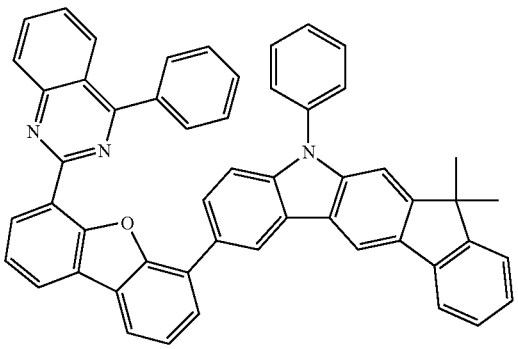 [SMILES: CC1(C)c2ccccc2-c2cc3c4cc(-c5cccc6c5oc5c(-c7nc(-c8ccccc8)c8ccccc8n7)cccc56)ccc4n(-c4ccccc4)c3cc21]
FF17
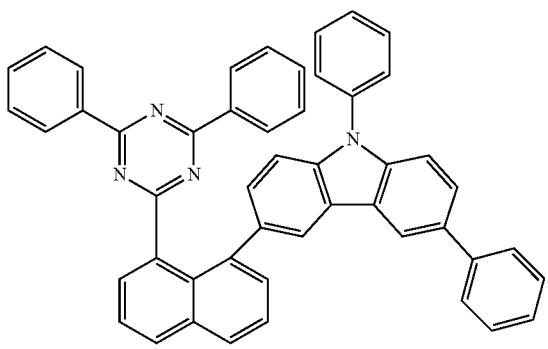 [SMILES: c1ccc(-c2ccc3c(c2)c2cc(-c4cccc5cccc(-c6nc(-c7ccccc7)nc(-c7ccccc7)n6)c45)ccc2n3-c2ccccc2)cc1]
FF18
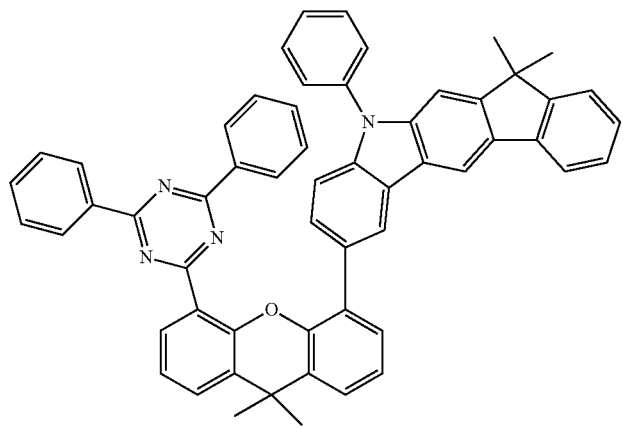 [SMILES: CC1(C)c2ccccc2-c2cc3c4cc(-c5cccc6c5Oc5c(-c7nc(-c8ccccc8)nc(-c8ccccc8)n7)cccc5C6(C)C)ccc4n(-c4ccccc4)c3cc21]
FF19

TABLE 3-continued
Structural formulae of the materials for the OLEDs
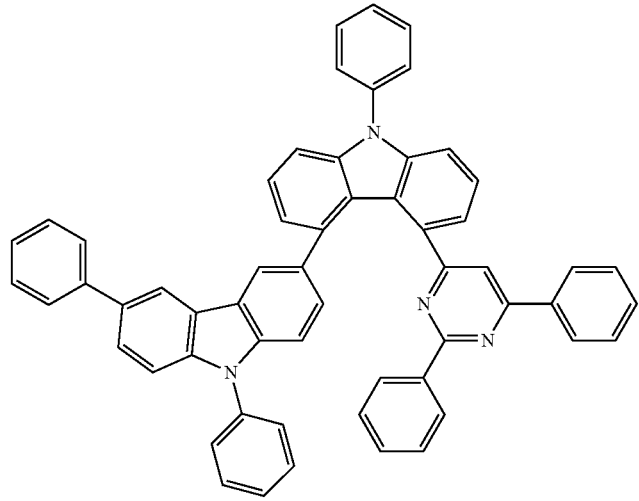 [SMILES: c1ccc(-c2ccc3c(c2)c2cc(-c4cccc5c4c4c(-c6cc(-c7ccccc7)nc(-c7ccccc7)n6)cccc4n5-c4ccccc4)ccc2n3-c2ccccc2)cc1]
FF20
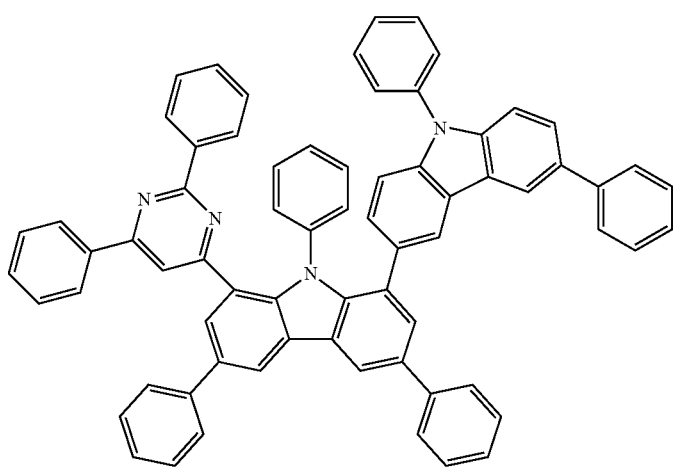 [SMILES: c1ccc(-c2ccc3c(c2)c2cc(-c4cc(-c5ccccc5)cc5c6cc(-c7ccccc7)cc(-c7cc(-c8ccccc8)nc(-c8ccccc8)n7)c6n(-c6ccccc6)c45)ccc2n3-c2ccccc2)cc1]
FF21
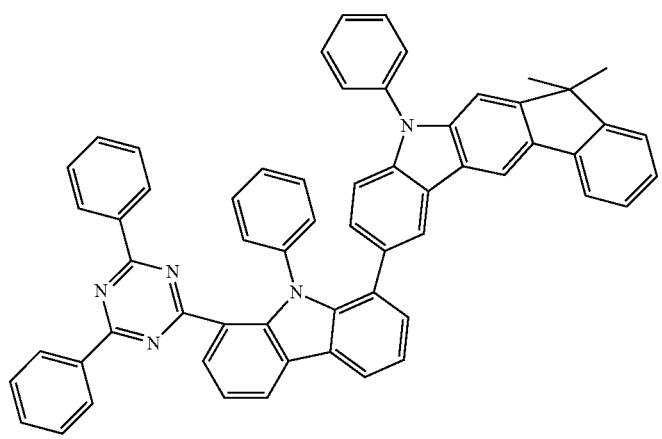 [SMILES: CC1(C)c2ccccc2-c2cc3c4cc(-c5cccc6c7cccc(-c8nc(-c9ccccc9)nc(-c9ccccc9)n8)c7n(-c7ccccc7)c56)ccc4n(-c4ccccc4)c3cc21]
FF22

The invention claimed is:
1. Compound of the general formula (1)

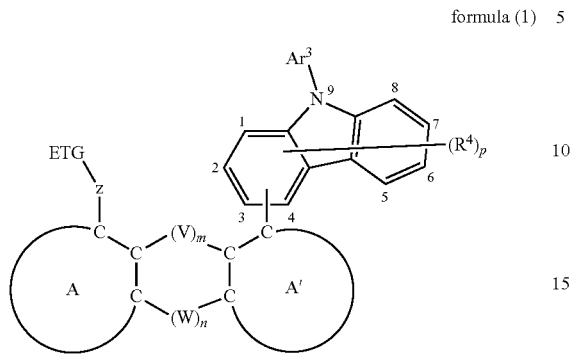

formula (1)

where the following applies to the symbols and indices used:

A and A' are, identically or differently from one another, an aromatic or heteroaromatic ring having 5 or 6 ring atoms, which may be substituted by one or more radicals $R^1$, which may be independent of one another;

ETG is an organic electron-transporting group (ETG) from the group of electron-deficient heteroaromatic groups, where the ETG is selected from the group consisting of triazines, pyrimidines, pyrazines, pyrazoles, pyridazines, quinoles, isoquinolines, thiazoles, benzothiazoles, oxazoles, benzoxazoles, imidazoles, benzimidazoles, and pyridines, and where the group ETG may be substituted by one or more radicals $R^1$, which are independent of one another;

Z is a single bond or a divalent group; if Z is a single bond, the group ETG is then bonded directly to the carbon atom of ring A;

V is O;

W is a single bond;

m is 1;

n is 1, where m=n;

$Ar^3$ is an aromatic or heteroaromatic ring or ring system having 5 to 30 ring atoms, where the ring or ring system may in each case be substituted by one or more radicals $R^2$ where two or more radicals $R^2$ do not form a ring closure with one another;

$R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups or a crosslinkable group Q; two or more adjacent radicals $R^1$ here may form a mono- or polycyclic, aliphatic or aromatic ring system with one another, where it is preferred for two or more adjacent radicals $R^1$ not to form a mono- or polycyclic, aliphatic or aromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which may be substituted by one or more radicals $R^3$, or a diarylamino group, diheteroarylamino group or arylheteroarylamino group having 10 to 40 aromatic ring atoms, which may be substituted by one or more radicals $R^3$, or a combination of two or more of these groups; two or more adjacent radicals $R^2$ here do not form a mono- or polycyclic, aliphatic or aromatic ring system with one another $R^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents $R^3$ here do not form a mono- or polycyclic, aliphatic or aromatic ring system with one another;

p is 1;

$R^4$ is, identically or differently on each occurrence, a straight-chain alkyl group having 1 to 40 C atoms or a branched or cyclic alkyl group having 3 to 40 C atoms, each of which may be substituted by one or more radicals $R^2$, where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or a combination of two or more of these groups.

2. Compound according to claim 1, characterised in that it has the formula (2)

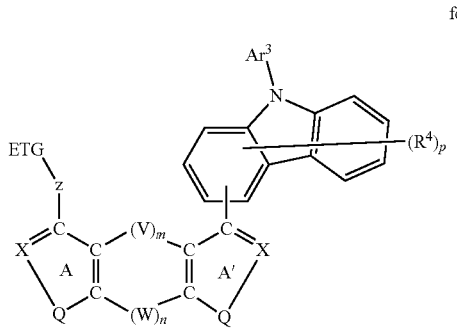

formula (2)

where the above definitions apply to the indices and symbols used, and where:
X is, identically or differently on each occurrence, N or CR$^1$;
Q is, identically or differently on each occurrence, X=X, S, O or NR$^1$.

3. Compound according to claim 1, characterised in that it has the formula (3)

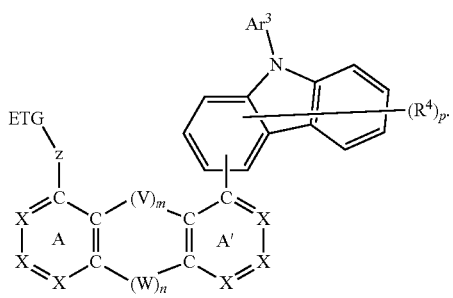

formula (3)

4. Compound according to claim 1, characterised in that it has the formula (3a)

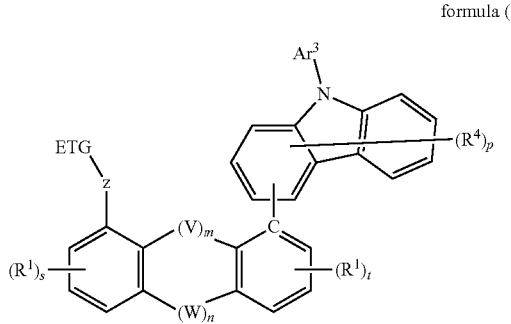

formula (3a)

where s and t can be integers from 0 to 3 and where s+t is equal to an integer from 0 to 6.

5. Compound according to claim 1, characterised in that it has the formula (3b)

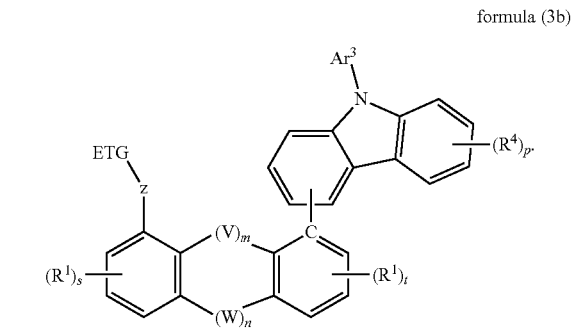

formula (3b)

6. Compound according to claim 1, characterised in that it has the formula (3c)

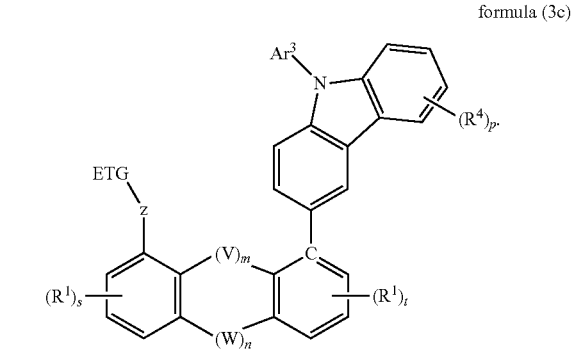

formula (3c)

7. Compound according to claim 1, characterised in that Z is a single bond or a divalent aromatic or heteroaromatic ring or ring system having 5 to 60 ring atoms.

8. Process for the preparation of the compound according to claim 1 with the aid of Suzuki coupling.

9. Process for the preparation of the compound according to claim 1 with the aid of Buchwald or Ullmann coupling.

10. Composition comprising at least one compound according to claim 1 and at least one further compound selected from the group consisting of fluorescent emitters, phosphorescent emitters, host materials, matrix materials, electron-transport materials, electron-injection materials, hole-conductor materials, hole-injection materials, electron-blocking materials, hole-blocking materials, n-dopants and p-dopants.

11. Composition according to claim 10, characterised in that the additional compound is a phosphorescent emitter.

12. Composition according to claim 10, characterised in that the additional compound is a host material or matrix material.

13. Composition according to claim 11, characterised in that the additional compound has a band gap of 2.5 eV or more.

14. Formulation comprising at least one compound according to claim 1 and at least one solvent.

15. Electronic device comprising at least one compound according to claim 1.

16. Electronic device according to claim 15, characterised in that the electronic device is selected from organic integrated circuits (OICs), organic field-effect transistors (OFETs), organic thin-film transistors (OTFTs), organic electroluminescent devices, organic solar cells (OSCs), organic optical detectors, organic photoreceptors.

17. Electronic device according to claim 15, characterised in that the electronic device is an organic electroluminescent device which is also selected from the group consisting of organic light-emitting transistors (OLETs), organic field-quench devices (OFQDs), organic light-emitting electrochemical cells (OLECs, LECs, LEECs), organic laser diodes (O-lasers) and organic light-emitting diodes (OLEDs), preferably OLECs and OLEDs, very preferably OLEDs.

18. Process for the production of an electronic device according to claim 15, characterised in that at least one organic layer is applied by gas-phase deposition or from solution.

19. Electronic device according to claim 17, for use in medicine for phototherapy, preferably for use for phototherapy of the skin, very preferably for use for the treatment or prevention of psoriasis, atopic dermatitis, jaundice, jaundice of the newborn, vitiligo, inflammation, pain and for use for wound healing.

20. Use of the device according to claim 17 in cosmetics, preferably for the treatment or prevention of skin ageing, skin wrinkles, crow's feet, acne, blackheads and cellulite.

21. Use of the device according to claim 17 in displays or for lighting.

22. Compound of the general formula (1)

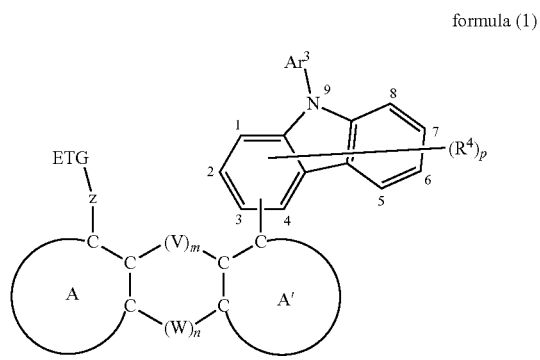

formula (1)

where the following applies to the symbols and indices used:

A and A' are, identically or differently from one another, an aromatic or heteroaromatic ring having 5 or 6 ring atoms, which may be substituted by one or more radicals $R^1$, which may be independent of one another;

ETG is an organic electron-transporting group (ETG) from the group of electron-deficient heteroaromatic groups, where the ETG is selected from the group consisting of triazines, pyrimidines, pyrazines, pyrazoles, pyridazines, quinoles, isoquinolines, thiazoles, benzothiazoles, oxazoles, benzoxazoles, imidazoles, benzimidazoles and pyridines and where the group ETG may be substituted by one or more radicals $R^1$, which are independent of one another;

Z is a single bond or a divalent group; if Z is a single bond, the group ETG is then Z bonded directly to the carbon atom of ring A;

V is O;
W is a single bond;
m is 1;
n is 1,
where m=n;

$Ar^3$ is an aromatic or heteroaromatic ring or ring system having 5 to 30 ring atoms, where the ring or ring system may in each case be substituted by one or more radicals $R^2$ where two or more radicals $R^2$ do not form a ring closure with one another;

$R^1$ is, identically or differently on each occurrence, H, D, F, Cl, Br, I, $N(R^2)_2$, CN, $NO_2$, $Si(R^2)_3$, $B(OR^2)_2$, C(=O) $R^2$, P(=O)$(R^2)_2$, S(=O) $R^2$, S(=O)$_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C$=$CR^2$, C=C, $Si(R^2)_2$, $Ge(R^2)_2$, $Sn(R^2)_2$, C=O, C=S, C=Se, C=$NR^2$, P(=O)($R^2$), SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups or a crosslinkable group Q; two or more adjacent radicals $R^1$ here may form a mono- or polycyclic, aliphatic or aromatic ring system with one another, where it is preferred for two or more adjacent radicals $R^1$ not to form a mono- or polycyclic, aliphatic or aromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, C(=O)$R^3$, P(=O)$(R^3)_2$, S(=O)$R^3$, S(=O)$_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^3$, where one or more non-adjacent $CH_2$ groups may be replaced by $R^3C$=$CR^3$, C=C, $Si(R^3)_2$, $Ge(R^3)_2$, $Sn(R^3)_2$, C=O, C=S, C=Se, C=$NR^3$, P(=O) ($R^3$), SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which may be substituted by one or more radicals $R^3$, or a diarylamino group, diheteroarylamino group or arylheteroarylamino group having 10 to 40 aromatic ring atoms, which may be substituted by one or more radicals $R^3$, or a combination of two or more of these groups; two or more adjacent radicals $R^2$ here do not form a mono- or polycyclic, aliphatic or aromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents $R^3$ here do not form a mono- or polycyclic, aliphatic or aromatic ring system with one another;

p is 1;

$R^4$ is, identically or differently on each occurrence, a straight-chain alkyl group having 1 to 40 C atoms or a branched or cyclic alkyl group having 3 to 40 C atoms, each of which may be substituted by one or more radicals $R^2$ where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or a combination of two or more of these groups.

* * * * *